US011746346B2

(12) United States Patent
Wasels et al.

(10) Patent No.: US 11,746,346 B2
(45) Date of Patent: Sep. 5, 2023

(54) **GENETIC TOOL FOR THE TRANSFORMATION OF *CLOSTRIDIUM* BACTERIA**

(71) Applicants: IFP ENERGIES NOUVELLES, Rueil Malmaison (FR); STICHTING WAGENINGEN RESEARCH, Wageningen (NL)

(72) Inventors: Francois Wasels, Metz (FR); Nicolas Lopes Ferreira, Croisilles (FR); Florent Collas, Aachen (DE); Ana Lopez Contreras, Utrecht (NL)

(73) Assignees: STICHTING WAGENINGEN RESEARCH, Pb Wageningen (NL); IFP ENERGIES NOUVELLES, Rueil Malmaison (FR)

( * ) Notice: Subject to any disclaimer, the term of this patent is extended or adjusted under 35 U.S.C. 154(b) by 907 days.

(21) Appl. No.: 15/768,018

(22) PCT Filed: Oct. 14, 2016

(86) PCT No.: PCT/FR2016/052663

§ 371 (c)(1),
(2) Date: Apr. 13, 2018

(87) PCT Pub. No.: WO2017/064439

PCT Pub. Date: Apr. 20, 2017

(65) Prior Publication Data

US 2018/0305680 A1 Oct. 25, 2018

(30) Foreign Application Priority Data

Oct. 16, 2015 (FR) ...................................... 1559846

(51) Int. Cl.

| | |
|---|---|
| ***C12N 15/10*** | (2006.01) |
| ***C12N 9/22*** | (2006.01) |
| ***C12N 15/74*** | (2006.01) |
| ***C12N 15/90*** | (2006.01) |
| ***C12P 7/06*** | (2006.01) |
| ***C12P 7/28*** | (2006.01) |
| ***C12P 7/04*** | (2006.01) |
| ***C12N 15/63*** | (2006.01) |
| ***C12N 1/20*** | (2006.01) |
| ***C12R 1/145*** | (2006.01) |

(52) U.S. Cl.

CPC ........... *C12N 15/102* (2013.01); *C12N 1/205* (2021.05); *C12N 9/22* (2013.01); *C12N 15/63* (2013.01); *C12N 15/74* (2013.01); *C12N 15/902* (2013.01); *C12P 7/04* (2013.01); *C12P 7/065* (2013.01); *C12P 7/28* (2013.01); *C12R 2001/145* (2021.05); *Y02E 50/10* (2013.01)

(58) Field of Classification Search

CPC .... C12N 9/22; C12N 2310/20; C12N 15/113; C12N 15/102; C12N 15/902; C12N 15/07

See application file for complete search history.

(56) References Cited

U.S. PATENT DOCUMENTS

| | | | | |
|---|---|---|---|---|
| 2014/0068797 | A1* | 3/2014 | Doudna | C12N 9/22 800/18 |
| 2016/0340661 | A1* | 11/2016 | Cong | C12N 15/907 |
| 2018/0305680 | A1 | 10/2018 | Wasels et al. | |
| 2019/0367947 | A1 | 12/2019 | Lopes Ferreira et al. | |

FOREIGN PATENT DOCUMENTS

| | | |
|---|---|---|
| WO | WO 2017/064439 | 4/2017 |

OTHER PUBLICATIONS

Wasels, F. et al. "A two-plasmid inducible CRISPR/Cas9 genome editing tool for *Clostridium acetobutylicum*" *Journal of Microbiological Methods*, 2017, pp. 5-11, vol. 140.

Rauch, B. J. et al. "Inhibition of CRISPR-Cas9 with Bacteriophage Proteins" *Cell*, Jan. 12, 2017, pp. 150-158, vol. 168, No. 1, Supplemental pp. e1-e4, Supplemental Figures pp. 1-6.

Pawluk, A. et al. "Anti-CRISPR: discovery, mechanism and function" *Nature Reviews*, Jan. 2018, pp. 12-17, vol. 16, No. 1.

Pawluk, A. et al. "Naturally Occurring Off-Switches for CRISPR-Cas9" *Cell*, Dec. 15, 2016, pp. 1829-1838, vol. 167, No. 7, Supplemental pp. e1-e5, Supplemental Figures pp. 1-4.

Negahdaripour, M. et al. "Investigating CRISPR-Cas systems in *Clostridium botulinum* via bioinformatics tools" *Infection, Genetics and Evolution*, 2017, pp. 355-373, vol. 54.

French Preliminary Search Report and Written Opinion for FR 1854835 dated Nov. 27, 2018, pp. 1-9.

Claims as filed for U.S. Serial No. 16/421,572,2019, pp. 1-3.

Collas, F. et al. "Simultaneous production of isopropanol, butanol, ethanol and 2,3-butanediol by *Clostridium acetobutylicum* ATCC 824 engineered strains" *AMB Express*, Jan. 1, 2012, pp. 1-10, vol. 2, No. 45.

Cornillot, E. et al. "The Genes for Butanol and Acetone Formation in *Clostridium acetobutylicum* ATCC 824 Reside on a Large Plasmid Whose Loss Leads to Degeneration of the Strain" *Journal of Bacteriology*, Sep. 1997, pp. 5442-5447, vol. 179, No. 17.

Wang, Y. et al. "Markerless chromosomal gene deletion in *Clostridium beijerinckii* using CRISPR/Cas9 system" *Journal of Biotechnology*, Apr. 20, 2015, pp. 1-5, vol. 200.

(Continued)

*Primary Examiner* — Nancy J Leith

(74) *Attorney, Agent, or Firm* — SALIWANCHIK, LLOYD & EISENSCHENK

(57) ABSTRACT

The present invention relates to a genetic tool comprising at least two different nucleic acids allowing the transformation, by homologous recombination, of a bacterium of the genus *Clostridium*, typically of a solventogenic bacterium.

11 Claims, 24 Drawing Sheets

Figure 1:
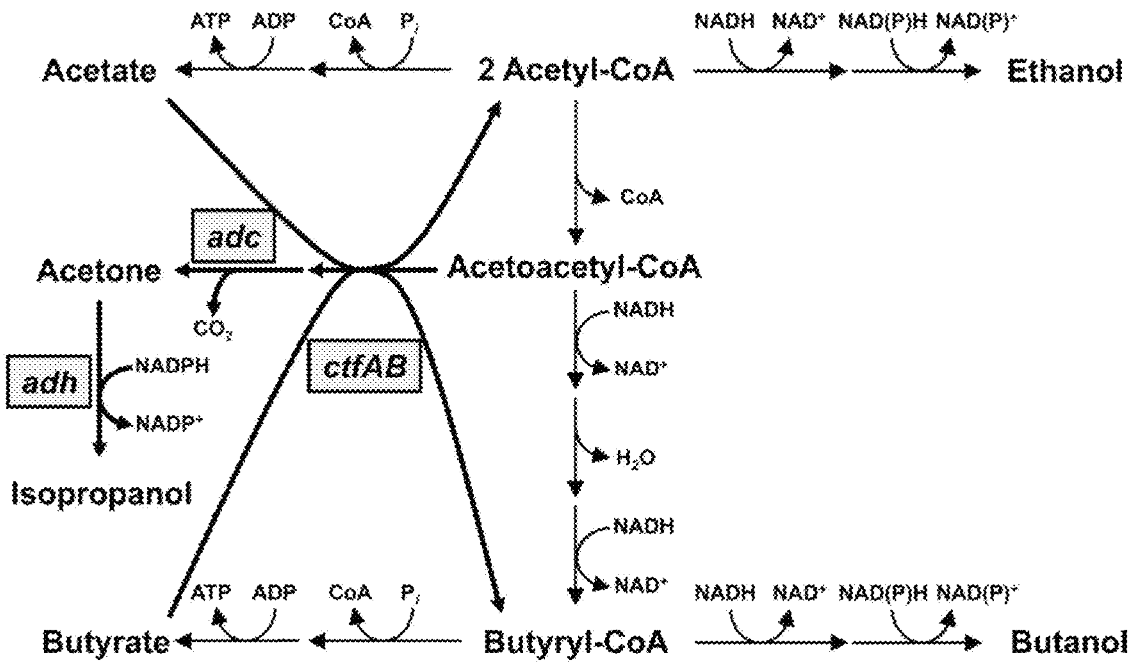

Specification includes a Sequence Listing.

(56) References Cited

OTHER PUBLICATIONS

Xu, T. et al. "Efficient Genome Editing in *Clostridium cellulolyticum* via CRISPR-Cas9 Nickase" *Applied and Environmental Microbiology*, Jul. 2015 (posted online Apr. 24, 2015), pp. 4423-4431, vol. 81, No. 13.
Xu, T. et al. "Supplementary Data for Efficient Genome Editing in *Clostridium cellulolyticum* via CRISPR-Cas9 Nickase" *Applied and Environmental Microbiology*, Apr. 24, 2015, pp. 1-13.
Written Opinion in International Application No. PCT/FR2016/052663, dated Jan. 27, 2017, pp. 1-5.

* cited by examiner

SEQUENCE LISTING

<160> NUMBER OF SEQ ID NOS: 32

<210> SEQ ID NO 1
<211> LENGTH: 1368
<212> TYPE: PRT
<213> ORGANISM: Streptococcus pyogenes

<400> SEQUENCE: 1

```
Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365
```

-continued

```
Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
    610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
    690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
    770                 775                 780

Glu Glu Gly Ile Lys Glu Leu Gly Ser Gln Ile Leu Lys Glu His Pro
```

-continued

```
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp His Ile Val Pro Gln Ser Phe Leu Lys
        835                 840                 845

Asp Asp Ser Ile Asp Asn Lys Val Leu Thr Arg Ser Asp Lys Asn Arg
    850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
    930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys  Tyr Pro Lys Leu Glu  Ser Glu Phe
        995                 1000                1005

Val Tyr  Gly Asp Tyr Lys Val  Tyr Asp Val Arg Lys  Met Ile Ala
    1010                1015                1020

Lys Ser  Glu Gln Glu Ile Gly  Lys Ala Thr Ala Lys  Tyr Phe Phe
    1025                1030                1035

Tyr Ser  Asn Ile Met Asn Phe  Phe Lys Thr Glu Ile  Thr Leu Ala
    1040                1045                1050

Asn Gly  Glu Ile Arg Lys Arg  Pro Leu Ile Glu Thr  Asn Gly Glu
    1055                1060                1065

Thr Gly  Glu Ile Val Trp Asp  Lys Gly Arg Asp Phe  Ala Thr Val
    1070                1075                1080

Arg Lys  Val Leu Ser Met Pro  Gln Val Asn Ile Val  Lys Lys Thr
    1085                1090                1095

Glu Val  Gln Thr Gly Gly Phe  Ser Lys Glu Ser Ile  Leu Pro Lys
    1100                1105                1110

Arg Asn  Ser Asp Lys Leu Ile  Ala Arg Lys Lys Asp  Trp Asp Pro
    1115                1120                1125

Lys Lys  Tyr Gly Gly Phe Asp  Ser Pro Thr Val Ala  Tyr Ser Val
    1130                1135                1140

Leu Val  Val Ala Lys Val Glu  Lys Gly Lys Ser Lys  Lys Leu Lys
    1145                1150                1155

Ser Val  Lys Glu Leu Leu Gly  Ile Thr Ile Met Glu  Arg Ser Ser
    1160                1165                1170

Phe Glu  Lys Asn Pro Ile Asp  Phe Leu Glu Ala Lys  Gly Tyr Lys
    1175                1180                1185

Glu Val  Lys Lys Asp Leu Ile  Ile Lys Leu Pro Lys  Tyr Ser Leu
    1190                1195                1200
```

```
Phe Glu  Leu Glu Asn Gly Arg  Lys Arg Met Leu Ala  Ser Ala Gly
    1205                 1210                 1215

Glu Leu  Gln Lys Gly Asn Glu  Leu Ala Leu Pro Ser  Lys Tyr Val
    1220                 1225                 1230

Asn Phe  Leu Tyr Leu Ala Ser  His Tyr Glu Lys Leu  Lys Gly Ser
    1235                 1240                 1245

Pro Glu  Asp Asn Glu Gln Lys  Gln Leu Phe Val Glu  Gln His Lys
    1250                 1255                 1260

His Tyr  Leu Asp Glu Ile Ile  Glu Gln Ile Ser Glu  Phe Ser Lys
    1265                 1270                 1275

Arg Val  Ile Leu Ala Asp Ala  Asn Leu Asp Lys Val  Leu Ser Ala
    1280                 1285                 1290

Tyr Asn  Lys His Arg Asp Lys  Pro Ile Arg Glu Gln  Ala Glu Asn
    1295                 1300                 1305

Ile Ile  His Leu Phe Thr Leu  Thr Asn Leu Gly Ala  Pro Ala Ala
    1310                 1315                 1320

Phe Lys  Tyr Phe Asp Thr Thr  Ile Asp Arg Lys Arg  Tyr Thr Ser
    1325                 1330                 1335

Thr Lys  Glu Val Leu Asp Ala  Thr Leu Ile His Gln  Ser Ile Thr
    1340                 1345                 1350

Gly Leu  Tyr Glu Thr Arg Ile  Asp Leu Ser Gln Leu  Gly Gly Asp
    1355                 1360                 1365
```

<210> SEQ ID NO 2
<211> LENGTH: 4107
<212> TYPE: DNA
<213> ORGANISM: Streptococcus pyogenes

<400> SEQUENCE: 2

```
atggataaga aatactcaat aggcttagat atcggcacaa atagcgtcgg atgggcggtg     60

atcactgatg aatataaggt tccgtctaaa aagttcaagg ttctgggaaa tacagaccgc    120

cacagtatca aaaaaaatct tataggggct cttttatttg acagtggaga gacagcggaa    180

gcgactcgtc tcaaacggac agctcgtaga aggtatacac gtcggaagaa tcgtatttgt    240

tatctacagg agattttttc aaatgagatg gcgaaagtag atgatagttt ctttcatcga    300

cttgaagagt cttttttggt ggaagaagac aagaagcatg aacgtcatcc tatttttgga    360

aatatagtag atgaagttgc ttatcatgag aaatatccaa ctatctatca tctgcgaaaa    420

aaattggtag attctactga taaagcggat ttgcgcttaa tctatttggc cttagcgcat    480

atgattaagt ttcgtggtca tttttttgatt gagggagatt taaatcctga taatagtgat    540

gtggacaaac tatttatcca gttggtacaa acctacaatc aattatttga agaaaaccct    600

attaacgcaa gtggagtaga tgctaaagcg attctttctg cacgattgag taaatcaaga    660

cgattagaaa atctcattgc tcagctcccc ggtgagaaga aaaatggctt atttgggaat    720

ctcattgctt tgtcattggg tttgacccct aattttaaat caaattttga tttggcagaa    780

gatgctaaat tacagctttc aaaagatact tacgatgatg atttagataa tttattggcg    840

caaattggag atcaatatgc tgatttgttt ttggcagcta agaatttatc agatgctatt    900

ttactttcag atatcctaag agtaaatact gaaataacta aggctcccct atcagcttca    960

atgattaaac gctacgatga acatcatcaa gacttgactc ttttaaaagc tttagttcga   1020

caacaacttc cagaaaagta taaagaaatc ttttttgatc aatcaaaaaa cggatatgca   1080

ggttatattg atgggggagc tagccaagaa gaattttata aatttatcaa accaatttta   1140
```

-continued

```
gaaaaaatgg atggtactga ggaattattg gtgaaactaa atcgtgaaga tttgctgcgc   1200
aagcaacgga cctttgacaa cggctctatt ccccatcaaa ttcacttggg tgagctgcat   1260
gctattttga gaagacaaga agacttttat ccatttttaa aagacaatcg tgagaagatt   1320
gaaaaaatct tgacttttcg aattccttat tatgttggtc cattggcgcg tggcaatagt   1380
cgttttgcat ggatgactcg gaagtctgaa gaaacaatta ccccatggaa ttttgaagaa   1440
gttgtcgata aaggtgcttc agctcaatca tttattgaac gcatgacaaa ctttgataaa   1500
aatcttccaa atgaaaaagt actaccaaaa catagtttgc tttatgagta ttttacggtt   1560
tataacgaat tgacaaaggt caaatatgtt actgaaggaa tgcgaaaacc agcatttctt   1620
tcaggtgaac agaagaaagc cattgttgat ttactcttca aaacaaatcg aaaagtaacc   1680
gttaagcaat taaaagaaga ttatttcaaa aaaatagaat gttttgatag tgttgaaatt   1740
tcaggagttg aagatagatt taatgcttca ttaggtacct accatgattt gctaaaaatt   1800
attaaagata aagatttttt ggataatgaa gaaaatgaag atatcttaga ggatattgtt   1860
ttaacattga ccttatttga agatagggag atgattgagg aaagacttaa aacatatgct   1920
cacctctttg atgataaggt gatgaaacag cttaaacgtc gccgttatac tggttgggga   1980
cgtttgtctc gaaaattgat taatggtatt agggataagc aatctggcaa aacaatatta   2040
gatttttga aatcagatgg ttttgccaat cgcaatttta tgcagctgat ccatgatgat   2100
agtttgacat ttaaagaaga cattcaaaaa gcacaagtgt ctggacaagg cgatagttta   2160
catgaacata ttgcaaattt agctggtagc cctgctatta aaaaaggtat tttacagact   2220
gtaaaagttg ttgatgaatt ggtcaaagta atggggcggc ataagccaga aaatatcgtt   2280
attgaaatgg cacgtgaaaa tcagacaact caaaagggcc agaaaaattc gcgagagcgt   2340
atgaaacgaa tcgaagaagg tatcaaagaa ttaggaagtc agattcttaa agagcatcct   2400
gttgaaaata ctcaattgca aaatgaaaag ctctatctct attatctcca aaatggaaga   2460
gacatgtatg tggaccaaga attagatatt aatcgtttaa gtgattatga tgtcgatcac   2520
attgttccac aaagtttcct taaagacgat tcaatagaca ataaggtctt aacgcgttct   2580
gataaaaatc gtggtaaatc ggataacgtt ccaagtgaag aagtagtcaa aaagatgaaa   2640
aactattgga gacaacttct aaacgccaag ttaatcactc aacgtaagtt tgataattta   2700
acgaaagctg aacgtggagg tttgagtgaa cttgataaag ctggttttat caaacgccaa   2760
ttggttgaaa ctcgccaaat cactaagcat gtggcacaaa ttttggatag tcgcatgaat   2820
actaaatacg atgaaaatga taaacttatt cgagaggtta aagtgattac cttaaaatct   2880
aaattagttt ctgacttccg aaaagatttc caattctata aagtacgtga gattaacaat   2940
taccatcatg cccatgatgc gtatctaaat gccgtcgttg gaactgcttt gattaagaaa   3000
tatccaaaac ttgaatcgga gtttgtctat ggtgattata aagtttatga tgttcgtaaa   3060
atgattgcta agtctgagca agaaataggc aaagcaaccg caaaatattt cttttactct   3120
aatatcatga acttcttcaa aacagaaatt acacttgcaa atggagagat tcgcaaacgc   3180
cctctaatcg aaactaatgg ggaaactgga gaaattgtct gggataaagg gcgagatttt   3240
gccacagtgc gcaaagtatt gtccatgccc caagtcaata ttgtcaagaa aacagaagta   3300
cagacaggcg gattctccaa ggagtcaatt ttaccaaaaa gaaattcgga caagcttatt   3360
gctcgtaaaa aagactggga tccaaaaaaa tatggtggtt ttgatagtcc aacggtagct   3420
tattcagtcc tagtggttgc taaggtggaa aaagggaaat cgaagaagtt aaaatccgtt   3480
```

aaagagttac tagggatcac aattatggaa agaagttcct ttgaaaaaaa tccgattgac 3540
tttttagaag ctaaaggata taaggaagtt aaaaaagact taatcattaa actacctaaa 3600
tatagtcttt ttgagttaga aaacggtcgt aaacggatgc tggctagtgc cggagaatta 3660
caaaaaggaa atgagctggc tctgccaagc aaatatgtga attttttata tttagctagt 3720
cattatgaaa agttgaaggg tagtccagaa gataacgaac aaaaacaatt gtttgtggag 3780
cagcataagc attatttaga tgagattatt gagcaaatca gtgaattttc taagcgtgtt 3840
attttagcag atgccaattt agataaagtt cttagtgcat ataacaaaca tagagacaaa 3900
ccaatacgtg aacaagcaga aaatattatt catttattta cgttgacgaa tcttggagct 3960
cccgctgctt ttaaatattt tgatacaaca attgatcgta aacgatatac gtctacaaaa 4020
gaagttttag atgccactct tatccatcaa tccatcactg gtctttatga aacacgcatt 4080
gatttgagtc agctaggagg tgactga 4107

<210> SEQ ID NO 3
<211> LENGTH: 630
<212> TYPE: DNA
<213> ORGANISM: clostridium

<400> SEQUENCE: 3
atgagtaaag ttacacaaat atcacatcca cttatattac acaaattagc atttatgaga 60
gataaaaaaa caggatctaa agattttaga gagatggtag aagaagtagc aatgctaatg 120
gcatatgaag taacaagaga aatgcagctt gaaactgttg aaatagaaac tcctatatgt 180
ataactaaat gtaaaatgtt agcaggaaaa aaggtagcta tagttcctat acttagagca 240
ggacttggaa tggtaaatgg agtattaaaa ttaatacctg ctgctaaggt tggacatata 300
ggattatata gagatgaaaa gacattaaaa cctgtagaat acttctgtaa acttcctcaa 360
gatatagagg aaagagacat aatagtaact gatccaatgc ttgcaactgg tgggtcagca 420
atagatgcaa taacacttct taagaaaaga ggagcaaaat acataagact tatgtgtctt 480
ataggagcac cagaaggtat agcagcagta caagaagcac atccagatgt agatatatac 540
ctcgcatcaa tagatgaaaa gttagatgaa aatggatata tagttcctgg tcttggagat 600
gctggagata gattattcgg tacaaaataa 630

<210> SEQ ID NO 4
<211> LENGTH: 2589
<212> TYPE: DNA
<213> ORGANISM: clostridium

<400> SEQUENCE: 4
atgaaagtca caacagtaaa ggaattagat gaaaaactca aggtaattaa agaagctcaa 60
aaaaaattct cttgttactc gcaagaaatg gttgatgaaa tctttagaaa tgcagcaatg 120
gcagcaatcg acgcaaggat agagctagca aaagcagctg ttttggaaac cggtatgggc 180
ttagttgaag acaaggttat aaaaaatcat tttgcaggcg aatacatcta taacaaatat 240
aaggatgaaa aaacctgcgg tataattgaa cgaaatgaac cctacggaat tacaaaaata 300
gcagaaccta taggagttgt agctgctata atccctgtaa caaaccccac atcaacaaca 360
atatttaaat ccttaatatc ccttaaaact agaaatggaa ttttcttttc gcctcaccca 420
agggcaaaaa aatccacaat actagcagct aaaacaatac ttgatgcagc cgttaagagt 480
ggtgccccgg aaaatataat aggttggata gatgaacctt caattgaact aactcaatat 540
ttaatgcaaa aagcagatat aacccttgca actggtggtc cctcactagt taaatctgct 600

-continued

```
tattcttccg gaaaaccagc aataggtgtt ggtccgggta acaccccagt aataattgat    660
gaatctgctc atataaaaat ggcagtaagt tcaattatat tatccaaaac ctatgataat    720
ggtgttatat gtgcttctga acaatctgta atagtcttaa aatccatata taacaaggta    780
aaagatgagt tccaagaaag aggagcttat ataataaaga aaaacgaatt ggataaagtc    840
cgtgaagtga tttttaaaga tggatccgta aaccctaaaa tagtcggaca gtcagcttat    900
actatagcag ctatggctgg cataaaagta cctaaaacca caagaatatt aataggagaa    960
gttacctcct taggtgaaga agaacctttt gcccacgaaa aactatctcc tgttttggct   1020
atgtatgagg ctgacaattt tgatgatgct ttaaaaaaag cagtaactct aataaactta   1080
ggaggcctcg gccatacctc aggaatatat gcagatgaaa taaaagcacg agataaaata   1140
gatagattta gtagtgccat gaaaaccgta agaacctttg taaatatccc aacctcacaa   1200
ggtgcaagtg gagatctata taattttaga ataccacctt ctttcacgct tggctgcgga   1260
ttttggggag gaaattctgt ttccgagaat gttggtccaa aacatctttt gaatattaaa   1320
accgtagctg aaaggagaga aaacatgctt tggtttagag ttccacataa agtatatttt   1380
aagttcggtt gtcttcaatt tgctttaaaa gatttaaaag atctaaagaa aaaaagagcc   1440
tttatagtta ctgatagtga cccctataat ttaaactatg ttgattcaat aataaaaata   1500
cttgagcacc tagatattga ttttaaagta tttaataagg ttggaagaga agctgatctt   1560
aaaaccataa aaaaagcaac tgaagaaatg tcctccttta tgccagacac tataatagct   1620
ttaggtggta cccctgaaat gagctctgca aagctaatgt gggtactata tgaacatcca   1680
gaagtaaaat ttgaagatct tgcaataaaa tttatggaca taagaaagag aatatatact   1740
ttcccaaaac tcggtaaaaa ggctatgtta gttgcaatta caacttctgc tggttccggt   1800
tctgaggtta ctccttttgc tttagtaact gacaataaca ctggaaataa gtacatgtta   1860
gcagattatg aaatgacacc aaatatggca attgtagatg cagaacttat gatgaaaatg   1920
ccaaagggat taaccgctta ttcaggtata gatgcactag taaatagtat agaagcatac   1980
acatccgtat atgcttcaga atacacaaac ggactagcac tagaggcaat acgattaata   2040
tttaaatatt tgcctgaggc ttacaaaaac ggaagaacca atgaaaaagc aagagagaaa   2100
atggctcacg cttcaactat ggcaggtatg gcatccgcta atgcatttct aggtctatgt   2160
cattccatgg caataaaatt aagttcagaa cacaatattc ctagtggcat tgccaatgca   2220
ttactaatag aagaagtaat aaaatttaac gcagttgata atcctgtaaa acaagcccct   2280
tgcccacaat ataagtatcc aaacaccata tttagatatg ctcgaattgc agattatata   2340
aagcttggag gaaatactga tgaggaaaag gtagatctct taattaacaa aatacatgaa   2400
ctaaaaaaag ctttaaatat accaacttca ataaaggatg caggtgtttt ggaggaaaac   2460
ttctattcct cccttgatag aatatctgaa cttgcactag atgatcaatg cacaggcgct   2520
aatcctagat ttcctcttac aagtgagata aaagaaatgt atataaattg ttttaaaaaa   2580
caaccttaa                                                           2589
```

<210> SEQ ID NO 5
<211> LENGTH: 10469
<212> TYPE: DNA
<213> ORGANISM: Artificial Sequence
<220> FEATURE:
<223> OTHER INFORMATION: plasmid

<400> SEQUENCE: 5

-continued

```
catggataaa aagtacagta ttggtctaga cataggaact aactctgttg ggtgggctgt     60
tataacagat gaatataaag ttccatcaaa aaaatttaaa gtattaggaa acactgatag    120
acattcaata aaaaaaaact tgataggtgc tttattattc gattcaggag agactgctga    180
agctacacgt ttaaaaagaa cagctagacg tagatataca agaagaaaaa ataggatatg    240
ttatcttcaa gaaattttta gtaatgaaat ggcaaaagtt gatgattcat tctttcacag    300
actagaagaa agtttcttag ttgaagaaga taagaagcat gaaagacacc ctatttttgg    360
taatatcgta gatgaagtag catatcatga gaagtatcca actatctatc atttaagaaa    420
gaaattagtt gattctacag ataaagctga tctgagatta atatatttag ctttagctca    480
tatgattaaa tttagaggac attttttaat agaaggtgat ttaaacccag acaacagcga    540
tgtagataaa ttatttatcc aattagttca aacttataat caattattcg aagagaatcc    600
aattaatgca agtggtgtag acgctaaggc tatattatca gctagattat caaaatctag    660
aagattagaa aatctaatag ctcaacttcc tggagaaaag aaaaatggac tttttgggaa    720
cctaatagct ctctcactcg gactaacacc aaattttaaa agcaattttg atcttgctga    780
agacgcaaag ttacaactat caaaggatac atacgatgat gatttagata atttgttagc    840
tcaaataggt gatcaatatg ctgatttgtt tcttgcagca aaaaacttaa gtgatgcaat    900
tttactatca gatatactta gagtaaatac agaaataaca aaggctcctt tatcagcaag    960
tatgattaaa cgatatgatg agcatcatca agatttaaca ttattaaagg cacttgtaag   1020
acaacaatta ccagaaaaat ataaagaaat tttctttgat caatctaaaa atggatatgc   1080
tggatatata gacggtggag caagtcaaga agagttttat aaatttataa agcctatttt   1140
agaaaaaatg gatggaactg aagaattact tgttaaactt aacagagaag atttacttag   1200
aaaacaaaga acttttgata atggttcaat tcctcaccaa attcatttag gagaattaca   1260
tgctatacta agaagacaag aagatttttta tccatttctt aaagataata gagaaaaaat   1320
tgaaaaaatt ttaactttta gaataccata ttatgtagga ccacttgcaa ggggaaattc   1380
aagatttgca tggatgacta gaaaatcaga agaaactata accccgtgga attttgaaga   1440
agtagtagat aaaggagcta gtgctcaatc atttatagaa agaatgacaa attttgataa   1500
gaatcttcct aacgaaaagg ttttgccaaa gcatagcctt ctttatgagt attttacagt   1560
ttataatgag cttactaaag taaaatacgt tacagaagga atgagaaaac cagcattttt   1620
gtctggtgaa caaaagaaag caatagtaga cctattattt aaaacaaata ggaaggttac   1680
cgtaaagcaa cttaaagaag attacttcaa aaaaattgaa tgctttgata gtgttgaaat   1740
atcaggagtt gaagatagat ttaatgcttc acttggtaca tatcacgatc tcttaaaaat   1800
tataaaagat aaggattttt tagataatga agaaaatgaa gatattcttg aagatatagt   1860
attaacattg acacttttg aagatagaga aatgatagaa gaaagattaa aaacatatgc   1920
acatcttttt gatgataagg ttatgaagca acttaaaaga agaagatata caggttgggg   1980
acgtttgtca agaaagctaa ttaatggtat tagagataaa caatcaggaa agactattct   2040
cgattttctt aaatcagatg gatttgctaa tagaaacttt atgcaattaa ttcatgatga   2100
ttctcttact ttcaaagagg atattcaaaa ggctcaagtt tctggacaag gcgatagctt   2160
acacgaacac attgctaacc ttgcagggag ccccgctatc aaaaaaggaa ttttacaaac   2220
agttaaagtt gtagatgaac ttgttaaagt tatgggaaga cacaaacctg agaatatagt   2280
tatagaaatg gccagagaaa atcaaacaac acaaaaagga caaaaaaatt ctagagagag   2340
aatgaagaga attgaagaag gaataaaaga gctaggatca caaatattaa aagaacatcc   2400
```

-continued

```
agttgaaaat actcaattgc aaaatgaaaa gttatatttg tattacttac aaaatggaag   2460
agatatgtat gttgatcaag aactcgatat taatagatta agtgactatg atgttgatca   2520
tattgttcct caatcatttt taaaagatga ttcaatcgat aacaaagtat taactagatc   2580
agataaaaat agaggaaagt cagataatgt accatctgaa gaagttgtta aaaaaatgaa   2640
gaactattgg agacaacttt taaatgcaaa gctaattaca caaagaaaat ttgacaattt   2700
aacaaaagca gaaagaggag gattaagcga attagacaaa gctggattta taaaaagaca   2760
acttgttgag acaagacaaa taactaagca tgttgctcaa atacttgatt caagaatgaa   2820
tacaaaatat gatgaaaatg ataaattaat cagagaagta aaagtaataa cattaaagtc   2880
aaaattagta tcagatttca gaaaggattt tcaattttac aaagttcgtg aaataaataa   2940
ctatcatcat gctcatgatg catacttaaa tgctgttgta ggaactgctc ttattaagaa   3000
atatcctaaa ctagaaagcg aatttgttta tggagattat aaagtttatg atgtgcgcaa   3060
aatgatcgcg aaatccgaac aagaaatcgg taaggctaca gcaaaatatt tcttttatag   3120
taatataatg aattttttta agacagaaat aactttggct aatggtgaaa tcagaaaaag   3180
accacttatc gaaacaaatg gagagacagg agaaatagta tgggataaag gaagagattt   3240
tgctactgtt agaaaagtac taagtatgcc acaagtaaat atcgtaaaga aaactgaagt   3300
tcaaactgga ggtttctcta aggaatcaat tttacctaag agaaattcag ataagttaat   3360
tgcaaggaaa aaagattggg acccaaaaaa atacggtggt tttgatagtc caacagttgc   3420
ctatagtgtt cttgtagtag cgaaagttga gaaaggtaag tcaaaaaagt tgaaaagcgt   3480
aaaagaactt cttggtatca caattatgga aagatcttca tttgaaaaaa atccaattga   3540
ctttttagaa gctaagggtt ataaagaagt taaaaaggat ttaatcataa aactaccaaa   3600
gtatagtcta tttgaactcg aaaacggaag aaaacgaatg ctcgctagcg caggagaact   3660
tcaaaaagga aatgaacttg cgctgccatc aaagtatgta aatttcttat atttagcttc   3720
tcattatgag aaattaaaag gatcaccaga ggataatgaa caaaagcaac tatttgtaga   3780
acaacacaaa cattatttag atgaaataat agaacaaata tctgaatttt ctaaaagagt   3840
tatacttgcc gacgcaaatc tagataaggt gctttcagcg tataataaac acagagataa   3900
accaataaga gaacaagcag aaaacattat ccatcttttt acattaacta atcttggtgc   3960
accagctgca tttaagtact ttgatacaac aatagataga aaaagataca catctactaa   4020
agaagtatta gacgcaactt taatacatca atctattaca gggctttatg aaacaagaat   4080
tgatttaagt caactaggcg gagattaagt cgacaaagta ttgttaaaaa taactctgta   4140
gaattataaa ttagttctac agagttattt tttgacccgg gtaccgagct cgaattcgta   4200
atcatggtca tagctgtttc ctgtgtgaaa ttgttatccg ctcacaattc cacacaacat   4260
acgagccgga agcataaagt gtaaagcctg gggtgcctaa tgagtgagct aactcacatt   4320
aattgcgttg cgctcactgc ccgctttcca gtcgggaaac ctgtcgtgcc agctgcatta   4380
atgaatcggc caacgcgcgg ggagaggcgg tttgcgtatt gggcgctctt ccgcttcctc   4440
gctcactgac tcgctgcgct cggtcgttcg gctgcggcga gcggtatcag ctcactcaaa   4500
ggcggtaata cggttatcca cagaatcagg ggataacgca ggaaagaaca tgtgagcaaa   4560
aggccagcaa aaggccagga accgtaaaaa ggccgcgttg ctggcgtttt tccataggct   4620
ccgcccccct gacgagcatc acaaaaatcg acgctcaagt cagaggtggc gaaacccgac   4680
aggactataa agataccagg cgtttccccc tggaagctcc ctcgtgcgct ctcctgttcc   4740
```

```
gaccctgccg cttaccggat acctgtccgc ctttctccct tcgggaagcg tggcgctttc   4800
tcatagctca cgctgtaggt atctcagttc ggtgtaggtc gttcgctcca agctgggctg   4860
tgtgcacgaa ccccccgttc agcccgaccg ctgcgcctta tccggtaact atcgtcttga   4920
gtccaacccg gtaagacacg acttatcgcc actggcagca gccactggta acaggattag   4980
cagagcgagg tatgtaggcg gtgctacaga gttcttgaag tggtggccta actacggcta   5040
cactagaagg acagtatttg gtatctgcgc tctgctgaag ccagttacct tcggaaaaag   5100
agttggtagc tcttgatccg gcaaacaaac caccgctggt agcggtggtt tttttgtttg   5160
caagcagcag attacgcgca gaaaaaaagg atctcaagaa gatcctttga tcttttctac   5220
ggggtctgac gctcagtgga acgaaaactc acgttaaggg attttggtca tgagattatc   5280
aaaaaggatc ttcacctaga tccttttaaa ttaaaaatga agttttaaat caatctaaag   5340
tatatatgag taaacttggt ctgacagtta ccaatgctta atcagtgagg cacctatctc   5400
agcgatctgt ctatttcgtt catccatagt tgcctgactc cccgtcgtgt agataactac   5460
gatacgggag ggcttaccat ctggccccag tgctgcaatg ataccgcgag acccacgctc   5520
accggctcca gatttatcag caataaacca gccagccgga agggccgagc gcagaagtgg   5580
tcctgcaact ttatccgcct ccatccagtc tattaattgt tgccgggaag ctagagtaag   5640
tagttcgcca gttaatagtt tgcgcaacgt tgttgccatt gctacaggca tcgtggtgtc   5700
acgctcgtcg tttggtatgg cttcattcag ctccggttcc caacgatcaa ggcgagttac   5760
atgatccccc atgttgtgca aaaaagcggt tagctccttc ggtcctccga tcgttgtcag   5820
aagtaagttg gccgcagtgt tatcactcat ggttatggca gcactgcata attctcttac   5880
tgtcatgcca tccgtaagat gcttttctgt gactggtgag tactcaacca agtcattctg   5940
agaatagtgt atgcggcgac cgagttgctc ttgcccggcg tcaatacggg ataataccgc   6000
gccacatagc agaactttaa aagtgctcat cattggaaaa cgttcttcgg ggcgaaaact   6060
ctcaaggatc ttaccgctgt tgagatccag ttcgatgtaa cccactcgtg cacccaactg   6120
atcttcagca tcttttactt tcaccagcgt ttctgggtga gcaaaaacag gaaggcaaaa   6180
tgccgcaaaa aagggaataa gggcgacacg gaaatgttga atactcatac tcttcctttt   6240
tcaatattat tgaagcattt atcagggtta ttgtctcatg agcggataca tatttgaatg   6300
tatttagaaa aataaacaaa taggggttcc gcgcacattt ccccgaaaag tgccacctga   6360
ctgccgggcc tcttgcggga tcaaaagaaa aacgaaatga tacaccaatc agtgcaaaaa   6420
aagatataat gggagataag acggttcgtg ttcgtgctga cttgcaccat atcataaaaa   6480
tcgaaacagc aaagaatggc ggaaacgtaa aagaagttat ggaaataaga cttagaagca   6540
aacttaagag tgtgttgata gtgcagtatc ttaaaatttt gtataatagg aattgaagtt   6600
aaattagatg ctaaaaattt gtaattaaga aggagtgatt acatgaacaa aaatataaaa   6660
tattctcaaa actttttaac gagtgaaaaa gtactcaacc aaataataaa acaattgaat   6720
ttaaaagaaa ccgataccgt ttacgaaatt ggaacaggta aagggcattt aacgacgaaa   6780
ctggctaaaa taagtaaaca ggtaacgtct attgaattag acagtcatct attcaactta   6840
tcgtcagaaa aattaaaact gaatactcgt gtcactttaa ttcaccaaga tattctacag   6900
tttcaattcc ctaacaaaca gaggtataaa attgttggga gtattcctta ccatttaagc   6960
acacaaatta ttaaaaaagt ggtttttgaa agccatgcgt ctgacatcta tctgattgtt   7020
gaagaaggat tctacaagcg taccttggat attcaccgaa cactagggtt gctcttgcac   7080
actcaagtct cgattcagca attgcttaag ctgccagcgg aatgctttca tcctaaacca   7140
```

```
aaagtaaaca gtgtcttaat aaaacttacc cgccatacca cagatgttcc agataaatat   7200
tggaagctat atacgtactt tgtttcaaaa tgggtcaatc gagaatatcg tcaactgttt   7260
actaaaaatc agtttcatca agcaatgaaa cacgccaaag taaacaattt aagtaccgtt   7320
acttatgagc aagtattgtc tatttttaat agttatctat tatttaacgg gaggaaataa   7380
ttctatgagt ccctaggccc aactaactca acgctagtag tggatttaat cccaaatgag   7440
ccaacagaac cagaaccaga aacagaatca gaacaagtaa cattggattt agaaatggaa   7500
gaagaaaaaa gcaatgactt cgtgtgaata atgcacgaaa tcgttgctta ttttttttta   7560
aaagcggtat actagatata acgaaacaac gaactgaata gaaacgaaaa aagagccatg   7620
acacatttat aaaatgtttg acgacatttt ataaatgcat agcccgataa gattgccaaa   7680
ccaacgctta tcagttagtc agatgaactc ttccctcgta agaagttatt taattaactt   7740
tgtttgaaga cggtatataa ccgtactatc attatatagg gaaatcagag agttttcaag   7800
tatctaagct actgaattta agaattgtta agcaatcaat cggaaatcgt ttgattgctt   7860
tttttgtatt catttataga aggtggagtt tgtatgaatc atgatgaatg taaaacttat   7920
ataaaaaata gtttattgga gataagaaaa ttagcaaata tctatacact agaaacgttt   7980
aagaaagagt tagaaaagag aaatatctac ttagaaacaa aatcagataa gtatttttct   8040
tcggaggggg aagattatat atataagtta atagaaaata acaaaataat ttattcgatt   8100
agtggaaaaa aattgactta taaaggaaaa aaatcttttt caaaacatgc aatattgaaa   8160
cagttgaatg aaaaagcaaa ccaagttaat taaacaacct attttatagg atttatagga   8220
aaggagaaca gctgaatgaa tatccctttt gttgtagaaa ctgtgcttca tgacggcttg   8280
ttaaagtaca aatttaaaaa tagtaaaatt cgctcaatca ctaccaagcc aggtaaaagc   8340
aaaggggcta tttttgcgta tcgctcaaaa tcaagcatga ttggcggtcg tggtgttgtt   8400
ctgacttccg aggaagcgat tcaagaaaat caagatacat ttacacattg gacacccaac   8460
gtttatcgtt atggaacgta tgcagacgaa aaccgttcat acacgaaagg acattctgaa   8520
aacaatttaa gacaaatcaa taccttcttt attgattttg atattcacac ggcaaaagaa   8580
actatttcag caagcgatat tttaacaacc gctattgatt taggttttat gcctactatg   8640
attatcaaat ctgataaagg ttatcaagca tattttgttt tagaaacgcc agtctatgtg   8700
acttcaaaat cagaatttaa atctgtcaaa gcagccaaaa taatttcgca aaatatccga   8760
gaatattttg gaaagtcttt gccagttgat ctaacgtgta atcattttgg tattgctcgc   8820
ataccaagaa cggacaatgt agaatttttt gatcctaatt accgttattc tttcaaagaa   8880
tggcaagatt ggtctttcaa acaaacagat aataagggct ttactcgttc aagtctaacg   8940
gttttaagcg gtacagaagg caaaaaacaa gtagatgaac cctggtttaa tctcttattg   9000
cacgaaacga aattttcagg agaaaagggt ttaatagggc gtaataacgt catgtttacc   9060
ctctctttag cctactttag ttcaggctat tcaatcgaaa cgtgcgaata taatatgttt   9120
gagtttaata atcgattaga tcaaccctta gaagaaaaag aagtaatcaa aattgttaga   9180
agtgcctatt cagaaaacta tcaaggggct aatagggaat acattaccat tctttgcaaa   9240
gcttgggtat caagtgattt aaccagtaaa gatttatttg tccgtcaagg gtggtttaaa   9300
ttcaagaaaa aaagaagcga acgtcaacgt gttcatttgt cagaatggaa agaagattta   9360
atggcttata ttagcgaaaa aagcgatgta tacaagcctt atttagtgac gaccaaaaaa   9420
gagattagag aagtgctagg cattcctgaa cggacattag ataaattgct gaaggtactg   9480
```

-continued

```
aaggcgaatc aggaaatttt ctttaagatt aaaccaggaa gaaatggtgg cattcaactt   9540

gctagtgtta aatcattgtt gctatcgatc attaaagtaa aaaaagaaga aaaagaaagc   9600

tatataaagg cgctgacaaa ttcttttgac ttagagcata cattcattca agagacttta   9660

aacaagctag cagaacgccc taaaacggac acacaactcg atttgtttag ctatgataca   9720

ggctgaaaat aaaacccgca ctatgccatt acatttatat ctatgatacg tgtttgtttt   9780

ttctttgctg tttagcgaat gattagcaga aatatacaga gtaagatttt aattaattat   9840

tagggggaga aggagagagt agcccgaaaa cttttagttg gcttggactg aacgaagtga   9900

gggaaaggct actaaaacgt cgaggggcag tgagagcgaa gcgaacactt gatttttttaa   9960

ttttctatct tttataggtc attagagtat acttatttgt cctataaact atttagcagc  10020

ataatagatt tattgaatag gtcatttaag ttgagcatat tagaggagga aaatcttgga  10080

gaaatatttg aagaacccga ttacatggat tggattagtt cttgtggtta cgtggttttt  10140

aactaaaagt agtgaatttt tgatttttgg tgtgtgtgtc ttgttgttag tatttgctag  10200

tcaaagtgat taaatagaat tctagcgcca ttcgccattc aggctgcgca actgttggga  10260

agggcgatcg gtgcgggcct cttcgctatt acgccagctg gcgaaagggg gatgtgctgc  10320

aaggcgatta agttgggtaa cgccagggtt ttcccagtca cgacgttgta aaacgacggc  10380

cagtgccaag cttgcatgcc tgcaggcctc gagtatattg ataaaaataa taatagtggg  10440

tataattaag ttgttaggag gttagttac                                  10469
```

<210> SEQ ID NO 6
<211> LENGTH: 8876
<212> TYPE: DNA
<213> ORGANISM: Artificial Sequence
<220> FEATURE:
<223> OTHER INFORMATION: plasmid

<400> SEQUENCE: 6

```
tcgagactct atcattgata gagtttgaaa ctctatcatt gatagagtat aatatctttg     60

ttcattagag cgataaactt gaatttgaga gggaacttcc atggataaaa agtacagtat    120

tggtctagac ataggaacta actctgttgg gtgggctgtt ataacagatg aatataaagt    180

tccatcaaaa aaatttaaag tattaggaaa cactgataga cattcaataa aaaaaaactt    240

gataggtgct ttattattcg attcaggaga gactgctgaa gctacacgtt taaaaagaac    300

agctagacgt agatatacaa gaagaaaaaa taggatatgt tatcttcaag aaatttttag    360

taatgaaatg gcaaaagttg atgattcatt ctttcacaga ctagaagaaa gtttcttagt    420

tgaagaagat aagaagcatg aaagacaccc tatttttggt aatatcgtag atgaagtagc    480

atatcatgag aagtatccaa ctatctatca tttaagaaag aaattagttg attctacaga    540

taaagctgat ctgagattaa tatatttagc tttagctcat atgattaaat ttagaggaca    600

ttttttaata gaaggtgatt taaacccaga caacagcgat gtagataaat tatttatcca    660

attagttcaa acttataatc aattattcga agagaatcca attaatgcaa gtggtgtaga    720

cgctaaggct atattatcag ctagattatc aaaatctaga agattagaaa atctaatagc    780

tcaacttcct ggagaaaaga aaaatggact ttttgggaac ctaatagctc tctcactcgg    840

actaacacca aattttaaaa gcaattttga tcttgctgaa gacgcaaagt tacaactatc    900

aaaggataca tacgatgatg atttagataa tttgttagct caaataggtg atcaatatgc    960

tgatttgttt cttgcagcaa aaaacttaag tgatgcaatt ttactatcag atatacttag   1020

agtaaataca gaaataacaa aggctccttt atcagcaagt atgattaaac gatatgatga   1080
```

-continued gcatcatcaa gatttaacat tattaaaggc acttgtaaga caacaattac cagaaaaata 1140
taaagaaatt ttctttgatc aatctaaaaa tggatatgct ggatatatag acggtggagc 1200
aagtcaagaa gagttttata aatttataaa gcctatttta gaaaaaatgg atggaactga 1260
agaattactt gttaaactta acagagaaga tttacttaga aaacaaagaa cttttgataa 1320
tggttcaatt cctcaccaaa ttcatttagg agaattacat gctatactaa gaagacaaga 1380
agatttttat ccatttctta aagataatag agaaaaaatt gaaaaaattt taacttttag 1440
aataccatat tatgtaggac cacttgcaag gggaaattca agatttgcat ggatgactag 1500
aaaatcagaa gaaactataa ccccgtggaa ttttgaagaa gtagtagata aaggagctag 1560
tgctcaatca tttatagaaa gaatgacaaa ttttgataag aatcttccta acgaaaaggt 1620
tttgccaaag catagccttc tttatgagta ttttacagtt tataatgagc ttactaaagt 1680
aaaatacgtt acagaaggaa tgagaaaacc agcatttttg tctggtgaac aaaagaaagc 1740
aatagtagac ctattattta aaacaaatag gaaggttacc gtaaagcaac ttaaagaaga 1800
ttacttcaaa aaaattgaat gctttgatag tgttgaaata tcaggagttg aagatagatt 1860
taatgcttca cttggtacat atcacgatct cttaaaaatt ataaaagata aggatttttt 1920
agataatgaa gaaaatgaag atattcttga agatatagta ttaacattga cactttttga 1980
agatagagaa atgatagaag aaagattaaa aacatatgca catctttttg atgataaggt 2040
tatgaagcaa cttaaaagaa gaagatatac aggttgggga cgtttgtcaa gaaagctaat 2100
taatggtatt agagataaac aatcaggaaa gactattctc gattttctta aatcagatgg 2160
atttgctaat agaaacttta tgcaattaat tcatgatgat tctcttactt tcaaagagga 2220
tattcaaaag gctcaagttt ctggacaagg cgatagctta cacgaacaca ttgctaacct 2280
tgcagggagc cccgctatca aaaaaggaat tttacaaaca gttaaagttg tagatgaact 2340
tgttaaagtt atgggaagac acaaacctga gaatatagtt atagaaatgg ccagagaaaa 2400
tcaaacaaca caaaaaggac aaaaaaattc tagagagaga atgaagagaa ttgaagaagg 2460
aataaaagag ctaggatcac aaatattaaa agaacatcca gttgaaaata ctcaattgca 2520
aaatgaaaag ttatatttgt attacttaca aaatggaaga gatatgtatg ttgatcaaga 2580
actcgatatt aatagattaa gtgactatga tgttgatcat attgttcctc aatcattttt 2640
aaaagatgat tcaatcgata acaaagtatt aactagatca gataaaaata gaggaaagtc 2700
agataatgta ccatctgaag aagttgttaa aaaaatgaag aactattgga gacaactttt 2760
aaatgcaaag ctaattacac aaagaaaatt tgacaattta acaaaagcag aaagaggagg 2820
attaagcgaa ttagacaaag ctggatttat aaaaagacaa cttgttgaga caagacaaat 2880
aactaagcat gttgctcaaa tacttgattc aagaatgaat acaaaatatg atgaaaatga 2940
taaattaatc agagaagtaa aagtaataac attaaagtca aaattagtat cagatttcag 3000
aaaggatttt caattttaca aagttcgtga aataaataac tatcatcatg ctcatgatgc 3060
atacttaaat gctgttgtag gaactgctct tattaagaaa tatcctaaac tagaaagcga 3120
atttgtttat ggagattata aagtttatga tgtgcgcaaa atgatcgcga aatccgaaca 3180
agaaatcggt aaggctacag caaaatattt cttttatagt aatataatga atttttttaa 3240
gacagaaata actttggcta atggtgaaat cagaaaaaga ccacttatcg aaacaaatgg 3300
agagacagga gaaatagtat gggataaagg aagagatttt gctactgtta gaaaagtact 3360
aagtatgcca caagtaaata tcgtaaagaa aactgaagtt caaactggag gtttctctaa 3420

-continued

```
ggaatcaatt ttacctaaga gaaattcaga taagttaatt gcaaggaaaa aagattggga   3480
cccaaaaaaa tacggtggtt ttgatagtcc aacagttgcc tatagtgttc ttgtagtagc   3540
gaaagttgag aaaggtaagt caaaaaagtt gaaaagcgta aaagaacttc ttggtatcac   3600
aattatggaa agatcttcat ttgaaaaaaa tccaattgac tttttagaag ctaagggtta   3660
taaagaagtt aaaaaggatt taatcataaa actaccaaag tatagtctat ttgaactcga   3720
aaacggaaga aaacgaatgc tcgctagcgc aggagaactt caaaaaggaa atgaacttgc   3780
gctgccatca aagtatgtaa atttcttata tttagcttct cattatgaga aattaaaagg   3840
atcaccagag gataatgaac aaaagcaact atttgtagaa caacacaaac attatttaga   3900
tgaaataata gaacaaatat ctgaattttc taaaagagtt atacttgccg acgcaaatct   3960
agataaggtg ctttcagcgt ataataaaca cagagataaa ccaataagag aacaagcaga   4020
aaacattatc catcttttta cattaactaa tcttggtgca ccagctgcat ttaagtactt   4080
tgatacaaca atagatagaa aaagatacac atctactaaa gaagtattag acgcaacttt   4140
aatacatcaa tctattacag ggctttatga aacaagaatt gatttaagtc aactaggcgg   4200
agattaagtc gacaaagtat tgttaaaaat aactctgtag aattataaat tagttctaca   4260
gagttatttt ttgacccggg tatattgata aaaataataa tagtgggtat aattaagttg   4320
ttaggaggtt agttagaatg atgtcaagat tagataaaag taaagtgatt aacagcgcat   4380
tagagctgct taatgaggtc ggaatcgaag gtttaacaac ccgtaaactc gcccagaagc   4440
taggtgtaga gcagcctaca ttgtattggc atgtaaaaaa taagcgggct ttgctcgacg   4500
ccttagccat tgagatgtta gataggcacc atactcactt ttgcccttta gaaggggaaa   4560
gctggcaaga tttttacgt aataacgcta aaagttttag atgtgcttta ctaagtcatc   4620
gcgatggagc aaaagtacat ttaggtacac ggcctacaga aaaacagtat gaaactctcg   4680
aaaatcaatt agcctttta tgccaacaag gtttttcact agagaatgca ttatatgcac   4740
tcagcgctgt ggggcatttt actttaggtt gcgtattgga agatcaagag catcaagtcg   4800
ctaaagaaga aagggaaaca cctactactg atagtatgcc gccattatta cgacaagcta   4860
tcgaattatt tgatcaccaa ggtgcagagc cagccttctt attcggcctt gaattgatca   4920
tatgcggatt agaaaaacaa cttaaatgtg aaagtgggtc ttaaaagcag cataaccttt   4980
ttccgtgatg gtaacttcac ggtaaccaag atgtcgagtt gagctcgaat tcgtaatcat   5040
ggtcatagct gtttcctgtg tgaaattgtt atccgctcac aattccacac aacatacgag   5100
ccggaagcat aaagtgtaaa gcctggggtg cctaatgagt gagctaactc acattaattg   5160
cgttgcgctc actgcccgct ttccagtcgg gaaacctgtc gtgccagctg cattaatgaa   5220
tcggccaacg cgcggggaga ggcggtttgc gtattgggcg ctcttccgct tcctcgctca   5280
ctgactcgct gcgctcggtc gttcggctgc ggcgagcggt atcagctcac tcaaaggcgg   5340
taatacggtt atccacagaa tcaggggata acgcaggaaa gaacatgtga gcaaaaggcc   5400
agcaaaaggc caggaaccgt aaaaaggccg cgttgctggc gtttttccat aggctccgcc   5460
cccctgacga gcatcacaaa aatcgacgct caagtcagag gtggcgaaac ccgacaggac   5520
tataaagata ccaggcgttt ccccctggaa gctccctcgt gcgctctcct gttccgaccc   5580
tgccgcttac cggatacctg tccgcctttc tcccttcggg aagcgtggcg ctttctcata   5640
gctcacgctg taggtatctc agttcggtgt aggtcgttcg ctccaagctg ggctgtgtgc   5700
acgaaccccc cgttcagccc gaccgctgcg ccttatccgg taactatcgt cttgagtcca   5760
acccggtaag acacgactta tcgccactgg cagcagccac tggtaacagg attagcagag   5820
```

```
cgaggtatgt aggcggtgct acagagttct tgaagtggtg gcctaactac ggctacacta   5880
gaaggacagt atttggtatc tgcgctctgc tgaagccagt taccttcgga aaaagagttg   5940
gtagctcttg atccggcaaa caaaccaccg ctggtagcgg tggttttttt gtttgcaagc   6000
agcagattac gcgcagaaaa aaaggatctc aagaagatcc tttgatcttt tctacggggt   6060
ctgacgctca gtggaacgaa aactcacgtt aagggatttt ggtcatgaga ttatcaaaaa   6120
ggatcttcac ctagatcctt ttaaattaaa aatgaagttt taaatcaatc taaagtatat   6180
atgagtaaac ttggtctgac agttaccagg tccactgccg ggcctcttgc gggatcaaaa   6240
gaaaaacgaa atgatacacc aatcagtgca aaaaaagata taatgggaga taagacggtt   6300
cgtgttcgtg ctgacttgca ccatatcata aaaatcgaaa cagcaaagaa tggcggaaac   6360
gtaaaagaag ttatggaaat aagacttaga agcaaactta agagtgtgtt gatagtgcag   6420
tatcttaaaa ttttgtataa taggaattga agttaaatta gatgctaaaa atttgtaatt   6480
aagaaggagt gattacatga acaaaaatat aaaatattct caaaactttt taacgagtga   6540
aaaagtactc aaccaaataa taaaacaatt gaatttaaaa gaaaccgata ccgtttacga   6600
aattggaaca ggtaaagggc atttaacgac gaaactggct aaaataagta aacaggtaac   6660
gtctattgaa ttagacagtc atctattcaa cttatcgtca gaaaaattaa aactgaatac   6720
tcgtgtcact ttaattcacc aagatattct acagtttcaa ttccctaaca aacagaggta   6780
taaaattgtt gggagtattc cttaccattt aagcacacaa attattaaaa aagtggtttt   6840
tgaaagccat gcgtctgaca tctatctgat tgttgaagaa ggattctaca agcgtacctt   6900
ggatattcac cgaacactag ggttgctctt gcacactcaa gtctcgattc agcaattgct   6960
taagctgcca gcggaatgct ttcatcctaa accaaaagta aacagtgtct taataaaact   7020
tacccgccat accacagatg ttccagataa atattggaag ctatatacgt actttgtttc   7080
aaaatgggtc aatcgagaat atcgtcaact gtttactaaa aatcagtttc atcaagcaat   7140
gaaacacgcc aaagtaaaca atttaagtac cgttacttat gagcaagtat tgtctatttt   7200
taatagttat ctattattta acgggaggaa ataattctat gagtccctag gcaggcctcc   7260
gccattattt ttttgaacaa ttgacaattc atttcttatt ttttattaag tgatagtcaa   7320
aaggcataac agtgctgaat agaaagaaat ttacagaaaa gaaaattata gaatttagta   7380
tgattaatta tactcattta tgaatgttta attgaataca aaaaaaaata cttgttatgt   7440
attcaattac gggttaaaat atagacaagt tgaaaaattt aataaaaaaa taagtcctca   7500
gctcttatat attaagctac caacttagta tataagccaa aacttaaatg tgctaccaac   7560
acatcaagcc gttagagaac tctatctata gcaatatttc aaatgtaccg acatacaaga   7620
gaaacattaa ctatatatat tcaatttatg agattatctt aacagatata aatgtaaatt   7680
gcaataagta agatttagaa gtttatagcc tttgtgtatt ggaagcagta cgcaaaggct   7740
tttttatttg ataaaaatta gaagtatatt tattttttca taattaattt atgaaaatga   7800
aagggggtga gcaaagtgac agaggaaagc agtatcttat caaataacaa ggtattagca   7860
atatcattat tgactttagc agtaaacatt atgactttta tagtgcttgt agctaagtag   7920
tacgaaaggg ggagctttaa aaagctcctt ggaatacata gaattcataa attaatttat   7980
gaaaagaagg gcgtatatga aacttgtaa aaattgcaaa gagtttatta aagatactga   8040
aatatgcaaa atacattcgt tgatgattca tgataaaaca gtagcaacct attgcagtaa   8100
atacaatgag tcaagatgtt tacataaagg gaaagtccaa tgtattaatt gttcaaagat   8160
```

gaaccgatat ggatggtgtg ccataaaaat gagatgtttt acagaggaag aacagaaaaa 8220
agaacgtaca tgcattaaat attatgcaag gagctttaaa aaagctcatg taaagaagag 8280
taaaaagaaa aaataattta tttattaatt taatattgag agtgccgaca cagtatgcac 8340
taaaaaatat atctgtggtg tagtgagccg atacaaaagg atagtcactc gcattttcat 8400
aatacatctt atgttatgat tatgtgtcgg tgggacttca cgacgaaaac ccacaataaa 8460
aaaagagttc ggggtagggt taagcatagt tgaggcaact aaacaatcaa gctaggatat 8520
gcagtagcag accgtaaggt cgttgtttag gtgtgttgta atacatacgc tattaagatg 8580
taaaaatacg gataccaatg aagggaaaag tataattttt ggatgtagtt tgtttgttca 8640
tctatgggca aactacgtcc aaagccgttt ccaaatctgc taaaaagtat atcctttcta 8700
aaatcaaagt caagtatgaa atcataaata aagtttaatt ttgaagttat tatgatatta 8760
tgtttttcta ttaaaataaa ttaagtatat agaatagttt aataatagta tatacttaat 8820
gtgataagtg tctgacagtg tcacagaaag gatgattgtt atggattata agcggc 8876

<210> SEQ ID NO 7
<211> LENGTH: 8874
<212> TYPE: DNA
<213> ORGANISM: Artificial Sequence
<220> FEATURE:
<223> OTHER INFORMATION: plasmid

<400> SEQUENCE: 7
catggataaa aagtacagta ttggtctaga cataggaact aactctgttg ggtgggctgt 60
tataacagat gaatataaag ttccatcaaa aaaatttaaa gtattaggaa acactgatag 120
acattcaata aaaaaaaact tgataggtgc tttattattc gattcaggag agactgctga 180
agctacacgt ttaaaaagaa cagctagacg tagatataca agaagaaaaa ataggatatg 240
ttatcttcaa gaaattttta gtaatgaaat ggcaaaagtt gatgattcat tctttcacag 300
actagaagaa agtttcttag ttgaagaaga taagaagcat gaaagacacc ctatttttgg 360
taatatcgta gatgaagtag catatcatga gaagtatcca actatctatc atttaagaaa 420
gaaattagtt gattctacag ataaagctga tctgagatta atatatttag ctttagctca 480
tatgattaaa tttagaggac atttttttaat agaaggtgat ttaaacccag acaacagcga 540
tgtagataaa ttatttatcc aattagttca aacttataat caattattcg aagagaatcc 600
aattaatgca agtggtgtag acgctaaggc tatattatca gctagattat caaaatctag 660
aagattagaa aatctaatag ctcaacttcc tggagaaaag aaaaatggac tttttgggaa 720
cctaatagct ctctcactcg gactaacacc aaattttaaa agcaattttg atcttgctga 780
agacgcaaag ttacaactat caaaggatac atacgatgat gatttagata atttgttagc 840
tcaaataggt gatcaatatg ctgatttgtt tcttgcagca aaaaacttaa gtgatgcaat 900
tttactatca gatatactta gagtaaatac agaaataaca aaggctcctt tatcagcaag 960
tatgattaaa cgatatgatg agcatcatca agatttaaca ttattaaagg cacttgtaag 1020
acaacaatta ccagaaaaat ataaagaaat tttctttgat caatctaaaa atggatatgc 1080
tggatatata gacggtggag caagtcaaga agagttttat aaatttataa agcctatttt 1140
agaaaaaatg gatggaactg aagaattact tgttaaactt aacagagaag atttacttag 1200
aaaacaaaga actttgata atggttcaat tcctcaccaa attcatttag gagaattaca 1260
tgctatacta agaagacaag aagattttta tccatttctt aaagataata gagaaaaaat 1320
tgaaaaaatt ttaactttta gaataccata ttatgtagga ccacttgcaa ggggaaattc 1380

```
aagatttgca tggatgacta gaaaatcaga agaaactata accccgtgga attttgaaga   1440
agtagtagat aaaggagcta gtgctcaatc atttatagaa agaatgacaa attttgataa   1500
gaatcttcct aacgaaaagg ttttgccaaa gcatagcctt ctttatgagt attttacagt   1560
ttataatgag cttactaaag taaaatacgt tacagaagga atgagaaaac cagcattttt   1620
gtctggtgaa caaaagaaag caatagtaga cctattattt aaaacaaata ggaaggttac   1680
cgtaaagcaa cttaaagaag attacttcaa aaaaattgaa tgctttgata gtgttgaaat   1740
atcaggagtt gaagatagat ttaatgcttc acttggtaca tatcacgatc tcttaaaaat   1800
tataaaagat aaggattttt tagataatga agaaaatgaa gatattcttg aagatatagt   1860
attaacattg acactttttg aagatagaga aatgatagaa gaaagattaa aaacatatgc   1920
acatcttttt gatgataagg ttatgaagca acttaaaaga agaagatata caggttgggg   1980
acgtttgtca agaaagctaa ttaatggtat tagagataaa caatcaggaa agactattct   2040
cgatttttctt aaatcagatg gatttgctaa tagaaacttt atgcaattaa ttcatgatga   2100
ttctcttact ttcaaagagg atattcaaaa ggctcaagtt tctggacaag gcgatagctt   2160
acacgaacac attgctaacc ttgcagggag ccccgctatc aaaaaaggaa ttttacaaac   2220
agttaaagtt gtagatgaac ttgttaaagt tatgggaaga cacaaacctg agaatatagt   2280
tatagaaatg gccagagaaa atcaaacaac acaaaaagga caaaaaaatt ctagagagag   2340
aatgaagaga attgaagaag gaataaaaga gctaggatca caaatattaa aagaacatcc   2400
agttgaaaat actcaattgc aaaatgaaaa gttatatttg tattacttac aaaatggaag   2460
agatatgtat gttgatcaag aactcgatat taatagatta agtgactatg atgttgatca   2520
tattgttcct caatcatttt taaaagatga ttcaatcgat aacaaagtat taactagatc   2580
agataaaaat agaggaaagt cagataatgt accatctgaa gaagttgtta aaaaaatgaa   2640
gaactattgg agacaacttt taaatgcaaa gctaattaca caaagaaaat ttgacaattt   2700
aacaaaagca gaaagaggag gattaagcga attagacaaa gctggattta taaaaagaca   2760
acttgttgag acaagacaaa taactaagca tgttgctcaa atacttgatt caagaatgaa   2820
tacaaaatat gatgaaaatg ataaattaat cagagaagta aaagtaataa cattaaagtc   2880
aaaattagta tcagatttca gaaaggattt tcaattttac aaagttcgtg aaataaataa   2940
ctatcatcat gctcatgatg catacttaaa tgctgttgta ggaactgctc ttattaagaa   3000
atatcctaaa ctagaaagcg aatttgttta tggagattat aaagtttatg atgtgcgcaa   3060
aatgatcgcg aaatccgaac aagaaatcgg taaggctaca gcaaaatatt tcttttatag   3120
taatataatg aatttttta agacagaaat aactttggct aatggtgaaa tcagaaaaag   3180
accacttatc gaaacaaatg gagagacagg agaaatagta tgggataaag gaagagattt   3240
tgctactgtt agaaaagtac taagtatgcc acaagtaaat atcgtaaaga aaactgaagt   3300
tcaaactgga ggtttctcta aggaatcaat tttacctaag agaaattcag ataagttaat   3360
tgcaaggaaa aaagattggg acccaaaaaa atacggtggt tttgatagtc caacagttgc   3420
ctatagtgtt cttgtagtag cgaaagttga gaaaggtaag tcaaaaaagt tgaaaagcgt   3480
aaaagaactt cttggtatca caattatgga aagatcttca tttgaaaaaa atccaattga   3540
ctttttagaa gctaagggtt ataaagaagt taaaaaggat ttaatcataa aactaccaaa   3600
gtatagtcta tttgaactcg aaaacggaag aaaacgaatg ctcgctagcg caggagaact   3660
tcaaaaagga aatgaacttg cgctgccatc aaagtatgta aatttcttat atttagcttc   3720
```

-continued

```
tcattatgag aaattaaaag gatcaccaga ggataatgaa caaaagcaac tatttgtaga   3780
acaacacaaa cattatttag atgaaataat agaacaaata tctgaatttt ctaaaagagt   3840
tatacttgcc gacgcaaatc tagataaggt gctttcagcg tataataaac acagagataa   3900
accaataaga gaacaagcag aaaacattat ccatcttttt acattaacta atcttggtgc   3960
accagctgca tttaagtact ttgatacaac aatagataga aaaagataca catctactaa   4020
agaagtatta gacgcaactt taatacatca atctattaca gggctttatg aaacaagaat   4080
tgatttaagt caactaggcg gagattaagt cgacaaagta ttgttaaaaa taactctgta   4140
gaattataaa ttagttctac agagttattt tttgacccgg gtatattgat aaaaataata   4200
atagtgggta taattaagtt gttaggaggt tagttagaat gatgtcaaga ttagataaaa   4260
gtaaagtgat taacagcgca ttagagctgc ttaatgaggt cggaatcgaa ggtttaacaa   4320
cccgtaaact cgcccagaag ctaggtgtag agcagcctac attgtattgg catgtaaaaa   4380
ataagcgggc tttgctcgac gccttagcca ttgagatgtt agataggcac catactcact   4440
tttgcccttt agaaggggaa agctggcaag atttttacg taataacgct aaaagtttta    4500
gatgtgcttt actaagtcat cgcgatggag caaaagtaca tttaggtaca cggcctacag   4560
aaaaacagta tgaaactctc gaaaatcaat tagccttttt atgccaacaa ggtttttcac   4620
tagagaatgc attatatgca ctcagcgctg tggggcattt tactttaggt tgcgtattgg   4680
aagatcaaga gcatcaagtc gctaaagaag aaagggaaac acctactact gatagtatgc   4740
cgccattatt acgacaagct atcgaattat ttgatcacca aggtgcagag ccagccttct   4800
tattcggcct tgaattgatc atatgcggat tagaaaaaca acttaaatgt gaaagtgggt   4860
cttaaaagca gcataacctt tttccgtgat ggtaacttca cggtaaccaa gatgtcgagt   4920
tgagctcgaa ttcgtaatca tggtcatagc tgtttcctgt gtgaaattgt tatccgctca   4980
caattccaca caacatacga gccggaagca taaagtgtaa agcctggggt gcctaatgag   5040
tgagctaact cacattaatt gcgttgcgct cactgcccgc tttccagtcg ggaaacctgt   5100
cgtgccagct gcattaatga atcggccaac gcgcggggag aggcggtttg cgtattgggc   5160
gctcttccgc ttcctcgctc actgactcgc tgcgctcggt cgttcggctg cggcgagcgg   5220
tatcagctca ctcaaaggcg gtaatacggt tatccacaga atcaggggat aacgcaggaa   5280
agaacatgtg agcaaaaggc cagcaaaagg ccaggaaccg taaaaaggcc gcgttgctgg   5340
cgtttttcca taggctccgc ccccctgacg agcatcacaa aaatcgacgc tcaagtcaga   5400
ggtggcgaaa cccgacagga ctataaagat accaggcgtt tccccctgga agctccctcg   5460
tgcgctctcc tgttccgacc ctgccgctta ccggatacct gtccgccttt ctcccttcgg   5520
gaagcgtggc gctttctcat agctcacgct gtaggtatct cagttcggtg taggtcgttc   5580
gctccaagct gggctgtgtg cacgaacccc ccgttcagcc cgaccgctgc gccttatccg   5640
gtaactatcg tcttgagtcc aacccggtaa gacacgactt atcgccactg gcagcagcca   5700
ctggtaacag gattagcaga gcgaggtatg taggcggtgc tacagagttc ttgaagtggt   5760
ggcctaacta cggctacact agaaggacag tatttggtat ctgcgctctg ctgaagccag   5820
ttaccttcgg aaaaagagtt ggtagctctt gatccggcaa acaaaccacc gctggtagcg   5880
gtggtttttt tgtttgcaag cagcagatta cgcgcagaaa aaaaggatct caagaagatc   5940
ctttgatctt ttctacgggg tctgacgctc agtggaacga aaactcacgt taagggattt   6000
tggtcatgag attatcaaaa aggatcttca cctagatcct tttaaattaa aaatgaagtt   6060
ttaaatcaat ctaaagtata tatgagtaaa cttggtctga cagttaccag gtccactgcc   6120
```

-continued

```
gggcctcttg cgggatcaaa agaaaaacga aatgatacac caatcagtgc aaaaaaagat   6180
ataatgggag ataagacggt tcgtgttcgt gctgacttgc accatatcat aaaaatcgaa   6240
acagcaaaga atggcggaaa cgtaaaagaa gttatggaaa taagacttag aagcaaactt   6300
aagagtgtgt tgatagtgca gtatcttaaa attttgtata ataggaattg aagttaaatt   6360
agatgctaaa aatttgtaat taagaaggag tgattacatg aacaaaaata taaaatattc   6420
tcaaaacttt ttaacgagtg aaaaagtact caaccaaata ataaaacaat tgaatttaaa   6480
agaaaccgat accgtttacg aaattggaac aggtaaaggg catttaacga cgaaactggc   6540
taaaataagt aaacaggtaa cgtctattga attagacagt catctattca acttatcgtc   6600
agaaaaatta aaactgaata ctcgtgtcac tttaattcac caagatattc tacagtttca   6660
attccctaac aaacagaggt ataaaattgt tgggagtatt ccttaccatt taagcacaca   6720
aattattaaa aaagtggttt ttgaaagcca tgcgtctgac atctatctga ttgttgaaga   6780
aggattctac aagcgtacct tggatattca ccgaacacta gggttgctct tgcacactca   6840
agtctcgatt cagcaattgc ttaagctgcc agcggaatgc tttcatccta aaccaaaagt   6900
aaacagtgtc ttaataaaac ttacccgcca taccacagat gttccagata aatattggaa   6960
gctatatacg tactttgttt caaaatgggt caatcgagaa tatcgtcaac tgtttactaa   7020
aaatcagttt catcaagcaa tgaaacacgc caaagtaaac aatttaagta ccgttactta   7080
tgagcaagta ttgtctattt ttaatagtta tctattattt aacgggagga aataattcta   7140
tgagtcccta ggcaggcctc cgccattatt tttttgaaca attgacaatt catttcttat   7200
tttttattaa gtgatagtca aaaggcataa cagtgctgaa tagaaagaaa tttacagaaa   7260
agaaaattat agaatttagt atgattaatt atactcattt atgaatgttt aattgaatac   7320
aaaaaaaaat acttgttatg tattcaatta cgggttaaaa tatagacaag ttgaaaaatt   7380
taataaaaaa ataagtcctc agctcttata tattaagcta ccaacttagt atataagcca   7440
aaacttaaat gtgctaccaa cacatcaagc cgttagagaa ctctatctat agcaatattt   7500
caaatgtacc gacatacaag agaaacatta actatatata ttcaatttat gagattatct   7560
taacagatat aaatgtaaat tgcaataagt aagatttaga agtttatagc ctttgtgtat   7620
tggaagcagt acgcaaaggc ttttttattt gataaaaatt agaagtatat ttattttttc   7680
ataattaatt tatgaaaatg aaagggggtg agcaaagtga cagaggaaag cagtatctta   7740
tcaaataaca aggtattagc aatatcatta ttgactttag cagtaaacat tatgactttt   7800
atagtgcttg tagctaagta gtacgaaagg gggagcttta aaaagctcct tggaatacat   7860
agaattcata aattaattta tgaaaagaag ggcgtatatg aaaacttgta aaaattgcaa   7920
agagtttatt aaagatactg aaatatgcaa aatacattcg ttgatgattc atgataaaac   7980
agtagcaacc tattgcagta aatacaatga gtcaagatgt ttacataaag ggaaagtcca   8040
atgtattaat tgttcaaaga tgaaccgata tggatggtgt gccataaaaa tgagatgttt   8100
tacagaggaa gaacagaaaa aagaacgtac atgcattaaa tattatgcaa ggagctttaa   8160
aaaagctcat gtaaagaaga gtaaaaagaa aaaataattt atttattaat ttaatattga   8220
gagtgccgac acagtatgca ctaaaaaata tatctgtggt gtagtgagcc gatacaaaag   8280
gatagtcact cgcattttca taatacatct tatgttatga ttatgtgtcg gtgggacttc   8340
acgacgaaaa cccacaataa aaaaagagtt cggggtaggg ttaagcatag ttgaggcaac   8400
taaacaatca agctaggata tgcagtagca gaccgtaagg tcgttgttta ggtgtgttgt   8460
```

-continued aatacatacg ctattaagat gtaaaaatac ggataccaat gaagggaaaa gtataatttt 8520
tggatgtagt ttgtttgttc atctatgggc aaactacgtc caaagccgtt tccaaatctg 8580
ctaaaaagta tatcctttct aaaatcaaag tcaagtatga aatcataaat aaagtttaat 8640
tttgaagtta ttatgatatt atgtttttct attaaaataa attaagtata tagaatagtt 8700
taataatagt atatacttaa tgtgataagt gtctgacagt gtcacagaaa ggatgattgt 8760
tatggattat aagcggctcg agtccctatc agtgatagat tgaaactcta tcattgatag 8820
agtataatat ctttgttcat tagagcgata aacttgaatt tgagagggaa cttc 8874

<210> SEQ ID NO 8
<211> LENGTH: 4938
<212> TYPE: DNA
<213> ORGANISM: Artificial Sequence
<220> FEATURE:
<223> OTHER INFORMATION: plasmid

<400> SEQUENCE: 8
tcgactctag aggatccccg ggtaccgagc tcgaattcgt aatcatggtc atagctgttt 60
cctgtgtgaa attgttatcc gctcacaatt ccacacaaca tacgagccgg aagcataaag 120
tgtaaagcct ggggtgccta atgagtgagc taactcacat taattgcgtt gcgctcactg 180
cccgctttcc agtcgggaaa cctgtcgtgc cagctgcatt aatgaatcgg ccaacgcgcg 240
gggagaggcg gtttgcgtat tgggcgctct tccgcttcct cgctcactga ctcgctgcgc 300
tcggtcgttc ggctgcggcg agcggtatca gctcactcaa aggcggtaat acggttatcc 360
acagaatcag gggataacgc aggaaagaac atgtgagcaa aaggccagca aaaggccagg 420
aaccgtaaaa aggccgcgtt gctggcgttt ttccataggc tccgcccccc tgacgagcat 480
cacaaaaatc gacgctcaag tcagaggtgg cgaaacccga caggactata aagataccag 540
gcgtttcccc ctggaagctc cctcgtgcgc tctcctgttc cgaccctgcc gcttaccgga 600
tacctgtccg cctttctccc ttcgggaagc gtggcgcttt ctcatagctc acgctgtagg 660
tatctcagtt cggtgtaggt cgttcgctcc aagctgggct gtgtgcacga accccccgtt 720
cagcccgacc gctgcgcctt atccggtaac tatcgtcttg agtccaaccc ggtaagacac 780
gacttatcgc cactggcagc agccactggt aacaggatta gcagagcgag gtatgtaggc 840
ggtgctacag agttcttgaa gtggtggcct aactacggct acactagaag aacagtattt 900
ggtatctgcg ctctgctgaa gccagttacc ttcggaaaaa gagttggtag ctcttgatcc 960
ggcaaacaaa ccaccgctgg tagcggtggt ttttttgttt gcaagcagca gattacgcgc 1020
agaaaaaaag gatctcaaga agatcctttg atcttttcta cggggtctga cgctcagtgg 1080
aacgaaaact cacgttaagg gattttggtc atgagattat caaaaaggat cttcacctag 1140
atccttttaa attaaaaatg aagttttaaa tcaatctaaa gtatatatga gtaaacttgg 1200
tctgacagtt accaaagcta gcttaatact agtatatact taatgtgata agtgtctgac 1260
agctgaccgg tctaaagagg tccctagcgc ctacggggaa tttgtatcga taaggggtac 1320
aaattcccac taagcgctcg gccggggatc gatccccggg tacgtacccg gcagtttttc 1380
tttttcggca agtgttcaag aagttattaa gtcgggagtg cagtcgaagt gggcaagttg 1440
aaaaattcac aaaaatgtgg tataatatct ttgttcatta gagcgataaa cttgaatttg 1500
agagggaact tagatggtat ttgaaaaaat tgataaaaat agttggaaca gaaaagagta 1560
ttttgaccac tactttgcaa gtgtaccttg tacctacagc atgaccgtta aagtggatat 1620
cacacaaata aaggaaaagg gaatgaaact atatcctgca atgctttatt atattgcaat 1680

-continued

```
gattgtaaac cgccattcag agtttaggac ggcaatcaat caagatggtg aattggggat   1740
atatgatgag atgataccaa gctatacaat atttcacaat gatactgaaa cattttccag   1800
cctttggact gagtgtaagt ctgactttaa atcattttta gcagattatg aaagtgatac   1860
gcaacggtat ggaaacaatc atagaatgga aggaaagcca aatgctccgg aaaacatttt   1920
taatgtatct atgataccgt ggtcaacctt cgatggcttt aatctgaatt tgcagaaagg   1980
atatgattat ttgattccta tttttactat ggggaaatat tataaagaag ataacaaaat   2040
tatacttcct ttggcaattc aagttcatca cgcagtatgt gacggatttc acatttgccg   2100
ttttgtaaac gaattgcagg aattgataaa tagttaactt caggtttgtc tgtaactaaa   2160
aactagtatt taacctagga tcaaaaaaat ttccaataat cccactctaa gccacaaaca   2220
cgccctataa aatcccgctt taatcccact ttgagacaca tgtaatatta ctttacgccc   2280
tagtatagtg ataatttttt acattcaatg ccacgcaaaa aaataaaggg gcactataat   2340
aaaagttcct tcggaactaa ctaaagtaaa aaattatctt tacaacctcc ccaaaaaaaa   2400
gaacaggtac aaagtaccct ataatacaag cgtaaaaaaa atgagggtaa aaataaaaaa   2460
ataaaaaaat aaaaaaataa aaaaataaaa aaataaaaaa ataaaaaaat ataaaaataa   2520
aaaaatataa aaataaaaaa atataaaaat aaaaaaataa aaaaatataa aaataaaaaa   2580
ataaaaaaat ataaaaatat tttttattta aagtttgaaa aaaatttttt tatattatat   2640
aatctttgaa gaaaagaata taaaaaatga gcctttataa aagcccattt tttttcatat   2700
acgtaatatg acgttctaat gtttttattg gtacttctaa cattagagta atttctttat   2760
ttttaaagcc tttttcttta agggctttta ttttttttct taatacattt aattcctctt   2820
tttttgttgc ttttccttta gcttttaatt gctcttgata attttttta cctctaatat   2880
tttctcttct cttatattcc tttttagaaa ttattattgt catatatttt tgttcttctt   2940
ctgtaatttc taataactct ataagagttt cattcttata cttatattgc ttatttttat   3000
ctaaataaca tctttcagca cttctagttg ctcttataac ttctctttca cttaaatgtt   3060
gtctaaacat actattaagt tctaaaacat catttaatgc cttctcaatg tcttctgtaa   3120
agctacaaag ataatatcta tataaaaata atataagctc tctgtgtcct tttaaatcat   3180
attctcttag ttcacaaagt tttattatgt cttgtattct tccataatat aaacttcttt   3240
ctctataaat ataatttatt ttgcttggtc taccctttt cctttcatat ggttttaatt   3300
caggtaaaaa tccattttgt atttctctta agtcataaat atattcgtac tcatctaata   3360
tattgactac tgtttttgat ttagagttta tacttcctgg aactcttaat attctcgttg   3420
catctaaggc ttgtctatct gctccaaagt attttaattg attatataaa tattcttgaa   3480
ccgctttcca taatggtaat gctttactag gtactgcatt tattatccat attaaataca   3540
ttcctcttcc actatctatt acatagtttg gtataggaat actttgatta aaataattct   3600
tttctaagtc cattaatacc tggtctttag ttttgccagt tttataataa tccaagtcta   3660
taaacagtgt atttaactct tttatatttt ctaatcgcct acacggctta taaaaggtat   3720
ttagagttat atagatattt tcatcactca tatctaaatc ttttaattca gcgtatttat   3780
agtgccattg gctatatcct tttttatcta taacgctcct ggttatccac cctttacttc   3840
tactatgaat attatctata tagttctttt tattcagctt taatgcgttt ctcacttatt   3900
cacctcccct tctgtaaaac taagaaaatt atatcatatt ttcaataatt attaactatt   3960
cttaaactct taataaaaaa tagagtaagt ccccaattga aacttaatct attttttatg   4020
```

-continued

```
ttttaattta ttatttttat taaaatattt taaactaaat taaatgattc tttttaattt   4080
tttactattt cattccataa tatattacta taattattta caaataatat ttcttcattt   4140
gtaatattta gatgatttac taattttagt ttttatatat taaataatta atgtataatt   4200
tatataaaaa atcaaaggag cttataaatt atgattattt ccaaagatac taaagattta   4260
attttttca attttaacaa tactttttgt aatattatgt ttaaatttaa ttgtattttt    4320
ttcatataat aaagccgttg aagtaaacca atccattttc cttatgatgt tattattaaa   4380
tttaagtttt ataataatat ctttattata tttattgttt ttaaaaaaac tagtgaaatt   4440
tctagtgaaa tttccggctt tattaaactt atttttagga attttatttt cattttcatc   4500
tttacaggat ttgattatat ctttaaatat gttttatcaa atattatctt tttctaaatt   4560
tatatatatt tttattatat ttattattat atatatttta tttttaagtt tctttctaac   4620
agctattaaa aagaaactta aaaataaaaa cacgtactct aaaccaataa ataaaactat   4680
ttttattatt gctgccttga ttggaatagt ttttagtaaa attaatttca atattccaca   4740
atattatatt ataagctagc acgcctcgag tatattgata aaaataataa tagtgggtat   4800
aattaagttg ttaggaggtt agttagactt aaaatccata tataacagtt ttagagctag   4860
aaatagcaag ttaaaataag gctagtccgt tatcaacttg aaaaagtggc accgagtcgg   4920
tgcttttttt gaagcttg                                                  4938
```

<210> SEQ ID NO 9
<211> LENGTH: 4938
<212> TYPE: DNA
<213> ORGANISM: Artificial Sequence
<220> FEATURE:
<223> OTHER INFORMATION: plasmid

<400> SEQUENCE: 9

```
tcgactctag aggatccccg ggtaccgagc tcgaattcgt aatcatggtc atagctgttt     60
cctgtgtgaa attgttatcc gctcacaatt ccacacaaca tacgagccgg aagcataaag    120
tgtaaagcct ggggtgccta atgagtgagc taactcacat taattgcgtt gcgctcactg    180
cccgctttcc agtcgggaaa cctgtcgtgc cagctgcatt aatgaatcgg ccaacgcgcg    240
gggagaggcg gtttgcgtat tgggcgctct tccgcttcct cgctcactga ctcgctgcgc    300
tcggtcgttc ggctgcggcg agcggtatca gctcactcaa aggcggtaat acggttatcc    360
acagaatcag gggataacgc aggaaagaac atgtgagcaa aaggccagca aaaggccagg    420
aaccgtaaaa aggccgcgtt gctggcgttt ttccataggc tccgcccccc tgacgagcat    480
cacaaaaatc gacgctcaag tcagaggtgg cgaaacccga caggactata aagataccag    540
gcgtttcccc ctggaagctc cctcgtgcgc tctcctgttc cgaccctgcc gcttaccgga    600
tacctgtccg cctttctccc ttcgggaagc gtggcgcttt ctcatagctc acgctgtagg    660
tatctcagtt cggtgtaggt cgttcgctcc aagctgggct gtgtgcacga accccccgtt    720
cagcccgacc gctgcgcctt atccggtaac tatcgtcttg agtccaaccc ggtaagacac    780
gacttatcgc cactggcagc agccactggt aacaggatta gcagagcgag gtatgtaggc    840
ggtgctacag agttcttgaa gtggtggcct aactacggct acactagaag aacagtattt    900
ggtatctgcg ctctgctgaa gccagttacc ttcggaaaaa gagttggtag ctcttgatcc    960
ggcaaacaaa ccaccgctgg tagcggtggt ttttttgttt gcaagcagca gattacgcgc   1020
agaaaaaaag gatctcaaga agatcctttg atcttttcta cggggtctga cgctcagtgg   1080
aacgaaaact cacgttaagg gattttggtc atgagattat caaaaaggat cttcacctag   1140
```

atccttttaa attaaaaatg aagttttaaa tcaatctaaa gtatatatga gtaaacttgg 1200
tctgacagtt accaaagcta gcttaatact agtatatact taatgtgata agtgtctgac 1260
agctgaccgg tctaaagagg tccctagcgc ctacggggaa tttgtatcga taaggggtac 1320
aaattcccac taagcgctcg gccggggatc gatccccggg tacgtacccg gcagtttttc 1380
tttttcggca agtgttcaag aagttattaa gtcgggagtg cagtcgaagt gggcaagttg 1440
aaaaattcac aaaaatgtgg tataatatct ttgttcatta gagcgataaa cttgaatttg 1500
agagggaact tagatggtat ttgaaaaaat tgataaaaat agttggaaca gaaaagagta 1560
ttttgaccac tactttgcaa gtgtaccttg tacctacagc atgaccgtta aagtggatat 1620
cacacaaata aaggaaaagg gaatgaaact atatcctgca atgctttatt atattgcaat 1680
gattgtaaac cgccattcag agtttaggac ggcaatcaat caagatggtg aattggggat 1740
atatgatgag atgataccaa gctatacaat atttcacaat gatactgaaa cattttccag 1800
cctttggact gagtgtaagt ctgactttaa atcattttta gcagattatg aaagtgatac 1860
gcaacggtat ggaaacaatc atagaatgga aggaaagcca aatgctccgg aaaacatttt 1920
taatgtatct atgataccgt ggtcaacctt cgatggcttt aatctgaatt tgcagaaagg 1980
atatgattat ttgattccta tttttactat ggggaaatat tataaagaag ataacaaaat 2040
tatacttcct ttggcaattc aagttcatca cgcagtatgt gacggatttc acatttgccg 2100
ttttgtaaac gaattgcagg aattgataaa tagttaactt caggtttgtc tgtaactaaa 2160
aactagtatt taacctagga tcaaaaaaat ttccaataat cccactctaa gccacaaaca 2220
cgccctataa aatcccgctt taatcccact ttgagacaca tgtaatatta ctttacgccc 2280
tagtatagtg ataatttttt acattcaatg ccacgcaaaa aaataaaggg gcactataat 2340
aaaagttcct tcggaactaa ctaaagtaaa aaattatctt tacaacctcc ccaaaaaaaa 2400
gaacaggtac aaagtaccct ataatacaag cgtaaaaaaa atgagggtaa aaataaaaaa 2460
ataaaaaaat aaaaaaataa aaaaataaaa aaataaaaaa ataaaaaaat ataaaaataa 2520
aaaaatataa aaataaaaaa atataaaaat aaaaaaataa aaaaatataa aaataaaaaa 2580
ataaaaaaat ataaaaatat tttttattta aagtttgaaa aaaatttttt tatattatat 2640
aatctttgaa gaaaagaata taaaaaatga gcctttataa aagcccattt tttttcatat 2700
acgtaatatg acgttctaat gtttttattg gtacttctaa cattagagta atttctttat 2760
ttttaaagcc tttttcttta agggctttta ttttttttct taatacattt aattcctctt 2820
tttttgttgc ttttccttta gcttttaatt gctcttgata atttttttta cctctaatat 2880
tttctcttct cttatattcc tttttagaaa ttattattgt catatatttt tgttcttctt 2940
ctgtaatttc taataactct ataagagttt cattcttata cttatattgc ttatttttat 3000
ctaaataaca tctttcagca cttctagttg ctcttataac ttctctttca cttaaatgtt 3060
gtctaaacat actattaagt tctaaaacat catttaatgc cttctcaatg tcttctgtaa 3120
agctacaaag ataatatcta tataaaaata atataagctc tctgtgtcct tttaaatcat 3180
attctcttag ttcacaaagt tttattatgt cttgtattct tccataatat aaacttcttt 3240
ctctataaat ataatttatt ttgcttggtc taccctttt cctttcatat ggttttaatt 3300
caggtaaaaa tccattttgt atttctctta agtcataaat atattcgtac tcatctaata 3360
tattgactac tgtttttgat ttagagttta tacttcctgg aactcttaat attctcgttg 3420
catctaaggc ttgtctatct gctccaaagt attttaattg attatataaa tattcttgaa 3480

-continued

```
ccgctttcca taatggtaat gctttactag gtactgcatt tattatccat attaaataca   3540
ttcctcttcc actatctatt acatagtttg gtataggaat actttgatta aaataattct   3600
tttctaagtc cattaatacc tggtctttag ttttgccagt tttataataa tccaagtcta   3660
taaacagtgt atttaactct tttatatttt ctaatcgcct acacggctta taaaaggtat   3720
ttagagttat atagatattt tcatcactca tatctaaatc ttttaattca gcgtatttat   3780
agtgccattg gctatatcct tttttatcta taacgctcct ggttatccac cctttacttc   3840
tactatgaat attatctata tagttctttt tattcagctt taatgcgttt ctcacttatt   3900
cacctcccct tctgtaaaac taagaaaatt atatcatatt ttcaataatt attaactatt   3960
cttaaactct taataaaaaa tagagtaagt ccccaattga aacttaatct atttttttatg   4020
ttttaattta ttatttttat taaaatattt taaactaaat taaatgattc tttttaattt   4080
tttactattt cattccataa tatattacta taattattta caaataatat ttcttcattt   4140
gtaatattta gatgatttac taattttagt ttttatatat taaataatta atgtataatt   4200
tatataaaaa atcaaaggag cttataaatt atgattattt ccaaagatac taaagattta   4260
atttttttca attttaacaa tactttttgt aatattatgt ttaaatttaa ttgtattttt   4320
ttcatataat aaagccgttg aagtaaacca atccattttc cttatgatgt tattattaaa   4380
tttaagtttt ataataatat ctttattata tttattgttt ttaaaaaaac tagtgaaatt   4440
tctagtgaaa tttccggctt tattaaactt atttttagga attttatttt cattttcatc   4500
tttacaggat ttgattatat ctttaaatat gttttatcaa atattatctt tttctaaatt   4560
tatatatatt tttattatat ttattattat atatatttta tttttaagtt tctttctaac   4620
agctattaaa aagaaactta aaaataaaaa cacgtactct aaaccaataa ataaaactat   4680
ttttattatt gctgccttga ttggaatagt ttttagtaaa attaatttca atattccaca   4740
atattatatt ataagctagc acgcctcgag tatattgata aaaataataa tagtgggtat   4800
aattaagttg ttaggaggtt agttagaact aaatgtaaaa tgttagcgtt ttagagctag   4860
aaatagcaag ttaaaataag gctagtccgt tatcaacttg aaaaagtggc accgagtcgg   4920
tgcttttttt gaagcttg                                                 4938
```

<210> SEQ ID NO 10
<211> LENGTH: 5911
<212> TYPE: DNA
<213> ORGANISM: Artificial Sequence
<220> FEATURE:
<223> OTHER INFORMATION: plasmid

<400> SEQUENCE: 10

```
aattcgtaat catggtcata gctgtttcct gtgtgaaatt gttatccgct cacaattcca     60
cacaacatac gagccggaag cataaagtgt aaagcctggg gtgcctaatg agtgagctaa    120
ctcacattaa ttgcgttgcg ctcactgccc gctttccagt cgggaaacct gtcgtgccag    180
ctgcattaat gaatcggcca acgcgcgggg agaggcggtt tgcgtattgg gcgctcttcc    240
gcttcctcgc tcactgactc gctgcgctcg gtcgttcggc tgcggcgagc ggtatcagct    300
cactcaaagg cggtaatacg gttatccaca gaatcagggg ataacgcagg aaagaacatg    360
tgagcaaaag gccagcaaaa ggccaggaac cgtaaaaagg ccgcgttgct ggcgtttttc    420
cataggctcc gcccccctga cgagcatcac aaaaatcgac gctcaagtca gaggtggcga    480
aacccgacag gactataaag ataccaggcg tttccccctg gaagctccct cgtgcgctct    540
cctgttccga ccctgccgct taccggatac ctgtccgcct ttctcccttc gggaagcgtg    600
```

```
gcgctttctc atagctcacg ctgtaggtat ctcagttcgg tgtaggtcgt tcgctccaag    660
ctgggctgtg tgcacgaacc ccccgttcag cccgaccgct gcgccttatc cggtaactat    720
cgtcttgagt ccaacccggt aagacacgac ttatcgccac tggcagcagc cactggtaac    780
aggattagca gagcgaggta tgtaggcggt gctacagagt tcttgaagtg gtggcctaac    840
tacggctaca ctagaagaac agtatttggt atctgcgctc tgctgaagcc agttaccttc    900
ggaaaaagag ttggtagctc ttgatccggc aaacaaacca ccgctggtag cggtggtttt    960
tttgtttgca agcagcagat tacgcgcaga aaaaaaggat ctcaagaaga tcctttgatc   1020
ttttctacgg ggtctgacgc tcagtggaac gaaaactcac gttaagggat tttggtcatg   1080
agattatcaa aaaggatctt cacctagatc cttttaaatt aaaaatgaag ttttaaatca   1140
atctaaagta tatatgagta aacttggtct gacagttacc aaagctagct taatactagt   1200
atatacttaa tgtgataagt gtctgacagc tgaccggtct aaagaggtcc ctagcgccta   1260
cggggaattt gtatcgataa ggggtacaaa ttcccactaa gcgctcggcc ggggatcgat   1320
ccccgggtac gtacccggca gtttttcttt ttcggcaagt gttcaagaag ttattaagtc   1380
gggagtgcag tcgaagtggg caagttgaaa aattcacaaa aatgtggtat aatatctttg   1440
ttcattagag cgataaactt gaatttgaga gggaacttag atggtatttg aaaaaattga   1500
taaaaatagt tggaacagaa aagagtattt tgaccactac tttgcaagtg taccttgtac   1560
ctacagcatg accgttaaag tggatatcac acaaataaag gaaaagggaa tgaaactata   1620
tcctgcaatg ctttattata ttgcaatgat tgtaaaccgc cattcagagt ttaggacggc   1680
aatcaatcaa gatggtgaat tggggatata tgatgagatg ataccaagct atacaatatt   1740
tcacaatgat actgaaacat tttccagcct ttggactgag tgtaagtctg actttaaatc   1800
atttttagca gattatgaaa gtgatacgca acggtatgga aacaatcata gaatggaagg   1860
aaagccaaat gctccggaaa acatttttaa tgtatctatg ataccgtggt caaccttcga   1920
tggctttaat ctgaatttgc agaaaggata tgattatttg attcctattt ttactatggg   1980
gaaatattat aaagaagata acaaaattat acttcctttg gcaattcaag ttcatcacgc   2040
agtatgtgac ggatttcaca tttgccgttt tgtaaacgaa ttgcaggaat tgataaatag   2100
ttaacttcag gtttgtctgt aactaaaaac tagtatttaa cctaggatca aaaaaatttc   2160
caataatccc actctaagcc acaaacacgc cctataaaat cccgctttaa tcccactttg   2220
agacacatgt aatattactt tacgccctag tatagtgata atttttttaca ttcaatgcca   2280
cgcaaaaaaa taaaggggca ctataataaa agttccttcg gaactaacta aagtaaaaaa   2340
ttatctttac aacctcccca aaaaaaagaa caggtacaaa gtaccctata atacaagcgt   2400
aaaaaaaatg agggtaaaaa taaaaaaata aaaaaataaa aaaataaaaa aataaaaaaa   2460
taaaaaaata aaaaaatata aaaataaaaa aatataaaaa taaaaaaata taaaaataaa   2520
aaaataaaaa aatataaaaa taaaaaaata aaaaaatata aaaatatttt ttatttaaag   2580
tttgaaaaaa attttttttat attatataat ctttgaagaa aagaatataa aaaatgagcc   2640
tttataaaag cccatttttt ttcatatacg taatatgacg ttctaatgtt tttattggta   2700
cttctaacat tagagtaatt tctttatttt taaagccttt ttctttaagg gcttttattt   2760
tttttcttaa tacatttaat tcctcttttt ttgttgcttt tcctttagct tttaattgct   2820
cttgataatt ttttttacct ctaatatttt ctcttctctt atattccttt ttagaaatta   2880
ttattgtcat atatttttgt tcttcttctg taatttctaa taactctata agagtttcat   2940
```

-continued

```
tcttatactt atattgctta tttttatcta aataacatct ttcagcactt ctagttgctc   3000
ttataacttc tctttcactt aaatgttgtc taaacatact attaagttct aaaacatcat   3060
ttaatgcctt ctcaatgtct tctgtaaagc tacaaagata atatctatat aaaaataata   3120
taagctctct gtgtcctttt aaatcatatt ctcttagttc acaaagtttt attatgtctt   3180
gtattcttcc ataatataaa cttctttctc tataaatata atttattttg cttggtctac   3240
ccttttttcct ttcatatggt tttaattcag gtaaaaatcc attttgtatt tctcttaagt   3300
cataaatata ttcgtactca tctaatatat tgactactgt ttttgattta gagtttatac   3360
ttcctggaac tcttaatatt ctcgttgcat ctaaggcttg tctatctgct ccaaagtatt   3420
ttaattgatt atataaatat tcttgaaccg ctttccataa tggtaatgct ttactaggta   3480
ctgcatttat tatccatatt aaatacattc ctcttccact atctattaca tagtttggta   3540
taggaatact ttgattaaaa taattctttt ctaagtccat taatacctgg tctttagttt   3600
tgccagtttt ataataatcc aagtctataa acagtgtatt taactctttt atattttcta   3660
atcgcctaca cggcttataa aaggtattta gagttatata gatattttca tcactcatat   3720
ctaaatcttt taattcagcg tatttatagt gccattggct atatcctttt ttatctataa   3780
cgctcctggt tatccaccct ttacttctac tatgaatatt atctatatag ttctttttat   3840
tcagctttaa tgcgtttctc acttattcac ctccccttct gtaaaactaa gaaaattata   3900
tcatattttc aataattatt aactattctt aaactcttaa taaaaaatag agtaagtccc   3960
caattgaaac ttaatctatt ttttatgttt taatttatta tttttattaa aatattttaa   4020
actaaattaa atgattcttt ttaatttttt actatttcat tccataatat attactataa   4080
ttatttacaa ataatatttc ttcatttgta atatttagat gatttactaa ttttagtttt   4140
tatatattaa ataattaatg tataatttat ataaaaaatc aaaggagctt ataaattatg   4200
attatttcca aagatactaa agatttaatt tttttcaatt ttaacaatac tttttgtaat   4260
attatgttta aatttaattg tattttttttc atataataaa gccgttgaag taaaccaatc   4320
cattttcctt atgatgttat tattaaattt aagttttata ataatatctt tattatattt   4380
attgttttta aaaaaactag tgaaatttct agtgaaattt ccggctttat taaacttatt   4440
tttaggaatt ttattttcat tttcatcttt acaggatttg attatatctt taaatatgtt   4500
ttatcaaata ttatcttttt ctaaatttat atatattttt attatattta ttattatata   4560
tattttattt ttaagtttct ttctaacagc tattaaaaag aaacttaaaa ataaaaacac   4620
gtactctaaa ccaataaata aaactatttt tattattgct gccttgattg gaatagtttt   4680
tagtaaaatt aatttcaata ttccacaata ttatattata agctagcacg cctcgagtat   4740
attgataaaa ataataatag tgggtataat taagttgtta ggaggttagt tagaactaaa   4800
tgtaaaatgt tagcgtttta gagctagaaa tagcaagtta aaataaggct agtccgttat   4860
caacttgaaa aagtggcacc gagtcggtgc ttttttttgaa gcttgtcgac atgaagatag   4920
caataggtag tgatcatgca ggattttcat tgaaaaagga agttataaaa catttagaga   4980
gtaaaaatat tgaggttaaa gattttggca ctctaactga tgaatcatgt gattatccag   5040
attatgcatt aaaagtagca gaggaagttg ctcaaaaaaa ctttgagttt ggaatactca   5100
tttgtggaac aggtatagga ataagcatat cagcaaataa ggtgccagga ataagagcag   5160
ctgtatgtac agatacattc tgtgctcatg catcaagaga acataacaat gcaaatatac   5220
ttgcaatggg agaaagagtt gtaggacctg gattagcaat tgatatagta gatacatttt   5280
taaattcaaa atttcaggga gataggcatc aaagaagaat agacaagatt acacaaatag   5340
```

aaaaaaaaata caatggagga atgaaataat gagtaaagtt acacaaatat cacatccact 5400
tatattacac aaacttcctc aagatataga ggaaagagac ataatagtaa ctgatccaat 5460
gcttgcaact ggtgggtcag caatagatgc aataacactt cttaagaaaa gaggagcaaa 5520
atacataaga cttatgtgtc ttataggagc accagaaggt atagcagcag tacaagaagc 5580
acatccagat gtagatatat acctcgcatc aatagatgaa aagttagatg aaaatggata 5640
tatagttcct ggtcttggag atgctggaga tagattattc ggtacaaaat aaattgcata 5700
aataaaaagg gctgaaaaat aaatttcagt ccttttattt atattttaac tttattccat 5760
gccactgcct cttctgataa taatagaaat tattaaagtt aatacagatg taagggcaac 5820
tgttccacct ggagcacaat ttaagtaata agagctaaat aatccaacga gtacatctat 5880
aaagctaaat aatattgata atataagcgt g 5911

<210> SEQ ID NO 11
<211> LENGTH: 6217
<212> TYPE: DNA
<213> ORGANISM: Artificial Sequence
<220> FEATURE:
<223> OTHER INFORMATION: plasmid

<400> SEQUENCE: 11
aattcgtaat catggtcata gctgtttcct gtgtgaaatt gttatccgct cacaattcca 60
cacaacatac gagccggaag cataaagtgt aaagcctggg gtgcctaatg agtgagctaa 120
ctcacattaa ttgcgttgcg ctcactgccc gctttccagt cgggaaacct gtcgtgccag 180
ctgcattaat gaatcggcca acgcgcgggg agaggcggtt tgcgtattgg gcgctcttcc 240
gcttcctcgc tcactgactc gctgcgctcg gtcgttcggc tgcggcgagc ggtatcagct 300
cactcaaagg cggtaatacg gttatccaca gaatcagggg ataacgcagg aaagaacatg 360
tgagcaaaag gccagcaaaa ggccaggaac cgtaaaaagg ccgcgttgct ggcgtttttc 420
cataggctcc gcccccctga cgagcatcac aaaaatcgac gctcaagtca gaggtggcga 480
aacccgacag gactataaag ataccaggcg tttccccctg gaagctccct cgtgcgctct 540
cctgttccga ccctgccgct taccggatac ctgtccgcct ttctcccttc gggaagcgtg 600
gcgctttctc atagctcacg ctgtaggtat ctcagttcgg tgtaggtcgt tcgctccaag 660
ctgggctgtg tgcacgaacc ccccgttcag cccgaccgct gcgccttatc cggtaactat 720
cgtcttgagt ccaacccggt aagacacgac ttatcgccac tggcagcagc cactggtaac 780
aggattagca gagcgaggta tgtaggcggt gctacagagt tcttgaagtg gtggcctaac 840
tacggctaca ctagaagaac agtatttggt atctgcgctc tgctgaagcc agttaccttc 900
ggaaaaagag ttggtagctc ttgatccggc aaacaaacca ccgctggtag cggtggtttt 960
tttgtttgca agcagcagat tacgcgcaga aaaaaaggat ctcaagaaga tcctttgatc 1020
ttttctacgg ggtctgacgc tcagtggaac gaaaactcac gttaagggat tttggtcatg 1080
agattatcaa aaaggatctt cacctagatc cttttaaatt aaaaatgaag ttttaaatca 1140
atctaaagta tatatgagta aacttggtct gacagttacc aaagctagct taatactagt 1200
atatacttaa tgtgataagt gtctgacagc tgaccggtct aaagaggtcc ctagcgccta 1260
cggggaattt gtatcgataa ggggtacaaa ttcccactaa gcgctcggcc ggggatcgat 1320
ccccgggtac gtacccggca gtttttcttt ttcggcaagt gttcaagaag ttattaagtc 1380
gggagtgcag tcgaagtggg caagttgaaa aattcacaaa aatgtggtat aatatctttg 1440

```
ttcattagag cgataaactt gaatttgaga gggaacttag atggtatttg aaaaaattga   1500
taaaaatagt tggaacagaa aagagtattt tgaccactac tttgcaagtg taccttgtac   1560
ctacagcatg accgttaaag tggatatcac acaaataaag gaaaagggaa tgaaactata   1620
tcctgcaatg ctttattata ttgcaatgat tgtaaaccgc cattcagagt ttaggacggc   1680
aatcaatcaa gatggtgaat tggggatata tgatgagatg ataccaagct atacaatatt   1740
tcacaatgat actgaaacat tttccagcct ttggactgag tgtaagtctg actttaaatc   1800
atttttagca gattatgaaa gtgatacgca acggtatgga aacaatcata gaatggaagg   1860
aaagccaaat gctccggaaa acattttttaa tgtatctatg ataccgtggt caaccttcga   1920
tggctttaat ctgaatttgc agaaaggata tgattatttg attcctattt ttactatggg   1980
gaaatattat aaagaagata acaaaattat acttcctttg gcaattcaag ttcatcacgc   2040
agtatgtgac ggatttcaca tttgccgttt tgtaaacgaa ttgcaggaat tgataaatag   2100
ttaacttcag gtttgtctgt aactaaaaac tagtatttaa cctaggatca aaaaaatttc   2160
caataatccc actctaagcc acaaacacgc cctataaaat cccgctttaa tcccactttg   2220
agacacatgt aatattactt tacgccctag tatagtgata attttttaca ttcaatgcca   2280
cgcaaaaaaa taaaggggca ctataataaa agttccttcg gaactaacta aagtaaaaaa   2340
ttatctttac aacctcccca aaaaaaagaa caggtacaaa gtaccctata atacaagcgt   2400
aaaaaaaatg agggtaaaaa taaaaaaata aaaaaataaa aaaataaaaa aataaaaaaa   2460
taaaaaaata aaaaaatata aaaataaaaa aatataaaaa taaaaaaata taaaaataaa   2520
aaaataaaaa aatataaaaa taaaaaaata aaaaaatata aaaatatttt ttatttaaag   2580
tttgaaaaaa atttttttat attatataat ctttgaagaa aagaatataa aaaatgagcc   2640
tttataaaag cccatttttt ttcatatacg taatatgacg ttctaatgtt tttattggta   2700
cttctaacat tagagtaatt tctttatttt taaagccttt ttctttaagg gcttttattt   2760
tttttcttaa tacatttaat tcctcttttt ttgttgcttt tcctttagct tttaattgct   2820
cttgataatt ttttttacct ctaatatttt ctcttctctt atattccttt ttagaaatta   2880
ttattgtcat atatttttgt tcttcttctg taatttctaa taactctata agagtttcat   2940
tcttatactt atattgctta tttttatcta aataacatct ttcagcactt ctagttgctc   3000
ttataacttc tctttcactt aaatgttgtc taaacatact attaagttct aaaacatcat   3060
ttaatgcctt ctcaatgtct tctgtaaagc tacaaagata atatctatat aaaaaataata   3120
taagctctct gtgtcctttt aaatcatatt ctcttagttc acaaagtttt attatgtctt   3180
gtattcttcc ataatataaa cttctttctc tataaatata atttattttg cttggtctac   3240
ccttttttcct ttcatatggt tttaattcag gtaaaaatcc attttgtatt tctcttaagt   3300
cataaatata ttcgtactca tctaatatat tgactactgt ttttgattta gagtttatac   3360
ttcctggaac tcttaatatt ctcgttgcat ctaaggcttg tctatctgct ccaaagtatt   3420
ttaattgatt atataaatat tcttgaaccg ctttccataa tggtaatgct ttactaggta   3480
ctgcatttat tatccatatt aaatacattc ctcttccact atctattaca tagtttggta   3540
taggaatact ttgattaaaa taattctttt ctaagtccat taatacctgg tctttagttt   3600
tgccagtttt ataataatcc aagtctataa acagtgtatt taactctttt atattttcta   3660
atcgcctaca cggcttataa aaggtattta gagttatata gatattttca tcactcatat   3720
ctaaatcttt taattcagcg tatttatagt gccattggct atatcctttt ttatctataa   3780
cgctcctggt tatccaccct ttacttctac tatgaatatt atctatatag ttctttttat   3840
```

-continued

```
tcagctttaa tgcgtttctc acttattcac ctccccttct gtaaaactaa gaaaattata   3900
tcatattttc aataattatt aactattctt aaactcttaa taaaaaatag agtaagtccc   3960
caattgaaac ttaatctatt ttttatgttt taatttatta tttttattaa aatattttaa   4020
actaaattaa atgattcttt ttaatttttt actatttcat tccataatat attactataa   4080
ttatttacaa ataatatttc ttcatttgta atatttagat gatttactaa ttttagtttt   4140
tatatattaa ataattaatg tataatttat ataaaaaatc aaaggagctt ataaattatg   4200
attatttcca aagatactaa agatttaatt tttttcaatt ttaacaatac tttttgtaat   4260
attatgttta aatttaattg tattttttc atataataaa gccgttgaag taaaccaatc   4320
cattttcctt atgatgttat tattaaattt aagttttata ataatatctt tattatattt   4380
attgttttta aaaaaactag tgaaatttct agtgaaattt ccggctttat taaacttatt   4440
tttaggaatt ttattttcat tttcatcttt acaggatttg attatatctt taaatatgtt   4500
ttatcaaata ttatcttttt ctaaatttat atatattttt attatattta ttattatata   4560
tattttattt ttaagtttct ttctaacagc tattaaaaag aaacttaaaa ataaaaacac   4620
gtactctaaa ccaataaata aaactatttt tattattgct gccttgattg gaatagtttt   4680
tagtaaaatt aatttcaata ttccacaata ttatattata agctagcacg cctcgagtat   4740
attgataaaa ataataatag tgggtataat taagttgtta ggaggttagt tagaactaaa   4800
tgtaaaatgt tagcgtttta gagctagaaa tagcaagtta aaataaggct agtccgttat   4860
caacttgaaa aagtggcacc gagtcggtgc ttttttgaa gcttgtcgac atgaagatag   4920
caataggtag tgatcatgca ggattttcat tgaaaaagga agttataaaa catttagaga   4980
gtaaaaatat tgaggttaaa gattttggca ctctaactga tgaatcatgt gattatccag   5040
attatgcatt aaaagtagca gaggaagttg ctcaaaaaaa ctttgagttt ggaatactca   5100
tttgtggaac aggtatagga ataagcatat cagcaaataa ggtgccagga ataagagcag   5160
ctgtatgtac agatacattc tgtgctcatg catcaagaga acataacaat gcaaatatac   5220
ttgcaatggg agaaagagtt gtaggacctg gattagcaat tgatatagta gatacatttt   5280
taaattcaaa atttcaggga gataggcatc aaagaagaat agacaagatt acacaaatag   5340
aaaaaaaata caatggagga atgaaataat gagtaaagtt acacaaatat cacatccact   5400
tatattacac aaattagcat ttatgagaga taaaaaaaca ggatctaaag attttagaga   5460
gatggtagaa gaagtagcaa tgctaatggc atatgaagta acaagagaaa tgcagcttga   5520
aactgttgaa atagaaactc ctatatgtat aactaaatgt aagatgtaag caggaaaaaa   5580
ggtagctata gttcctatac ttagagcagg acttggaatg gtaaatggag tattaaaatt   5640
aatacctgct gctaaggttg gacatatagg attatataga gatgaaaaga cattaaaacc   5700
tgtagaatac ttctgtaaac ttcctcaaga tatagaggaa agagacataa tagtaactga   5760
tccaatgctt gcaactggtg ggtcagcaat agatgcaata acacttctta agaaaagagg   5820
agcaaaatac ataagactta tgtgtcttat aggagcacca gaaggtatag cagcagtaca   5880
agaagcacat ccagatgtag atatatacct cgcatcaata gatgaaaagt tagatgaaaa   5940
tggatatata gttcctggtc ttggagatgc tggagataga ttattcggta caaaataaat   6000
tgcataaata aaaagggctg aaaaataaat ttcagtcctt ttatttatat tttaacttta   6060
ttccatgcca ctgcctcttc tgataataat agaaattatt aaagttaata cagatgtaag   6120
ggcaactgtt ccacctggag cacaatttaa gtaataagag ctaaataatc caacgagtac   6180
```

atctataaag ctaaataata ttgataatat aagcgtg 6217

<210> SEQ ID NO 12
<211> LENGTH: 1002
<212> TYPE: DNA
<213> ORGANISM: Artificial Sequence
<220> FEATURE:
<223> OTHER INFORMATION: upp_del

<400> SEQUENCE: 12
catgaagata gcaataggta gtgatcatgc aggattttca ttgaaaaagg aagttataaa 60
acatttagag agtaaaaata ttgaggttaa agattttggc actctaactg atgaatcatg 120
tgattatcca gattatgcat taaaagtagc agaggaagtt gctcaaaaaa actttgagtt 180
tggaatactc atttgtggaa caggtatagg aataagcata tcagcaaata aggtgccagg 240
aataagagca gctgtatgta cagatacatt ctgtgctcat gcatcaagag aacataacaa 300
tgcaaatata cttgcaatgg gagaaagagt tgtaggacct ggattagcaa ttgatatagt 360
agatacattt ttaaattcaa aatttcaggg agataggcat caaagaagaa tagacaagat 420
tacacaaata gaaaaaaaat acaatggagg aatgaaataa tgagtaaagt tacacaaata 480
tcacatccac ttatattaca caaacttcct caagatatag aggaaagaga cataatagta 540
actgatccaa tgcttgcaac tggtgggtca gcaatagatg caataacact tcttaagaaa 600
agaggagcaa aatacataag acttatgtgt cttataggag caccagaagg tatagcagca 660
gtacaagaag cacatccaga tgtagatata tacctcgcat caatagatga aaagttagat 720
gaaaatggat atatagttcc tggtcttgga gatgctggag atagattatt cggtacaaaa 780
taaattgcat aaataaaaag ggctgaaaaa taaatttcag tcctttttatt tatattttaa 840 ctttattcca tgccactgcc tcttctgata ataatagaaa ttattaaagt taatacagat 900
gtaagggcaa ctgttccacc tggagcacaa tttaagtaat aagagctaaa taatccaacg 960
agtacatcta taaagctaaa taatattgat aatataagcg tg 1002

<210> SEQ ID NO 13
<211> LENGTH: 1306
<212> TYPE: DNA
<213> ORGANISM: Artificial Sequence
<220> FEATURE:
<223> OTHER INFORMATION: upp_stop

<400> SEQUENCE: 13
atgaagatag caataggtag tgatcatgca ggattttcat tgaaaaagga agttataaaa 60
catttagaga gtaaaaatat tgaggttaaa gattttggca ctctaactga tgaatcatgt 120
gattatccag attatgcatt aaaagtagca gaggaagttg ctcaaaaaaa ctttgagttt 180
ggaatactca tttgtggaac aggtatagga ataagcatat cagcaaataa ggtgccagga 240
ataagagcag ctgtatgtac agatacattc tgtgctcatg catcaagaga acataacaat 300
gcaaatatac ttgcaatggg agaaagagtt gtaggacctg gattagcaat tgatatagta 360
gatacatttt taaattcaaa atttcaggga gataggcatc aaagaagaat agacaagatt 420
acacaaatag aaaaaaaata caatggagga atgaaataat gagtaaagtt acacaaatat 480
cacatccact tatattacac aaattagcat ttatgagaga taaaaaaaca ggatctaaag 540
attttagaga gatggtagaa gaagtagcaa tgctaatggc atatgaagta acaagagaaa 600
tgcagcttga aactgttgaa atagaaactc ctatatgtat aactaaatgt aagatgtaag 660
caggaaaaaa ggtagctata gttcctatac ttagagcagg acttggaatg gtaaatggag 720

-continued

```
tattaaaatt aatacctgct gctaaggttg gacatatagg attatataga gatgaaaaga    780

cattaaaacc tgtagaatac ttctgtaaac ttcctcaaga tatagaggaa agagacataa    840

tagtaactga tccaatgctt gcaactggtg ggtcagcaat agatgcaata acacttctta    900

agaaaagagg agcaaaatac ataagactta tgtgtcttat aggagcacca gaaggtatag    960

cagcagtaca agaagcacat ccagatgtag atatatacct cgcatcaata gatgaaaagt   1020

tagatgaaaa tggatatata gttcctggtc ttggagatgc tggagataga ttattcggta   1080

caaaataaat tgcataaata aaaagggctg aaaaataaat ttcagtcctt ttatttatat   1140

tttaacttta ttccatgcca ctgcctcttc tgataataat agaaattatt aaagttaata   1200

cagatgtaag ggcaactgtt ccacctggag cacaatttaa gtaataagag ctaaataatc   1260

caacgagtac atctataaag ctaaataata ttgataatat aagcgt                  1306


<210> SEQ ID NO 14
<211> LENGTH: 22
<212> TYPE: DNA
<213> ORGANISM: Artificial Sequence
<220> FEATURE:
<223> OTHER INFORMATION: primer

<400> SEQUENCE: 14

gtgggcaagt tgaaaaattc ac                                              22


<210> SEQ ID NO 15
<211> LENGTH: 28
<212> TYPE: DNA
<213> ORGANISM: Artificial Sequence
<220> FEATURE:
<223> OTHER INFORMATION: primer

<400> SEQUENCE: 15

ttaactattt atcaattcct gcaattcg                                        28


<210> SEQ ID NO 16
<211> LENGTH: 21
<212> TYPE: DNA
<213> ORGANISM: Artificial Sequence
<220> FEATURE:
<223> OTHER INFORMATION: primer

<400> SEQUENCE: 16

cttgagactt tgccgtgagg g                                               21


<210> SEQ ID NO 17
<211> LENGTH: 20
<212> TYPE: DNA
<213> ORGANISM: Artificial Sequence
<220> FEATURE:
<223> OTHER INFORMATION: primer

<400> SEQUENCE: 17

tagttggaat gggcgctagt                                                 20


<210> SEQ ID NO 18
<211> LENGTH: 29
<212> TYPE: DNA
<213> ORGANISM: Artificial Sequence
<220> FEATURE:
<223> OTHER INFORMATION: primer

<400> SEQUENCE: 18
```

atgaagatag caataggtag tgatcatgc 29

<210> SEQ ID NO 19
<211> LENGTH: 34
<212> TYPE: DNA
<213> ORGANISM: Artificial Sequence
<220> FEATURE:
<223> OTHER INFORMATION: primer

<400> SEQUENCE: 19
acgcttatat tatcaatatt atttagcttt atag 34

<210> SEQ ID NO 20
<211> LENGTH: 20
<212> TYPE: DNA
<213> ORGANISM: Artificial Sequence
<220> FEATURE:
<223> OTHER INFORMATION: primer

<400> SEQUENCE: 20
tgtccaacct tagcagcagg 20

<210> SEQ ID NO 21
<211> LENGTH: 26
<212> TYPE: DNA
<213> ORGANISM: Artificial Sequence
<220> FEATURE:
<223> OTHER INFORMATION: primer

<400> SEQUENCE: 21
gtagaagaag tagcaatgct aatggc 26

<210> SEQ ID NO 22
<211> LENGTH: 62
<212> TYPE: DNA
<213> ORGANISM: Clostridium acetobutylicum

<400> SEQUENCE: 22
aaactcctat atgtataact aaatgtaaaa tgttagcagg aaaaaaggta gctatagttc 60
ct 62

<210> SEQ ID NO 23
<211> LENGTH: 62
<212> TYPE: DNA
<213> ORGANISM: Artificial Sequence
<220> FEATURE:
<223> OTHER INFORMATION: fragment upp_stop fig7

<400> SEQUENCE: 23
aaactcctat atgtataact aaatgtaaga tgtaagcagg aaaaaaggta gctatagttc 60
ct 62

<210> SEQ ID NO 24
<211> LENGTH: 86
<212> TYPE: DNA
<213> ORGANISM: Clostridium acetobutylicum

<400> SEQUENCE: 24
aaactgttga aatagaaact cctatatgta taactaaatg taaaatgtta gcaggaaaaa 60
aggtagctat agttcctata cttaga 86

<210> SEQ ID NO 25
<211> LENGTH: 86

<212> TYPE: DNA
<213> ORGANISM: Artificial Sequence
<220> FEATURE:
<223> OTHER INFORMATION: fragment upp_stop fig16

<400> SEQUENCE: 25
aaactgttga aatagaaact cctatatgta taactaaatg taagatgtaa gcaggaaaaa 60
aggtagctat agttcctata cttaga 86

<210> SEQ ID NO 26
<211> LENGTH: 10537
<212> TYPE: DNA
<213> ORGANISM: Artificial Sequence
<220> FEATURE:
<223> OTHER INFORMATION: plasmid

<400> SEQUENCE: 26
tcgactctag aggatcctac ttggttttat agagatttta aggaggaagc tatgaagata 60
ctttttgttt gtactggtaa tacatgtaga agctgtatgg cagaagctat gtttaatagt 120
atgtgtaata tagatggtat agaagctttt tcagcaggtg catctgctat tcatggaagc 180
aaaacttcct taaattcggc tgtggtagtt agggagaact taggcaaaga tatatcaaat 240
agaaaggcta tacagttgac tactttttta gttgatgaat gtgatttagt tttaacaatg 300
acatctttat taagtgacgt gcttagaagt caaatggaga agaactctaa taagatatat 360
tcattaagtg aatatacagg tgtagagggt gacattactg acccatatgg tagaagtgta 420
gagatctaca gacaaactta taaagacatt gaaaagaggc taaaaatact tattaaaaaa 480
ctaaatgaag atagaagtat ttaatcatat actcttatct tctttttttg cgattatgta 540
ttaagtggag gtgtttttat gaagatagca ataggtagtg atcatgcagg attttcattg 600
aaaaaggaag ttataaaaca tttagagagt aaaaatattg aggttaaaga ttttggcact 660
ctaactgatg aatcatgtga ttatccagat tatgcattaa aagtagcaga ggaagttgct 720
caaaaaaact ttgagtttgg aatactcatt tgtggaacag gtataggaat aagcatatca 780
gcaaataagg tgccaggaat aagagcagct gtatgtacag atacattctg tgctcatgca 840
tcaagagaac ataacaatgc aaatatactt gcaatgggag aaagagttgt aggacctgga 900
ttagcaattg atatagtaga tacattttta aattcaaaat ttcagggaga taggcatcaa 960
agaagaatag acaagattac acaaatagaa aaaaaataca atggaggaat gaaataaaaa 1020
aataagagtt accatttaag gtaactctta tttttattac ttaagataat catatataac 1080
ttcagctcta ggcaatatta tatctgcaag aatgtgagag ctagaaacaa tctcttttac 1140
tggcaaatca ttaagtggcg ccatagcgtg atcaaataac tgcagtcgag ttggtcctgt 1200
ccaagcttca tgtacggtaa catctgtgat tttcgcattt ataagctcac atattctagg 1260
gcttccatca taattgggta ttattttcaa catataatta gggcgacaaa tttgatcctt 1320
tgcttcatta gcatctaagg ctttatgttt gtaccccatt gtagctgtcg caactctaag 1380
ttttccatag tctaaagttc ctactaaagt atctgaatcc acaaaaagct ttggataccc 1440
gagcttttta ggatatgcac ttaattccct tcctactgca attgcaggct cattatctaa 1500
atacatcata tgaagataat ctcccttaac tccattaaag cttacgggaa tagcctgtcc 1560
gctttctgta taacaaccaa gtccactcgt atcatgcatt gccataattt caaacctgac 1620
taagggctca tcaatttcta aaggctctgg cacaacttta cgaagtgcat ccatatctgt 1680
acgatataca atgttaaaat actcacgatt atgaaattta tagggtcctc taggaaatgc 1740

-continued

```
aggcgaagtt aatggcgtgc taatttgttt aattacttca tcctttaaca taaaagtcac   1800
cttcctaaat ttaataatgt ttagcttttc taacatactt tatcttcaca ttataaatcg   1860
cctctagtcc tatttattta tatctagtta ttttttgtcg actgtttcat agtatttctt   1920
tctaaacagc catgggtcta agttcattgg atatgagtaa atctgcagca gttaaagacc   1980
ttatttcatc aatggttgtg tttttattaa tttcagtgag aagtaaacca tcattaataa   2040
cctcaattac tccaagttct gttacaatta gatttgcttg agactttgcc gtgaggggaa   2100
gtgtacattt ttttaaaatt ttaggttgac ctttatttgt atgtctcatt gcaattatta   2160
ctttcttagc tccatttact aaatccatag ctccacccat accagagagc atttttccag   2220
gaacaatcca attggctata ttaccctttt catctacctg gagagcccct aaaacagtaa   2280
catctacgtg accaccacgg attagtgaaa acgaaactga gctatcgaaa aatgtgccgt   2340
caggaagtac tgttgtatag tctcctcctg catttactac atctttatct gcctcattta   2400
ttttaggact agcgcccatt ccaactattc cgttttctga ttggaaagta attttgaaat   2460
tttttggtat ataatctgca accatggtag gaagacctac acctaagttt acaagttgac   2520
catttttttaa ttctcttgca actcttttgg ctattatttc tttcgctagg tttttatcat   2580
taatcatttt atgcaggctc ctttactata taatttataa gaactccggg ggtcattgct   2640
ttttcctttt ctagtttttc acagctaact aaattttcag cttcaactat tacggtttta   2700
gctgccattg ccatataggg attaaagttt ttagtagtac ctttatagaa ggtgtttccg   2760
gcctcatcta caatactacc tttaattaat gctacatcgg ctgtaagagg tagctctaac   2820
aaatattccg ttccatttat agatattttt ttctttcctt tttcaatcaa agttcctaaa   2880
cctgttttag ttagtacacc acctaagcca gatccgcctg cacgtattct ttccactaga   2940
gttccttggg gagagagctc tacttcaagt tcattattaa aaagtttttt gccagtatct   3000
gggttgctgc ctatatatga agcaataagc ttttttactt gattatttga tattaactta   3060
ccaatacctg tattaggata acatgtatca ttacttataa tcgttaaatt ctttatattt   3120
aaattaacta aaaaatcaat taatttggtt ggagtgccac agtttaaaaa acctccaatc   3180
ataattgtca tcccatcttt aaagaatgac cttaaatttt caaatctaat tattttagag   3240
ttcattttaa tccctccttt taaattctct agaaaaatta tctcgaggta taatcctcca   3300
tgatctatta tgttataata taactactgc tttaattaag tcttttggct tgtctttcat   3360
taataacagt gcttcttcta tgtgatcaaa tccatgatat acatgtgtaa ctaatttact   3420
tagatcaaca cgattatata ctaccatatc tcttaacatt tctgctctca aacgtccccc   3480
aggacaaaga cctcctttta tagtcttgtg agccattcca catccccatt ctacacgtgg   3540
tattagtaaa gcatctccac ttccatgata atttatatta gaaattattc ctcctggttt   3600
aaccatagat actgcttggg ataatgtttc agaaccaccg cctgccataa ttacgcggtc   3660
aacgcctttt ccattcgtta atttcataac ttgatcaact atatgaccat ttttataatt   3720
tagaatatct gttgctccat aaaattttgc agcctcaaca caaatcggcc tgctccccac   3780
tccaattatt ctacctgctc cacgtaattt agcacctgct attcccatta agccaacagc   3840
tccaatgcca attaccacaa cacttgaacc catttgaata tctgcaagtt ctgctccatg   3900
aaatccagta gtcatcatat ctgttatcat aacagcattt tctaatggca tgtctttagg   3960
tagaatcgca agattcatat ccgcatcatt tacatgaaaa tattcaccaa aaactccatc   4020
cttgaaattt gaaaatttcc atcctgcgag cataccgttt gagtgctgtt gaaaaccagc   4080
ttgaacttcc aaagatctcc aatctggagt tgtacaagga actataactc tgtcaccagg   4140
```

-continued

```
tttaaaatcc ttcacttcac ttcctacttc aacaacttca cctacagctt catgccctaa   4200
aatcatattc ttcctatctc caagagctcc ctcaaaaaca gtatgtatat ctgatgtaca   4260
cggagatact gctaatgggc gtacaatagc atcatatgaa cccgcaactg gcctttcttt   4320
ttcgatccat cctaacttat taatacctag cattgcaaaa cctttcataa aatatgttcc   4380
tccttaaaaa tattccttta atagtctaag ggcccccata gtttatccct aatttatacg   4440
ttttctctaa caacttaatt atacccacta ttattatttt tatcaatata ttttgttaaa   4500
aaaaacacaa agtttaatat tttttaacaa aaaaattaaa cttatgcata tgctaacccc   4560
cttaaaatca tgttttagca taaatacata agtttatatt ttaactatat taatgtaata   4620
aaaaatactt gattgcataa ataaaaaggg ctgaaaaata aatttcagtc cttttattta   4680
tattttaact ttattccatg ccactgcctc ttctgataat aatagaaatt attaaagtta   4740
atacagatgt aagggcaact gttccacctg gagcacaatt taagtaataa gagctaaata   4800
atccaacgag tacatctata aagctaaata atattgataa tataagcgtt gacttaaatc   4860
ccttttttaaa ctgcatagca gcagctacag gtacagctaa tagtgaagag acaactaata   4920
tccctgttat acgtattgaa acggatataa cgaaaccgac aacgatagaa aatatgtaat   4980
ttaaaaattt tgtgtttatg ccagataccc ttgcaccttg ctcatcaaat gttgtatata   5040
aaaagttgtt ataaaatata gctataagaa atatagatac tacacttatt attagtataa   5100
gtacgagatc acttttacca acagttaaaa tacttccaaa aagaaaagat tcaatgtttc   5160
cgcttgcacg tccacttgtt gttaaggtta tagctattcc aacagataga gttaatataa   5220
ttggaagtat taagtccgaa tactgcttaa aggagtttct aagtaattct attaagacag   5280
cacaaatagt tacaaaaata aaggttgtta tcataggatt tacgccaata aagataccta   5340
tagctacacc ggcaaaagaa gcatgtgata atgcatcacc taccattgag tgtcttttta   5400
aaactaagaa aatacctata agtggacaca aaattgcaat cattaccgag gcaagtaaag   5460
cgttttgcat aaaacttaga cgaaatagtt caatcattat ttaacaacct ccatattgct   5520
ttttaaaaaa tcgttaatgt taagcaaaga gccactttct ccatggaaat tgaaaatatg   5580
agttgaatta gaataagcag cctttaaatt atgttctaca catattattg tgaattcgta   5640
atcatggtca tagctgtttc ctgtgtgaaa ttgttatccg ctcacaattc cacacaacat   5700
acgagccgga agcataaagt gtaaagcctg gggtgcctaa tgagtgagct aactcacatt   5760
aattgcgttg cgctcactgc ccgctttcca gtcgggaaac ctgtcgtgcc agctgcatta   5820
atgaatcggc caacgcgcgg ggagaggcgg tttgcgtatt gggcgctctt ccgcttcctc   5880
gctcactgac tcgctgcgct cggtcgttcg gctgcggcga gcggtatcag ctcactcaaa   5940
ggcggtaata cggttatcca cagaatcagg ggataacgca ggaaagaaca tgtgagcaaa   6000
aggccagcaa aaggccagga accgtaaaaa ggccgcgttg ctggcgtttt tccataggct   6060
ccgcccccct gacgagcatc acaaaaatcg acgctcaagt cagaggtggc gaaacccgac   6120
aggactataa agataccagg cgtttccccc tggaagctcc ctcgtgcgct ctcctgttcc   6180
gaccctgccg cttaccggat acctgtccgc ctttctccct tcgggaagcg tggcgctttc   6240
tcatagctca cgctgtaggt atctcagttc ggtgtaggtc gttcgctcca agctgggctg   6300
tgtgcacgaa ccccccgttc agcccgaccg ctgcgcctta tccggtaact atcgtcttga   6360
gtccaacccg gtaagacacg acttatcgcc actggcagca gccactggta acaggattag   6420
cagagcgagg tatgtaggcg gtgctacaga gttcttgaag tggtggccta actacggcta   6480
```

-continued

```
cactagaaga acagtatttg gtatctgcgc tctgctgaag ccagttacct tcggaaaaag   6540
agttggtagc tcttgatccg gcaaacaaac caccgctggt agcggtggtt tttttgtttg   6600
caagcagcag attacgcgca gaaaaaaagg atctcaagaa gatcctttga tcttttctac   6660
ggggtctgac gctcagtgga acgaaaactc acgttaaggg attttggtca tgagattatc   6720
aaaaaggatc ttcacctaga tccttttaaa ttaaaaatga agttttaaat caatctaaag   6780
tatatatgag taaacttggt ctgacagtta ccaaagctag cttaatacta gtatatactt   6840
aatgtgataa gtgtctgaca gctgaccggt ctaaagaggt ccctagcgcc tacggggaat   6900
ttgtatcgat aaggggtaca aattcccact aagcgctcgg ccggggatcg atccccgggt   6960
acgtacccgg cagtttttct tttcggcaa gtgttcaaga agttattaag tcgggagtgc   7020
agtcgaagtg ggcaagttga aaaattcaca aaaatgtggt ataatatctt tgttcattag   7080
agcgataaac ttgaatttga gagggaactt agatggtatt tgaaaaaatt gataaaaata   7140
gttggaacag aaaagagtat tttgaccact actttgcaag tgtaccttgt acctacagca   7200
tgaccgttaa agtggatatc acacaaataa aggaaaaggg aatgaaacta tatcctgcaa   7260
tgctttatta tattgcaatg attgtaaacc gccattcaga gtttaggacg gcaatcaatc   7320
aagatggtga attggggata tatgatgaga tgataccaag ctatacaata tttcacaatg   7380
atactgaaac attttccagc ctttggactg agtgtaagtc tgactttaaa tcatttttag   7440
cagattatga aagtgatacg caacggtatg gaaacaatca tagaatggaa ggaaagccaa   7500
atgctccgga aaacattttt aatgtatcta tgataccgtg gtcaaccttc gatggcttta   7560
atctgaattt gcagaaagga tatgattatt tgattcctat tttactatg gggaaatatt   7620
ataaagaaga taacaaaatt atacttcctt tggcaattca agttcatcac gcagtatgtg   7680
acggatttca catttgccgt tttgtaaacg aattgcagga attgataaat agttaacttc   7740
aggtttgtct gtaactaaaa actagtattt aacctaggat caaaaaaatt tccaataatc   7800
ccactctaag ccacaaacac gccctataaa atcccgcttt aatcccactt tgagacacat   7860
gtaatattac tttacgccct agtatagtga taatttttta cattcaatgc cacgcaaaaa   7920
aataaagggg cactataata aaagttcctt cggaactaac taaagtaaaa aattatcttt   7980
acaacctccc caaaaaaaag aacaggtaca aagtacccta taatacaagc gtaaaaaaaa   8040
tgagggtaaa aataaaaaaa taaaaaaata aaaaaataaa aaaataaaaa aataaaaaaa   8100
taaaaaaata taaaaataaa aaaatataaa aataaaaaaa tataaaaata aaaaaataaa   8160
aaaatataaa aataaaaaaa taaaaaaata taaaaatatt ttttatttaa agtttgaaaa   8220
aaattttttt atattatata atctttgaag aaaagaatat aaaaaatgag cctttataaa   8280
agcccatttt ttttcatata cgtaatatga cgttctaatg tttttattgg tacttctaac   8340
attagagtaa tttctttatt tttaaagcct ttttctttaa gggcttttat ttttttttctt   8400
aatacattta attcctcttt ttttgttgct tttcctttag cttttaattg ctcttgataa   8460
ttttttttac ctctaatatt ttctcttctc ttatattcct ttttagaaat tattattgtc   8520
atatattttt gttcttcttc tgtaatttct aataactcta taagagtttc attcttatac   8580
ttatattgct tatttttatc taaataacat ctttcagcac ttctagttgc tcttataact   8640
tctctttcac ttaaatgttg tctaaacata ctattaagtt ctaaaacatc atttaatgcc   8700
ttctcaatgt cttctgtaaa gctacaaaga taatatctat ataaaaataa tataagctct   8760
ctgtgtcctt ttaaatcata ttctcttagt tcacaaagtt ttattatgtc ttgtattctt   8820
ccataatata aacttctttc tctataaata taatttattt tgcttggtct accctttttc   8880
```

ctttcatatg gttttaattc aggtaaaaat ccattttgta tttctcttaa gtcataaata 8940
tattcgtact catctaatat attgactact gtttttgatt tagagtttat acttcctgga 9000
actcttaata ttctcgttgc atctaaggct tgtctatctg ctccaaagta ttttaattga 9060
ttatataaat attcttgaac cgctttccat aatggtaatg ctttactagg tactgcattt 9120
attatccata ttaaatacat tcctcttcca ctatctatta catagtttgg tataggaata 9180
ctttgattaa aataattctt ttctaagtcc attaatacct ggtctttagt tttgccagtt 9240
ttataataat ccaagtctat aaacagtgta tttaactctt ttatattttc taatcgccta 9300
cacggcttat aaaaggtatt tagagttata tagatatttt catcactcat atctaaatct 9360
tttaattcag cgtatttata gtgccattgg ctatatcctt ttttatctat aacgctcctg 9420
gttatccacc ctttacttct actatgaata ttatctatat agttcttttt attcagcttt 9480
aatgcgtttc tcacttattc acctcccctt ctgtaaaact aagaaaatta tatcatattt 9540
tcaataatta ttaactattc ttaaactctt aataaaaaat agagtaagtc cccaattgaa 9600
acttaatcta ttttttatgt tttaatttat tatttttatt aaaatatttt aaactaaatt 9660
aaatgattct ttttaatttt ttactatttc attccataat atattactat aattatttac 9720
aaataatatt tcttcatttg taatatttag atgatttact aattttagtt tttatatatt 9780
aaataattaa tgtataattt atataaaaaa tcaaaggagc ttataaatta tgattatttc 9840
caaagatact aaagatttaa ttttttttcaa ttttaacaat actttttgta atattatgtt 9900
taaatttaat tgtatttttt tcatataata aagccgttga agtaaaccaa tccattttcc 9960
ttatgatgtt attattaaat ttaagtttta taataatatc tttattatat ttattgtttt 10020
taaaaaaact agtgaaattt ctagtgaaat ttccggcttt attaaactta tttttaggaa 10080
ttttattttc attttcatct ttacaggatt tgattatatc tttaaatatg ttttatcaaa 10140
tattatcttt ttctaaattt atatatattt ttattatatt tattattata tatattttat 10200
ttttaagttt ctttctaaca gctattaaaa agaaacttaa aaataaaaac acgtactcta 10260
aaccaataaa taaaactatt tttattattg ctgccttgat tggaatagtt tttagtaaaa 10320
ttaatttcaa tattccacaa tattatatta taagctagca cgcctcgagt atattgataa 10380
aaataataat agtgggtata attaagttgt taggaggtta gttagaacta aatgtaaaat 10440
gttagcgttt tagagctaga aatagcaagt taaaataagg ctagtccgtt atcaacttga 10500
aaaagtggca ccgagtcggt gcttttttttg aagcttg 10537

<210> SEQ ID NO 27
<211> LENGTH: 27
<212> TYPE: DNA
<213> ORGANISM: Artificial Sequence
<220> FEATURE:
<223> OTHER INFORMATION: primer

<400> SEQUENCE: 27
ctttttaaaa aagttaaata aggaagg 27

<210> SEQ ID NO 28
<211> LENGTH: 28
<212> TYPE: DNA
<213> ORGANISM: Artificial Sequence
<220> FEATURE:
<223> OTHER INFORMATION: primer

<400> SEQUENCE: 28

```
gtttaactta agttacagaa aagctagg                                      28


<210> SEQ ID NO 29
<211> LENGTH: 12849
<212> TYPE: DNA
<213> ORGANISM: Artificial Sequence
<220> FEATURE:
<223> OTHER INFORMATION: plasmid

<400> SEQUENCE: 29

ctagtagtgg atttaatccc aaatgagcca acagaaccag aaccagaaac agaatcagaa     60

caagtaacat tggatttaga aatggaagaa gaaaaaagca atgacttcgt gtgaataatg    120

cacgaaatcg ttgcttattt ttttttaaaa gcggtatact agatataacg aaacaacgaa    180

ctgaatagaa acgaaaaaag agccatgaca catttataaa atgtttgacg acattttata    240

aatgcatagc ccgataagat tgccaaacca acgcttatca gttagtcaga tgaactcttc    300

cctcgtaaga agttatttaa ttaactttgt ttgaagacgg tatataaccg tactatcatt    360

atatagggaa atcagagagt tttcaagtat ctaagctact gaatttaaga attgttaagc    420

aatcaatcgg aaatcgtttg attgcttttt ttgtattcat ttatagaagg tggagtttgt    480

atgaatcatg atgaatgtaa aacttatata aaaaatagtt tattggagat aagaaaatta    540

gcaaatatct atacactaga aacgtttaag aaagagttag aaaagagaaa tatctactta    600

gaaacaaaat cagataagta tttttcttcg gaggggggaag attatatata taagttaata    660

gaaaataaca aaataattta ttcgattagt ggaaaaaaat tgacttataa aggaaaaaaa    720

tctttttcaa aacatgcaat attgaaacag ttgaatgaaa aagcaaacca agttaattaa    780

acaacctatt ttataggatt tataggaaag gagaacagct gaatgaatat ccctttttgtt    840

gtagaaactg tgcttcatga cggcttgtta aagtacaaat ttaaaaatag taaaattcgc    900

tcaatcacta ccaagccagg taaaagcaaa ggggctattt ttgcgtatcg ctcaaaatca    960

agcatgattg gcggtcgtgg tgttgttctg acttccgagg aagcgattca agaaaatcaa   1020

gatacattta cacattggac acccaacgtt tatcgttatg gaacgtatgc agacgaaaac   1080

cgttcataca cgaaaggaca ttctgaaaac aatttaagac aaatcaatac cttctttatt   1140

gattttgata ttcacacggc aaaagaaact atttcagcaa gcgatatttt aacaaccgct   1200

attgatttag gttttatgcc tactatgatt atcaaatctg ataaaggtta tcaagcatat   1260

tttgttttag aaacgccagt ctatgtgact tcaaaatcag aatttaaatc tgtcaaagca   1320

gccaaaataa tttcgcaaaa tatccgagaa tattttggaa agtctttgcc agttgatcta   1380

acgtgtaatc attttggtat tgctcgcata ccaagaacgg acaatgtaga attttttgat   1440

cctaattacc gttattcttt caaagaatgg caagattggt ctttcaaaca aacagataat   1500

aagggcttta ctcgttcaag tctaacggtt ttaagcggta cagaaggcaa aaaacaagta   1560

gatgaaccct ggtttaatct cttattgcac gaaacgaaat tttcaggaga aaagggttta   1620

atagggcgta ataacgtcat gtttaccctc tctttagcct actttagttc aggctattca   1680

atcgaaacgt gcgaatataa tatgtttgag tttaataatc gattagatca acccttagaa   1740

gaaaaagaag taatcaaaat tgttagaagt gcctattcag aaaactatca aggggctaat   1800

agggaataca ttaccattct ttgcaaagct tgggtatcaa gtgatttaac cagtaaagat   1860

ttatttgtcc gtcaagggtg gtttaaattc aagaaaaaaa gaagcgaacg tcaacgtgtt   1920

catttgtcag aatggaaaga agatttaatg gcttatatta gcgaaaaaag cgatgtatac   1980

aagccttatt tagtgacgac caaaaaagag attagagaag tgctaggcat tcctgaacgg   2040
```

-continued

```
acattagata aattgctgaa ggtactgaag gcgaatcagg aaattttctt taagattaaa   2100
ccaggaagaa atggtggcat tcaacttgct agtgttaaat cattgttgct atcgatcatt   2160
aaagtaaaaa aagaagaaaa agaaagctat ataaaggcgc tgacaaattc ttttgactta   2220
gagcatacat tcattcaaga gactttaaac aagctagcag aacgccctaa aacggacaca   2280
caactcgatt tgtttagcta tgatacaggc tgaaaataaa acccgcacta tgccattaca   2340
tttatatcta tgatacgtgt ttgttttttc tttgctgttt agcgaatgat tagcagaaat   2400
atacagagta agattttaat taattattag gggagaagg agagagtagc ccgaaaactt    2460
ttagttggct tggactgaac gaagtgaggg aaaggctact aaaacgtcga ggggcagtga   2520
gagcgaagcg aacacttgat tttttaattt tctatctttt ataggtcatt agagtatact   2580
tatttgtcct ataaactatt tagcagcata atagatttat tgaataggtc atttaagttg   2640
agcatattag aggaggaaaa tcttggagaa atatttgaag aacccgatta catggattgg   2700
attagttctt gtggttacgt ggtttttaac taaaagtagt gaatttttga tttttggtgt   2760
gtgtgtcttg ttgttagtat ttgctagtca aagtgattaa atagaattct agcgccattc   2820
gccattcagg ctgcgcaact gttgggaagg gcgatcggtg cgggcctctt cgctattacg   2880
ccagctggcg aaagggggat gaaataaaag gttattttgc attgacaaag ataattaaat   2940
attttattat tagttcataa gttagtttaa tatactaaca aaaataaagc aagtaaaata   3000
tacctaaaat ataaaaaaat taggatagga aaacgatagt tatgaagtgg cattcaagga   3060
gggatggata aaaagtacag tattggtcta gacataggaa ctaactctgt tgggtgggct   3120
gttataacag atgaatataa agttccatca aaaaaattta aagtattagg aaacactgat   3180
agacattcaa taaaaaaaaa cttgataggt gctttattat tcgattcagg agagactgct   3240
gaagctacac gtttaaaaag aacagctaga cgtagatata caagaagaaa aaataggata   3300
tgttatcttc aagaaatttt tagtaatgaa atggcaaaag ttgatgattc attctttcac   3360
agactagaag aaagtttctt agttgaagaa gataagaagc atgaaagaca ccctattttt   3420
ggtaatatcg tagatgaagt agcatatcat gagaagtatc caactatcta tcatttaaga   3480
aagaaattag ttgattctac agataaagct gatctgagat taatatattt agctttagct   3540
catatgatta aatttagagg acattttta atagaaggtg atttaaaccc agacaacagc    3600
gatgtagata aattatttat ccaattagtt caaacttata atcaattatt cgaagagaat   3660
ccaattaatg caagtggtgt agacgctaag gctatattat cagctagatt atcaaaatct   3720
agaagattag aaaatctaat agctcaactt cctggagaaa agaaaaatgg actttttggg   3780
aacctaatag ctctctcact cggactaaca ccaaatttta aaagcaattt tgatcttgct   3840
gaagacgcaa agttacaact atcaaaggat acatacgatg atgatttaga taatttgtta   3900
gctcaaatag gtgatcaata tgctgatttg tttcttgcag caaaaaactt aagtgatgca   3960
attttactat cagatatact tagagtaaat acagaaataa caaaggctcc tttatcagca   4020
agtatgatta aacgatatga tgagcatcat caagatttaa cattattaaa ggcacttgta   4080
agacaacaat taccagaaaa atataaagaa attttctttg atcaatctaa aaatggatat   4140
gctggatata tagacggtgg agcaagtcaa gaagagtttt ataaatttat aaagcctatt   4200
ttagaaaaaa tggatggaac tgaagaatta cttgttaaac ttaacagaga agatttactt   4260
agaaaacaaa gaacttttga taatggttca attcctcacc aaattcattt aggagaatta   4320
catgctatac taagaagaca agaagatttt tatccatttc ttaaagataa tagagaaaaa   4380
```

-continued

```
attgaaaaaa ttttaacttt tagaatacca tattatgtag gaccacttgc aaggggaaat   4440
tcaagatttg catggatgac tagaaaatca gaagaaacta taaccccgtg gaattttgaa   4500
gaagtagtag ataaaggagc tagtgctcaa tcatttatag aaagaatgac aaattttgat   4560
aagaatcttc ctaacgaaaa ggttttgcca aagcatagcc ttctttatga gtattttaca   4620
gtttataatg agcttactaa agtaaaatac gttacagaag gaatgagaaa accagcattt   4680
ttgtctggtg aacaaaagaa agcaatagta gacctattat ttaaaacaaa taggaaggtt   4740
accgtaaagc aacttaaaga agattacttc aaaaaaattg aatgctttga tagtgttgaa   4800
atatcaggag ttgaagatag atttaatgct tcacttggta catatcacga tctcttaaaa   4860
attataaaag ataaggattt tttagataat gaagaaaatg aagatattct tgaagatata   4920
gtattaacat tgacactttt tgaagataga gaaatgatag aagaaagatt aaaaacatat   4980
gcacatcttt ttgatgataa ggttatgaag caacttaaaa gaagaagata tacaggttgg   5040
ggacgtttgt caagaaagct aattaatggt attagagata aacaatcagg aaagactatt   5100
ctcgattttc ttaaatcaga tggatttgct aatagaaact ttatgcaatt aattcatgat   5160
gattctctta ctttcaaaga ggatattcaa aaggctcaag tttctggaca aggcgatagc   5220
ttacacgaac acattgctaa ccttgcaggg agccccgcta tcaaaaaagg aattttacaa   5280
acagttaaag ttgtagatga acttgttaaa gttatgggaa gacacaaacc tgagaatata   5340
gttatagaaa tggccagaga aaatcaaaca acacaaaaag gacaaaaaaa ttctagagag   5400
agaatgaaga gaattgaaga aggaataaaa gagctaggat cacaaatatt aaaagaacat   5460
ccagttgaaa atactcaatt gcaaaatgaa aagttatatt tgtattactt acaaaatgga   5520
agagatatgt atgttgatca agaactcgat attaatagat taagtgacta tgatgttgat   5580
catattgttc ctcaatcatt tttaaaagat gattcaatcg ataacaaagt attaactaga   5640
tcagataaaa atagaggaaa gtcagataat gtaccatctg aagaagttgt taaaaaaatg   5700
aagaactatt ggagacaact tttaaatgca aagctaatta cacaaagaaa atttgacaat   5760
ttaacaaaag cagaaagagg aggattaagc gaattagaca aagctggatt tataaaaaga   5820
caacttgttg agacaagaca aataactaag catgttgctc aaatacttga ttcaagaatg   5880
aatacaaaat atgatgaaaa tgataaatta atcagagaag taaaagtaat aacattaaag   5940
tcaaaattag tatcagattt cagaaaggat tttcaatttt acaaagttcg tgaaataaat   6000
aactatcatc atgctcatga tgcatactta aatgctgttg taggaactgc tcttattaag   6060
aaatatccta aactagaaag cgaatttgtt tatggagatt ataaagttta tgatgtgcgc   6120
aaaatgatcg cgaaatccga acaagaaatc ggtaaggcta cagcaaaata tttcttttat   6180
agtaatataa tgaatttttt taagacagaa ataactttgg ctaatggtga aatcagaaaa   6240
agaccactta tcgaaacaaa tggagagaca ggagaaatag tatgggataa aggaagagat   6300
tttgctactg ttagaaaagt actaagtatg ccacaagtaa atatcgtaaa gaaaactgaa   6360
gttcaaactg gaggtttctc taaggaatca attttaccta agagaaattc agataagtta   6420
attgcaagga aaaaagattg ggacccaaaa aaatacggtg gttttgatag tccaacagtt   6480
gcctatagtg ttcttgtagt agcgaaagtt gagaaaggta agtcaaaaaa gttgaaaagc   6540
gtaaaagaac ttcttggtat cacaattatg gaaagatctt catttgaaaa aaatccaatt   6600
gactttttag aagctaaggg ttataaagaa gttaaaaagg atttaatcat aaaactacca   6660
aagtatagtc tatttgaact cgaaaacgga agaaaacgaa tgctcgctag cgcaggagaa   6720
cttcaaaaag gaaatgaact tgcgctgcca tcaaagtatg taaatttctt atatttagct   6780
```

```
tctcattatg agaaattaaa aggatcacca gaggataatg aacaaaagca actatttgta   6840
gaacaacaca aacattattt agatgaaata atagaacaaa tatctgaatt ttctaaaaga   6900
gttatacttg ccgacgcaaa tctagataag gtgctttcag cgtataataa acacagagat   6960
aaaccaataa gagaacaagc agaaaacatt atccatcttt ttacattaac taatcttggt   7020
gcaccagctg catttaagta ctttgataca acaatagata gaaaaagata cacatctact   7080
aaagaagtat tagacgcaac tttaatacat caatctatta cagggcttta tgaaacaaga   7140
attgatttaa gtcaactagg cggagattaa gaatttttt agaaagaaca tgtgagcaaa    7200
aggccagcaa aaggccagga accgtaaaaa ggccgcgttg ctggcgtttt tccataggct   7260
ccgcccccct gacgagcatc acaaaaatcg acgctcaagt cagaggtggc gaaacccgac   7320
aggactataa agataccagg cgtttccccc tggaagctcc ctcgtgcgct ctcctgttcc   7380
gaccctgccg cttaccggat acctgtccgc ctttctccct tcgggaagcg tggcgctttc   7440
tcatagctca cgctgtaggt atctcagttc ggtgtaggtc gttcgctcca agctgggctg   7500
tgtgcacgaa ccccccgttc agcccgaccg ctgcgcctta tccggtaact atcgtcttga   7560
gtccaacccg gtaagacacg acttatcgcc actggcagca gccactggta acaggattag   7620
cagagcgagg tatgtaggcg gtgctacaga gttcttgaag tggtggccta actacggcta   7680
cactagaagg acagtatttg gtatctgcgc tctgctgaag ccagttacct tcggaaaaag   7740
agttggtagc tcttgatccg gcaaacaaac caccgctggt agcggtggtt tttttgtttg   7800
caagcagcag attacgcgca gaaaaaaagg atctcaagaa gatcctttga tcttttctac   7860
ggggtctgac gctcagtgga acgaaaactc acgttaaggg attttggtca tgagattatc   7920
aaaaaggatc ttcacctaga tccttttaaa ttaaaaatga agttttaaat caatctaaag   7980
tatatatgag taaacttggt ctgacagtta ccaatgctta atcagtgagg cacctatctc   8040
agcgatctgt ctatttcgtt catccatagt tgcctgactc cccgtcgtgt agataactac   8100
gatacgggag ggcttaccat ctggccccag tgctgcaatg ataccgcgag acccacgctc   8160
accggctcca gatttatcag caataaacca gccagccgga agggccgagc gcagaagtgg   8220
tcctgcaact ttatccgcct ccatccagtc tattaattgt tgccgggaag ctagagtaag   8280
tagttcgcca gttaatagtt tgcgcaacgt tgttgccatt gctacaggca tcgtggtgtc   8340
acgctcgtcg tttggtatgg cttcattcag ctccggttcc caacgatcaa ggcgagttac   8400
atgatccccc atgttgtgca aaaaagcggt tagctccttc ggtcctccga tcgttgtcag   8460
aagtaagttg gccgcagtgt tatcactcat ggttatggca gcactgcata attctcttac   8520
tgtcatgcca tccgtaagat gcttttctgt gactggtgag tactcaacca agtcattctg   8580
agaatagtgt atgcggcgac cgagttgctc ttgcccggcg tcaatacggg ataataccgc   8640
gccacatagc agaactttaa aagtgctcat cattggaaaa cgttcttcgg ggcgaaaact   8700
ctcaaggatc ttaccgctgt tgagatccag ttcgatgtaa cccactcgtg cacccaactg   8760
atcttcagca tcttttactt tcaccagcgt ttctgggtga gcaaaaacag gaaggcaaaa   8820
tgccgcaaaa aagggaataa gggcgacacg gaaatgttga atactcatac tcttcctttt   8880
tcaatattat tgaagcattt atcagggtta ttgtctcatg agcggataca tatttgaatg   8940
tatttagaaa aataaacaaa taggggttcc gcgcacattt ccccgaaaag tgccacctga   9000
ctgccgggcc tcttgcggga tcaaaagaaa aacgaaatga tacaccaatc agtgcaaaaa   9060
aagatataat gggagataag acggttcgtg ttcgtgctga cttgcaccat atcataaaaa   9120
```

```
tcgaaacagc aaagaatggc ggaaacgtaa aagaagttat ggaaataaga cttagaagca   9180
aacttaagag tgtgttgata gtgcagtatc ttaaaatttt gtataatagg aattgaagtt   9240
aaattagatg ctaaaaattt gtaattaaga aggagtgatt acatgaacaa aaatataaaa   9300
tattctcaaa actttttaac gagtgaaaaa gtactcaacc aaataataaa acaattgaat   9360
ttaaaagaaa ccgataccgt ttacgaaatt ggaacaggta aagggcattt aacgacgaaa   9420
ctggctaaaa taagtaaaca ggtaacgtct attgaattag acagtcatct attcaactta   9480
tcgtcagaaa aattaaaact gaatactcgt gtcactttaa ttcaccaaga tattctacag   9540
tttcaattcc ctaacaaaca gaggtataaa attgttggga gtattcctta ccatttaagc   9600
acacaaatta ttaaaaaagt ggtttttgaa agccatgcgt ctgacatcta tctgattgtt   9660
gaagaaggat tctacaagcg taccttggat attcaccgaa cactagggtt gctcttgcac   9720
actcaagtct cgattcagca attgcttaag ctgccagcgg aatgctttca tcctaaacca   9780
aaagtaaaca gtgtcttaat aaaacttacc cgccatacca cagatgttcc agataaatat   9840
tggaagctat atacgtactt tgtttcaaaa tgggtcaatc gagaatatcg tcaactgttt   9900
actaaaaatc agtttcatca agcaatgaaa cacgccaaag taaacaattt aagtaccgtt   9960
acttatgagc aagtattgtc tatttttaat agttatctat tatttaacgg gaggaaataa  10020
ttctatgagt ccctaggggt tccgcgcaca tttccccgaa aagtgccacc tgaacgaagc  10080
atctgtgctt cattttgtag aacaaaaatg caacgcgaga gcgctaattt ttcaaacaaa  10140
gaatctgagc tgcattttta cagaacagaa atgcaacgcg aaagcgctat tttaccaacg  10200
aagaatctgt gcttcatttt tgtaaaacaa aaatgcaacg cgagagcgct aatttttcaa  10260
acaaagaatc tgagctgcat ttttacagaa cagaaatgca acgcgagagc gctattttac  10320
caacaaagaa tctatacttc ttttttgttc tacaaaaatg catcccgaga gcgctatttt  10380
tctaacaaag catcttagat tacttttttt ctcctttgtg cgctctataa tgcagtctct  10440
tgataacttt ttgcactgta ggtccgttaa ggttagaaga aggctacttt ggtgtctatt  10500
ttctcttcca taaaaaaagc ctgactccac ttcccgcgtt tactgattac tagcgaagct  10560
gcgggtgcat tttttcaaga taaaggcatc cccgattata ttctataccg atgtggattg  10620
cgcatacttt gtgaacagaa agtgatagcg ttgatgattc ttcattggtc agaaaattat  10680
gaacggtttc ttctattttg tctctatata ctacgtatag gaaatgttta cattttcgta  10740
ttgttttcga ttcactctat gaatagttct tactacaatt tttttgtcta aagagtaata  10800
ctagagataa acataaaaaa tgtagaggtc gagtttagat gcaagttcaa ggagcgaaag  10860
gtggatgggt aggttatata gggatatagc acagagatat atagcaaaga gatacttttg  10920
agcaatgttt gtggaagcgg tattcgcaat attttagtag ctcgttacag tccggtgcgt  10980
ttttggtttt ttgaaagtgc gtcttcagag cgcttttggt tttcaaaagc gctctgaagt  11040
tcctatactt tctagagaat aggaacttcg gaataggaac ttcaaagcgt ttccgaaaac  11100
gagcgcttcc gaaaatgcaa cgcgagctgc gcacatacag ctcactgttc acgtcgcacc  11160
tatatctgcg tgttgcctgt atatatatat acatgagaag aacggcatag tgcgtgttta  11220
tgcttaaatg cgtacttata tgcgtctatt tatgtaggat gaaaggtagt ctagtacctc  11280
ctgtgatatt atcccattcc atgcggggta tcgtatgctt ccttcagcac taccctttag  11340
ctgttctata tgctgccact cctcaattgg attagtctca tccttcaatg ctatcatttc  11400
ctttgatatt ggatcatact aagaaaccat tattatcatg acattaacct ataaaaatag  11460
gcgtatcacg aggccctttc gtctcgcgcg tttcggtgat gacggtgaaa acctctgaca  11520
```

catgcagctc ccggagacgg tcacagcttg tctgtaagcg gatgccggga gcagacaagc 11580
ccgtcagggc gcgtcagcgg gtgttggcgg gtgtcggggc tggcttaact atgcggcatc 11640
agagcagatt gtactgagag tgcaccatac cacagctttt caattcaatt catcattttt 11700
tttttattct tttttttgat ttcggtttct ttgaaatttt tttgattcgg taatctccga 11760
acagaaggaa gaacgaagga aggagcacag acttagattg gtatatatac gcatatgtag 11820
tgttgaagaa acatgaaatt gcccagtatt cttaacccaa ctgcacagaa caaaaacctg 11880
caggaaacga agataaatca tgtcgaaagc tacatataag gaacgtgctg ctactcatcc 11940
tagtcctgtt gctgccaagc tatttaatat catgcacgaa aagcaaacaa acttgtgtgc 12000
ttcattggat gttcgtacca ccaaggaatt actggagtta gttgaagcat taggtcccaa 12060
aatttgttta ctaaaaacac atgtggatat cttgactgat tttccatgg agggcacagt 12120 taagccgcta aaggcattat ccgccaagta caatttttta ctcttcgaag acagaaaatt 12180
tgctgacatt ggtaatacag tcaaattgca gtactctgcg ggtgtataca gaatagcaga 12240
atgggcagac attacgaatg cacacggtgt ggtgggccca ggtattgtta gcggtttgaa 12300
gcaggcggca gaagaagtaa caaaggaacc tagaggcctt ttgatgttag cagaattgtc 12360
atgcaagggc tccctatcta ctggagaata tactaagggt actgttgaca ttgcgaagag 12420
cgacaaagat tttgttatcg gctttattgc tcaaagagac atgggtggaa gagatgaagg 12480
ttacgattgg ttgattatga cacccggtgt gggtttagat gacaagggag acgcattggg 12540
tcaacagtat agaaccgtgg atgatgtggt ctctacagga tctgacatta ttattgttgg 12600
aagaggacta tttgcaaagg gaagggatgc taaggtagag ggtgaacgtt acagaaaagc 12660
aggctgggaa gcatatttga gaagatgcgg ccagcaaaac taaaaaactg tattataagt 12720
aaatgcatgt atactaaact cacaaattag agcttcaatt taattatatc agttattacc 12780
ctatgcggtg tgaaataccg cacagatgcg taaggagaaa ataccgccct aggcccaact 12840
aactcaacg 12849

<210> SEQ ID NO 30
<211> LENGTH: 9367
<212> TYPE: DNA
<213> ORGANISM: Artificial Sequence
<220> FEATURE:
<223> OTHER INFORMATION: plasmid

<400> SEQUENCE: 30
aaaaataatg gccctaggga tatacaattt ttaaaaaata tagctaatct tgcataaact 60
atataataaa tctaatttta gaatgtataa tttaaagggt tatggctgta tatagtcata 120
acccttatat ttcattaatt aaagttaaat tttgtatatt caaaaagctc ttgatattta 180
cggcagagcc accatataga gatgcctcag accctaatga tgaaatttct atatttattc 240
ctttgttaaa agagctaact aacatatctt ttgtaatctg taatatctca gggatatcac 300
taattatttg gctatttaaa tatattattt caggagcata agttgtaata gcattattta 360
tagctattgt taagtaacta caaaactcat gaataacttt tttggcattc tggttatctt 420
cataatatag ttgctttact atatcagaat ctattttagg aatattttct aaagaagaaa 480
gctgttcaaa tacctttttt tctgaacaat actgttctaa acagccacga tttccacaag 540
gacatagttt accattaggc atgatgatag tgtgaccaat ttctccactc ataccatttc 600
tgccactata taatttatta tttattataa tgcctgaacc aaatccactg tgaatactga 660

-continued

```
gactaagtag tgagttatgt acagttgaaa aagtattctc agctaaagct gttaagtttg    720
cttcattttc tatgtgaata ggaaagtcat actttttgct aaggatgcta tataagtcaa    780
tctcattaag attgtaatat ggagtaaaca atactttatt ttcacaagta atcccatgta    840
tagccaaagt aagaccaatt accttataag gagtgtctat tttggatatg ttataactat    900
ttataatttc atctatcaat tgtataacat tgtctttact tacttgtata tctgttaatt    960
tcttagaatt tataatagtt ccatctaagt aagatagaga agaaaatata tagtcgtatc   1020
caatgtccat acttaaagaa atccctgcac atttattaaa tactaataat atgggttttc   1080
ttccgccact atgagtacta tttccaattc ctatttcatg aactagagat tcatcaataa   1140
gtttttggt aatagcggat atagttgctt tattcaatcc tatagtagaa gctatacttg   1200
ccctagaaat aggaccattt tttataattt gttcaagtac caatctttca ttcatttctc   1260
gaatagtgta tttatcagta accaatttga tattcctcct taaaataata ttgtaatact   1320
ttttacacaa aaataaaagg ttattttgca ttgacaaaga taattaaata ttttattatt   1380
agttcataag ttagtttaat atactaacaa aaataaagca agtaaaatat acctaaaata   1440
taaaaaaatt aggataggaa aacgatagtt atgaagtggc attcaaggag tatggaaaaa   1500
ctcaagttta tgcttgtttt agagctagaa atagcaagtt aaaataaggc tagtccgtta   1560
tcaacttgaa aaagtggcac cgagtcggtg cttttaaagt attgttaaaa ataactctgt   1620
agaattataa attagttcta cagagttatt ttttaaaaaa attcaagctt gcatgcctgc   1680
aggccatttt agctaaggat atctataatg aaaagattta gaggaggaat aatttatgaa   1740
aaagattttt gtacttggag caggaacaat gggtgctggt atcgttcaag cattcgctca   1800
aaaaggttgt gaagtaattg taagagacat aaaggaagaa tttgttgaca gaggaatagc   1860
tggaatcact aaaggattag aaaagcaagt tgctaaagga aaaatgtctg aagaagataa   1920
agaagctata ctttcaagaa tttcaggaac aactgatatg aaattagctg ctgactgtga   1980
tttagtagtt gaagctgcaa tcgaaaacat gaaaattaag aaggaaatct tcgctgaatt   2040
agatggaatt tgtaagccag aagcgatttt agcttcaaac acttcatctt tatcaattac   2100
tgaagttgct tcagctacaa agagacctga taaagttatc ggaatgcatt tctttaatcc   2160
agctccagta atgaagcttg ttgaaattat taaaggaata gctacttctc aagaaacttt   2220
tgatgctgtt aaggaattat cagttgctat tggaaaagaa ccagtagaag ttgcagaagc   2280
tccaggattc gttgtaaaca gaatattaat cccaatgatt aacgaagctt catttatcct   2340
acaagaagga atagcttcag ttgaagatat tgatacagct atgaaatatg gtgctaacca   2400
tccaatggga cctttagctt taggagatct tattggatta gacgtttgct tagctatcat   2460
ggatgtttta ttcactgaaa caggtgataa caagtacaga gctagcagca tattaagaaa   2520
atatgttaga gctggatggc ttggaagaaa atcaggaaaa ggattctatg attactctaa   2580
ataatatcat gaatatatgg aaaaactcaa gtttatgctt caaactgctt cccctaattc   2640
cccattttta tatatatttg tattaaatta actttaatgt tacaatgttc ttagtatatt   2700
ttccttaata ttacattagt tctataaact ttattgttct taatatttaa ataaaatcca   2760
tgaagggagg aaaaaactat cttttaaaag tttatagtaa ataaaaaaaa attattaatg   2820
taaaaatata ctaagtatag aatatttata ataggggta ttaacttgtt ttcaaaaatc   2880
aaaaaaatta attttttaa aaaaacattt tcttttttaa ttgctgttgt aatgatgttg   2940
tttacagtat taggaacaaa tacttataaa gctgaagctg caagtggtgg tgcctgggct   3000
caatgtggag gtgaaaactt ccatggtgat aaatgttgtg tttccggtca cacttgtgtt   3060
```

```
agtattaacc aatggtattc acaatgtcaa ccaggaggtg ctccaagcaa taatgcttca   3120
aacaataata ataacaataa caataataac aacaacaata ataacaacaa caataatcac   3180
aacaacaaca acaataacaa caataacaat aacaatggtg gtagtggtag tactaaaaac   3240
ttcttcgata accaaattta tgctaaccca aagtttattg aagaagtcaa ttcttctatt   3300
ccaagattaa gttatgattt acaacaaaag gctcaaaagg ttaagaatgt tccaactgcc   3360
gtttggttag cttgggatgg agccactgga gaagttgctc aacatcttaa agctgctggt   3420
tctaaaactg ttgtcttcat catgtacatg attccaactc gtgattgtaa cgctaatgcc   3480
tctgctggtg gtgctggtaa cctcaacact tacaagggat acgttgataa tattgctaga   3540
actattcgta gttatccaaa ttcaaaggtt gttatgattc ttgaaccaga tactcttggt   3600
aaccttgtta ctgctaatag tgctaactgt caaaacgttc gtaacttaca taagaatgct   3660
ttatcttatg gtgttaatgt tttcggtagc atgagtaatg ttagtgttta ccttgatgct   3720
gctcatggtg cttggttagg tagctctact gataaggttg cttctgttgt taaggaaatc   3780
ttaaataatg ctccaaatgg aaagattcgt ggtttaagta ctaacatttc taactaccaa   3840
tcaatttctt ctgaatacca ataccaccaa aaacttgcct ctgctcttgc tgctgtcggt   3900
gttccaaaca tgcacttcat tgttgatact ggtcgtaatg gtgttactat taattctgga   3960
acatggtgta acttagtcgg tactggtctt ggtgaacgtc caagaggtaa tccaaatgct   4020
ggtatgccat tattagatgc ttacatgtgg cttaagactc caggagaatc tgacggttca   4080
tcctctggtt ctagagctga tccaaattgt tctagtaatg attctcttag aggtgctcca   4140
gatgctggtc aatggttcca tgattacttc gctcaattag taagaaatgc tagaccatca   4200
ttttaagcaa atttctaaat gattgaattt aacaaaaatt actaatctag aggatccccg   4260
ggtaccgagc tcgaattcgt aatcatggaa atatataaat aactactaga ttacataaat   4320
aagtttaaat taaagaatat tgtaaaattc aacaaaacat tttattactg ttaagtaagt   4380
gatataatat attaaataat aactattttc ttaagattaa ttgtataatt taattgaata   4440
ttggatatta aaaaaataaa tagttaaaaa atatgatata ggtggtacac atcagaaaat   4500
gggcaatata aactgtgaca taatctttag aaaaaaactt tagtgtagaa tatattattt   4560
aaagaagaat atatgaatga aataagttaa aactaaggtt gatatgatat tatgtttatc   4620
aatgatttta ctaaaaagat aaaaatatat tttgaatatt cataatcaaa gggtagggtt   4680
catcaatatg catattagat tatgagatga tgcaaactaa ataattttat actgtaaggg   4740
agacggataa taaaatggat tataaatctg tagaatttta tgataattat ttaataataa   4800
aagaattaag aaattttaaa ttaaaacata tatttgagtg cggacagatt tttaggtttg   4860
aagaggtagc agaaaatgat tttattgtaa ttgcgtttgg aagattaatt gaagttaaag   4920
aagatggaaa tgacgtaata atttataatt ctacaaagga agattttaaa aatatttggc   4980
ttaagtattt tgatttagat agagattact cagttataaa agatgaactt tcaaaagatg   5040
ttttacttaa acaaagtatt gaatttggat atggtgttag agtcttgaat caagatccat   5100
ttgaaatgtt gcttagcttt attatttcag cgcgaaataa tataccatca ataaagaaga   5160
ctgtaaataa aatatctaat aaatggggaa aagaaattat ttataaggat aaaacctact   5220
atgcgtttcc taatataggt gaaataaaag atgctacact agaagaaata caggagacag   5280
gagcatcttc catggacgcg tgacgtcgac tctagaaatt cttctaaata taagaatatt   5340
ttaaagaaat atctttatat attagttatt aaaatttata agattataag aaacattata   5400
```

-continued

```
acatatttta gaacttttta actattctaa aagattaatt tacatattaa catttaatta   5460
tgggtaaaaa ctattttgaa aaatgattta tatggaatta tgtttcttaa atatacaatc   5520
atgtttcatg aatacataat tattttaaat gtattgggag ggtaaattga ttgtgaaacg   5580
cggcgatgtt tattttgctg atttatctcc tgttgttggc tcagagcaag gcggggtgcg   5640
cccggtttta gtgatccaaa atgacatcgg aaatcgcttc agcccaactg ctattgttgc   5700
agccataaca gcacaaatac agaaagcgaa attaccaacc cacgtcgaaa tcgatgcaaa   5760
acgctacggt tttgaaagag attccgttat tttgctggag caaattcgga cgattgacaa   5820
gcaaaggtta acggataaga ttactcatct ggatgatgaa atgatggata aggttgatga   5880
agccttacaa atcagtttgg cactcattga tttttagaca tatttgcagg ttgctcaaat   5940
agagcgaaag aacatgtgag caaaaggcca gcaaaaggcc aggaaccgta aaaaggccgc   6000
gttgctggcg tttttccata ggctccgccc ccctgacgag catcacaaaa atcgacgctc   6060
aagtcagagg tggcgaaacc cgacaggact ataaagatac caggcgtttc cccctggaag   6120
ctccctcgtg cgctctcctg ttccgaccct gccgcttacc ggatacctgt ccgcctttct   6180
cccttcggga agcgtggcgc tttctcatag ctcacgctgt aggtatctca gttcggtgta   6240
ggtcgttcgc tccaagctgg gctgtgtgca cgaacccccc gttcagcccg accgctgcgc   6300
cttatccggt aactatcgtc ttgagtccaa cccggtaaga cacgacttat cgccactggc   6360
agcagccact ggtaacagga ttagcagagc gaggtatgta ggcggtgcta cagagttctt   6420
gaagtggtgg cctaactacg gctacactag aagaacagta tttggtatct gcgctctgct   6480
gaagccagtt accttcggaa aaagagttgg tagctcttga tccggcaaac aaaccaccgc   6540
tggtagcggt ggtttttttg tttgcaagca gcagattacg cgcagaaaaa aaggatctca   6600
agaagatcct ttgatctttt ctacggggtc tgacgctcag tggaacgaaa actcacgtta   6660
agggattttg gtcatgagat tatcaaaaag gagtttaaac ttctaaaatc tgattaccaa   6720
ttagaatgaa tatttcccaa atattaaata ataaaacaaa aaaattgaaa aaagtgtttc   6780
caccattttt tcaatttttt tataattttt ttaatctgtt atttaaatag tttatagtta   6840
aatttacatt ttcattagtc cattcaatat tctctccaag ataactacga actgctaaca   6900
aaattctctc cctatgttct aatggagaag attcagccac tgcatttccc gcaatatctt   6960
ttggtatgat tttacccgtg tccatagtta aaatcatacg gcataaagtt aatatagagt   7020
tggtttcatc atcctgataa ttatctatta attcctctga cgaatccata atggctcttc   7080
tcacatcaga aaatggaata tcaggtagta attcctctaa gtcataattt ccgtatattc   7140
ttttattttt tcgttttgct tggtaaagca ttatggttaa atctgaattt aattccttct   7200
gaggaatgta tccttgttca taaagctctt gtaaccattc tccataaata aattcttgtt   7260
tgggaggatg attccacggt accatttctt gctgaataat aattgttaat tcaatatatc   7320
gtaagttgct tttatctcct attttctttg aaataggtct aattttttgt ataagtattt   7380
ctttactttg atctgtcaat ggttcagata cgacgactaa aaagtcaaga tcactatttg   7440
gttttagtcc actctcaact cctgatccaa acatgtaagt accaataagg ttattttttta   7500
aatgtttccg aagtattttt ttcactttat taatttgttc gtatgtattc aaatatatcc   7560
tcctcactat tttgattagt acctatttta tatccatagt tgttaattaa ataaacttaa   7620
tttagtttat ttatagattt cattggcttc taaatttttt atctagataa taattatttt   7680
agttaatttt attctagatt atatatgata tgatctttca tttccataaa actaaagtaa   7740
gtgtaaacct attcattggg ccggccgctt ataatccata acaatcatcc tttctgtgac   7800
```

-continued actgtcagac acttatcaca ttaagtatat actattatta aactattcta tatacttaat 7860
ttattttaat agaaaaacat aatatcataa taacttcaaa attaaacttt atttatgatt 7920
tcatacttga ctttgatttt agaaaggata tactttttag cagatttgga aacggctttg 7980
gacgtagttt gcccatagat gaacaaacaa actacatcca aaaattatac ttttcccttc 8040
attggtatcc gtatttttac atcttaatag cgtatgtatt acaacacacc taaacaacga 8100
ccttacggtc tgctactgca tatcctagct tgattgttta gttgcctcaa ctatgcttaa 8160
ccctaccccg aactcttttt ttattgtggg ttttcgtcgt gaagtcccac cgacacataa 8220
tcataacata agatgtatta tgaaaatgcg agtgactatc cttttgtatc ggctcactac 8280
accacagata tattttttag tgcatactgt gtcggcactc tcaatattaa attaataaat 8340
aaattatttt ttctttttac tcttctttac atgagctttt ttaaagctcc ttgcataata 8400
tttaatgcat gtacgttctt ttttctgttc ttcctctgta aaacatctca tttttatggc 8460
acaccatcca tatcggttca tctttgaaca attaatacat tggactttcc ctttatgtaa 8520
acatcttgac tcattgtatt tactgcaata ggttgctact gttttatcat gaatcatcaa 8580
cgaatgtatt ttgcatattt cagtatcttt aataaactct ttgcaatttt tacaagtttt 8640
catatacgcc cttcttttca taaattaatt tatgaattct atgtattcca aggagctttt 8700
taaagctccc cctttcgtac tacttagcta caagcactat aaaagtcata atgtttactg 8760
ctaaagtcaa taatgatatt gctaatacct tgttatttga taagatactg ctttcctctg 8820
tcactttgct cacccccttt cattttcata aattaattat gaaaaaataa atatacttct 8880
aatttttatc aaataaaaaa gcctttgcgt actgcttcca atacacaaag gctataaact 8940
tctaaatctt acttattgca atttacattt atatctgtta agataatctc ataaattgaa 9000
tatatatagt taatgtttct cttgtatgtc ggtacatttg aaatattgct atagatagag 9060
ttctctaacg gcttgatgtg ttggtagcac atttaagttt tggcttatat actaagttgg 9120
tagcttaata tataagagct gaggacttat tttttatta aatttttcaa cttgtctata 9180
ttttaacccg taattgaata cataacaagt attttttttt gtattcaatt aaacattcat 9240
aaatgagtat aattaatcat actaaattct ataattttct tttctgtaaa tttctttcta 9300
ttcagcactg ttatgccttt tgactatcac ttaataaaaa ataagaaatg aattgtcaat 9360
tgttcaa 9367

<210> SEQ ID NO 31
<211> LENGTH: 25
<212> TYPE: DNA
<213> ORGANISM: Artificial Sequence
<220> FEATURE:
<223> OTHER INFORMATION: primer

<400> SEQUENCE: 31
agataattat gaagttaatc cttag 25

<210> SEQ ID NO 32
<211> LENGTH: 27
<212> TYPE: DNA
<213> ORGANISM: Artificial Sequence
<220> FEATURE:
<223> OTHER INFORMATION: primer

<400> SEQUENCE: 32
catttgcttt caggtcttct tttgctg 27

GENETIC TOOL FOR THE TRANSFORMATION OF *CLOSTRIDIUM* BACTERIA

CROSS-REFERENCE TO RELATED APPLICATION

This application is the U.S. national stage application of International Patent Application No. PCT/FR2016/052663, filed Oct. 14, 2016.

The Sequence Listing for this application is labeled "2M00390.txt" which was created on May 10, 2018 and is 137,760 bytes. The entire content of the sequence listing is incorporated herein by reference in its entirety.

The present invention relates to a genetic tool comprising at least two different nucleic acids allowing the transformation by homologous recombination of a bacterium of the genus *Clostridium*, typically of a solventogenic bacterium of the genus *Clostridium.*

TECHNOLOGICAL BACKGROUND

The bacteria belonging to the genus *Clostridium*, phylum Firmicutes, are obligate anaerobic Gram-positive bacilli capable of forming endospores. This genus contains numerous species studied on account of their pathogenic nature or their industrial and medical interest. For example, *Clostridium tetani, Clostridium botulinum, Clostridium perfringens* and *Clostridium difficile* are the agents responsible for tetanus, botulism, gas gangrene and pseudomembranous colitis, respectively. In parallel, other species such as *Clostridium acetobutylicum, Clostridium butyricum* and *Clostridium beijerinckii*, which are non-pathogenic to humans, are used in fermentation. Lastly, *Clostridium novyi* and *Clostridium sporogenes* have recently been used in studies aimed at the development of anti-cancer therapies.

The *Clostridium* species of industrial interest are capable of producing solvents from a wide variety of sugars and substrates ranging from glucose to cellulose. The solvent-producing *Clostridium* bacteria are characterized by diauxic growth. Acids (acetic and butyric) are produced during the exponential growth phase. Then, when cell growth ceases and the bacteria enter the stationary phase, they produce solvents.

Most solventogenic *Clostridium* strains produce acetone, butanol and ethanol as final products. These strains are called "ABE strains". This is for example the case of strains *C. acetobutylicum* ATCC824 and *C. beijerinckii* NCIMB 8052. Other strains are also able to reduce acetone to isopropanol, and are called "IBE strains". This is the case for example of strain *C. beijerinckii* DSM 6423 (NRRL B593) which has in its genome an adh gene encoding a primary/secondary alcohol-dehydrogenase which allows the reduction of acetone to isopropanol.

Isopropanol production by *C. acetobutylicum* ATCC824 is possible after introduction of a plasmid for expressing the adh gene from *C. beijerinckii* DSM 6423. Such a genetically modified strain performs in the same way as strain DSM 6423. This performance can be improved after overexpression within an operon structure of the ctfA, ctfB and adc genes encoding the CoA-transferases involved in the reassimilation of acids, and acetoacetate decarboxylase, respectively (Collas et al., 2012). The introduction of a plasmid containing these genes modifies the fermentation profile of strain ATCC824 to produce an IBE mixture. However, the presence of antibiotic in the growth medium is required to maintain this genetic construction, making it impossible to use this strain for industrial applications.

Despite the undeniable interest of bacteria of the genus *Clostridium*, little work has been done to study and/or modify their metabolism due to the difficulties of obtaining genetically modified strains. The most robust systems are based on homologous recombination events allowing precise and stable modification of the genome. The homologous recombination frequencies observed in *Clostridium* being very low, however, selection markers (e.g., an antibiotic resistance gene) and counter-selection markers (e.g., a gene encoding a toxin) proved to be necessary. Two tools have been recently developed (Al-Hinai et al., 2012; Cartman et al., 2012), each based on the use of a single plasmid. Although innovative, these systems have disadvantages. The first system has the drawback of leaving at the modification site an FRT cassette (used during excision of the selectable marker) that can alter the genetic context of the mutant and prevent re-use of the tool to carry out a great number of modifications. These drawbacks are well-known to persons skilled in the art. The second system, requiring two sequential homologous recombination events, cannot be used to modify essential regions of the genome. A tool involving the sequential use of two plasmids, one of them encoding the meganuclease I-SceI, which is capable of inducing breaks in double-stranded DNA at specific target sites and of promoting homologous recombination events, was then developed (Zhang et al., 2015). Here too, the modification of certain essential genes is made impossible by the need to carry out two sequential homologous recombination events. As of today, the latest generation of tools developed (Wang et al., 2015; Xu et al., 2015) is based on the CRISPR (Clustered Regularly Interspaced Short Palindromic Repeats) technology, which works in a manner similar to the RNA interference observed in eukaryotes (Barrangou et al., 2007). The tools described by Wang et al. and Xu et al., adapted to *C. beijerinckii* and *C. cellulolyticum*, respectively, are based on the use of a single plasmid. Xu et al. use a modified version of the Cas9 enzyme creating single-strand breaks instead of double-strand breaks. Both of the CRISPR technology-based tools available have the major disadvantage of significantly limiting the size of the nucleic acid of interest (and thus the number of coding sequences or genes) that can be inserted into the bacterial genome (about 1.8 kb at best according to Xu et al.).

SUMMARY OF THE INVENTION

The objective of the present invention is to provide a genetic tool adapted to the genus *Clostridium* as a whole, in particular to the solventogenic bacteria of the genus *Clostridium*, making it possible for the first time to modify the bacterial genome in order to allow the use of bacteria of the genus *Clostridium* on an industrial scale.

The invention thus relates to a genetic tool allowing the transformation by homologous recombination of a bacterium of the genus *Clostridium*, preferably a solventogenic bacterium of the genus *Clostridium*, characterized in that it comprises at least two different nucleic acids. This tool is for example capable of modifying a region of the genome of the bacterium of the genus *Clostridium* including a sequence essential to bacterial survival, or of allowing the insertion of large fragments of nucleic acid sequences, which is impossible using the existing tools.

A first object of the invention thus relates to a genetic tool allowing the transformation by homologous recombination of a solventogenic bacterium of the genus *Clostridium* characterized in that it comprises:

a first nucleic acid encoding at least Cas9, wherein the Cas9 coding sequence is placed under the control of a promoter, and at least a second nucleic acid containing a repair template allowing, by a homologous recombination mechanism, the replacement of a portion of the Cas9-targeted bacterial DNA by a sequence of interest, and in that i) at least one of said nucleic acids further encodes one or more guide RNAs (gRNAs), or ii) the genetic tool further comprises one or more guide RNAs, each guide RNA comprising a Cas9-enzyme-binding RNA structure and a sequence complementary to the targeted portion of the bacterial DNA.

The invention further relates to a process for transforming and/or genetically modifying by homologous recombination a bacterium of the genus *Clostridium*, typically a solventogenic bacterium of the genus *Clostridium*, characterized in that it comprises a step of introduction into the bacterium of a genetic tool according to the invention. The invention also relates to the bacteria of the genus *Clostridium* thus transformed and/or genetically modified.

The inventors also disclose a kit for transforming and/or genetically modifying a bacterium of the genus *Clostridium*, or for producing at least one solvent, for example a mixture of solvents, using a bacterium of the genus *Clostridium*, comprising the components of the genetic tool according to the invention, and optionally, in particular, one or more inducers adapted to the selected inducible promoter(s) used within the tool.

Also disclosed are the uses of the genetic tool according to the invention, of the process for transforming and/or genetically modifying by homologous recombination a bacterium of the genus *Clostridium*, of the bacterium thus transformed and/or genetically modified, for the production of a solvent or a mixture of solvents on an industrial scale, preferably acetone, butanol, ethanol, isopropanol or a mixture thereof, typically an isopropanol/butanol mixture.

DETAILED DESCRIPTION OF THE INVENTION

Figure 2:
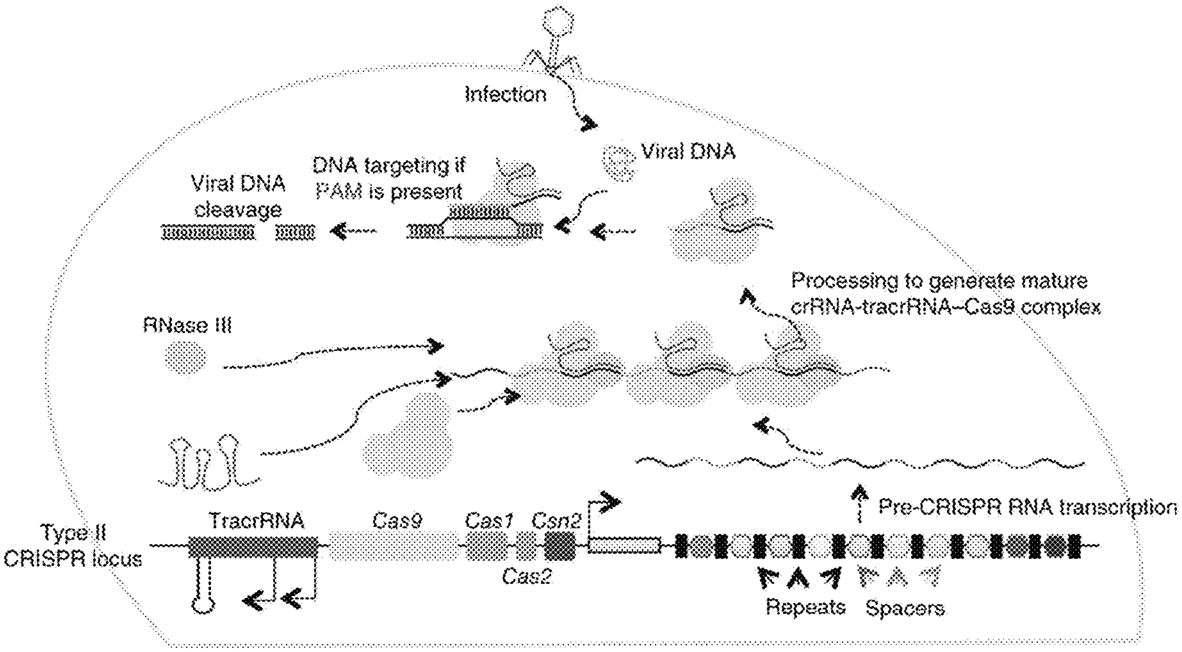

CRISPR (Clustered Regularly Interspaced Short Palindromic Repeats) refers in bacteria and archaea to loci of genes having an immune defence role against phages and plasmids. The CRISPR-Cas9 system is based essentially on the combination of a Cas9 protein inducing double-strand breaks in the target genome and of a guide RNA (gRNA) responsible for the specificity of the cleavage site. This ability to create targeted double-strand breaks in the DNA makes it possible to promote the homologous recombination events necessary to introduce mutations into the genome of the strains of interest. Cell viability depends on the integrity of the genome. The bacterium must repair any break in its DNA, whether by a non-homologous end joining mechanism, or by a homologous recombination mechanism requiring a repair template. By providing the cell such a template, it is then possible to modify the region corresponding to the break site (FIG. 2). The ability of CRISPR to make double-strand breaks in DNA molecules has allowed its recent use as a genetic tool in various organisms, in particular in *Streptococcus pyogenes*, in which it was first characterized, in *E. coli*, and within eukaryotic cells (Jiang et al., 2013; Cong et al., 2013; Hwang et al., 2013; Hsu et al., 2013). It was recently used in *Clostridium beijerinckii* and *Clostridium cellulolyticum* with the help of genetic tools which allowed only limited modification of the bacterial genome, which is impractical on an industrial scale (Wang et al., 2015; Xu et al., 2015).

A genetic tool allowing the transformation by homologous recombination of a bacterium of the genus *Clostridium* and comprising at least two different nucleic acids is for the first time disclosed in the present text. The inventors have demonstrated that this tool makes it possible to transform and/or genetically modify the solventogenic bacteria of the genus *Clostridium*, in a manner sufficiently effective to make them especially useful from an industrial perspective, thus meeting a long-expressed need.

A particular genetic tool according to the invention, allowing the transformation by homologous recombination of a bacterium of the genus *Clostridium*, comprises:

a first nucleic acid encoding at least Cas9, wherein the Cas9 coding sequence is placed under the control of a promoter, and at least a second nucleic acid containing a repair template allowing, by a homologous recombination mechanism, the replacement of a portion of the Cas9-targeted bacterial DNA by a sequence of interest, given that i) at least one of said nucleic acids further encodes one or more guide RNAs (gRNAs) or that ii) the genetic tool further comprises one or more guide RNAs. In this tool each guide RNA comprises a Cas9-enzyme-binding RNA structure and a sequence complementary to the targeted portion of the bacterial DNA.

The expression "bacterium of the genus *Clostridium*" is intended to mean in particular the *Clostridium* species of industrial interest, typically the solventogenic bacteria of the genus *Clostridium*. The expression "bacterium of the genus *Clostridium*" includes the wild-type bacteria as well as the strains derived therefrom genetically modified with the aim of improving their performance (for example overexpressing the ctfA, ctfB and adc genes) without having been exposed to the CRISPR system. The expression "*Clostridium* species of industrial interest" is intended to mean the species capable of producing, by fermentation, solvents from monosaccharides such as glucose, xylose, fructose or mannose, from polysaccharides such as cellulose or hemicelluloses, from acids such as butyric acid or acetic acid, or from any other carbon source assimilable and usable by the bacteria of the genus *Clostridium* (CO, $CO_2$ and methanol, for example). Examples of solventogenic bacteria of interest are the bacteria of the genus *Clostridium* which produce acetone, butanol, ethanol and/or isopropanol, such as the strains identified in the literature as "ABE strain" [strains which produce acetone, butanol and ethanol as fermentation products] and "IBE strain" [strains which produce isopropanol (by reduction of acetone), butanol and ethanol as fermentation products]. Solventogenic bacteria of the genus *Clostridium* can be selected from *C. acetobutylicum, C. cellulolyticum, C. phytofermentans, C. beijerinckii, C. saccharobutylicum, C. saccharoperbutylacetonicum, C. sporogenes, C. butyricum, C. aurantibutyricum* and *C. tyrobutyricum*, preferably from *C. acetobutylicum, C. beijerinckii, C. butyricum* and *C. tyrobutyricum* and *C. cellulolyticum*, and more preferably from *C. acetobutylicum* and *C. beijerinckii.*

In a particular embodiment, the bacterium of the genus *Clostridium* concerned is an "ABE strain", preferably strain *C. acetobutylicum* ATCC824 or strain *C. beijerinckii* NCIMB 8052.

In another particular embodiment, the bacterium of the genus *Clostridium* concerned is an "IBE strain", preferably strain *C. beijerinckii* DSM 6423 (also identified as strain NRRL B593).

The CRISPR system contains two distinct components, i.e., i) an endonuclease, in the present case the nuclease associated with the CRISPR system (Cas or "CRISPR-associated protein"), Cas9, and ii) a guide RNA. The guide RNA is in the form of a chimeric RNA which consists of the combination of a bacterial CRISPR RNA (crRNA) and a tracrRNA (trans-activating CRISPR RNA) (Jinek et al., Science 2012—see FIG. 3). The gRNA combines in a single transcript the targeting specificity of the crRNA corresponding to the "spacer sequences" which serve as guides for the Cas proteins, and the conformational properties of the tracrRNA. When the gRNA and the Cas9 protein are expressed simultaneously in the cell, the target genomic sequence can be permanently modified or interrupted.

The modification is advantageously guided by a repair template.

The genetic tool according to the invention comprises a first nucleic acid encoding at least Cas9. The term "Cas9" is intended to mean a Cas9 protein (also called Csn1 or Csx12) or a functional protein, peptide or polypeptide fragment thereof, "functional" meaning capable of interacting with the one or more guide RNAs and of carrying out the enzyme (nuclease) activity which enables it to create the double-strand break in the DNA of the target genome. "Cas9" can thus indicate a modified protein, for example truncated in order to remove the protein domains not essential to the predefined functions of the protein, in particular the domains not necessary for interaction with the one or more gRNAs.

The sequence encoding Cas9 (the entire protein or a fragment thereof) as used within the context of the invention can be obtained from any known Cas9 protein (Makarova et al., 2011). Examples of Cas9 proteins useful in the present invention include, but are not limited to, the Cas9 proteins from *Streptococcus pyogenes, Streptococcus thermophilus, Streptococcus mutans, Campylobacter jejuni, Francisella novicida* and *Neisseria meningitidis*. Other Cas9 proteins useful in the present invention are also described in the article by Fonfara et al., 2013.

In a particular embodiment, the Cas9 protein, or a functional protein, peptide or polypeptide fragment thereof, encoded by one of the nucleic acids of the genetic tool according to the invention comprises, or consists of, the amino acid sequence SEQ ID NO: 1, or any other amino acid sequence having at least 50%, preferably at least 60%, identity therewith, and containing at the least the two aspartic acids ("D") occupying positions 10 ("D10") and 840 ("D840") of the amino acid sequence SEQ ID NO: 1.

In a preferred embodiment, Cas9 comprises, or consists of, the Cas9 protein (NCBI accession number: WP_010922251.1, SEQ ID NO: 1), encoded by the cas9 gene from strain *Streptococcus pyogenes* M1 GAS (NCBI accession number: NC_002737.2 SPy_1046, SEQ ID NO: 2) or a version thereof having undergone optimization ("optimized version") giving rise to a transcript containing the codons used preferentially by the bacteria of the genus *Clostridium*, typically the codons rich in adenine ("A") and thymine ("T") bases, allowing facilitated expression of the Cas9 protein within this bacterial genus. These optimized codons respect the codon usage bias, well-known to persons skilled in the art, specific to each bacterial strain.

In the peptide sequences disclosed in this document, the amino acids are represented by their single-letter code according to the following nomenclature: C: cysteine; D: aspartic acid; E: glutamic acid; F: phenylalanine; G: glycine; H: histidine; I: isoleucine; K: lysine; L: leucine; M: methionine; N: asparagine; P: proline; Q: glutamine; R: arginine; S: serine; T: threonine; V: valine; W: tryptophan and Y: tyrosine.

According to a particular embodiment, the Cas9 domain consists of an entire Cas9 protein, preferably the Cas9 protein from *Streptococcus pyogenes*, or an optimized version thereof.

The Cas9 coding sequence present within one of the nucleic acids of the genetic tool according to the invention is placed under the control of a promoter. This promoter can be a constitutive promoter or an inducible promoter. In a preferred embodiment, the promoter controlling Cas9 expression is an inducible promoter.

Examples of constitutive promoters useful within the context of the present invention can be selected from the promoter of the thl gene, of the ptb gene, of the adc gene, of the BCS operon, or a derivative thereof, preferably a functional but shorter (truncated) derivative such as the "miniPthl" derivative of the thl gene promoter from *C. acetobutylicum* (Dong et al., 2012), or any other promoter well-known to persons skilled in the art, allowing the expression of a protein within *Clostridium.*

Examples of inducible promoters useful within the context of the present invention can be selected for example from a promoter whose expression is controlled by the transcriptional repressor TetR, for example the promoter of the tetA gene (tetracycline resistance gene originally present on the *E. coli* transposon Tn10); a promoter whose expression is controlled by L-arabinose, for example the promoter of gene ptk (see Zhang J. et al., 2015), preferably in combination with the araR regulator expression cassette from *C. acetobutylicum* in order to construct an ARAi system (see Zhang J. et al., 2015); a promoter whose expression is controlled by laminaribiose (β-1,3 glucose dimer), for example the celC gene promoter, preferably immediately followed by the repressor gene glyR3 and the gene of interest (see Mearls E B et al. (2015)) or the celC gene promoter (see Newcomb M. et al., 2011); a promoter whose expression is controlled by lactose, for example the bgaL gene promoter, preferably immediately followed by the AdhE1 (aldehyde/alcohol dehydrogenase) gene (see Banerjee et al., 2014); a promoter whose expression is controlled by xylose, for example the xylB gene promoter (see Nariya H et al., 2011); and a promoter whose expression is controlled by UV exposure, for example the bcn promoter (see Dupuy et al., 2005).

A promoter derived from one of the promoters described above, preferably a functional but shorter (truncated) derivative can also be advantageously used in the context of the invention.

Other inducible promoters useful in the present invention are also described for example in the articles by Ransom E M et al. (2015), Currie D H et al. (2013), D'Urzo N et al. (2013) and Hartman A H et al. (2011).

A preferred inducible promoter is an anhydrotetracycline (aTc)-inducible promoter derived from tetA (aTc is less toxic than tetracycline and capable of releasing the inhibition of the transcriptional repressor TetR at lower concentration), selected from Pcm-2tetO1 and Pcm-2tetO2/1 (Dong et al., 2012).

Another preferred inducible promoter is a xylose-inducible promoter derived from xylB, for example the xylB promoter from *Clostridium dificile* 630 (Nariya et al., 2011).

The inducible promoters as disclosed in the present invention make it possible to advantageously control the action of the enzyme and to facilitate the selection of transformants having undergone the desired genetic modifications.

The term "guide RNA" or "gRNA" refers within the meaning of the invention to an RNA molecule capable of interacting with "Cas9" in order to guide it towards a target region of the bacterial chromosome. The specificity of the break is determined by the gRNA. As explained above, each gRNA comprises two regions:

- a first region (commonly called the "SDS" region), at the 5' end of the gRNA, which is complementary to the target chromosomal region and which imitates the crRNA of the endogenous CRISPR system, and
- a second region (commonly called the "handle" region), at the 3' end of the gRNA, which mimics the base-pairing interactions between the tracrRNA (trans-activating crRNA) and the crRNA of the endogenous CRISPR system and has a double-stranded stem-loop structure ending in the 3' direction with an essentially single-stranded sequence. This second region is essential to the binding of the gRNA to Cas9.

The first region of the gRNA (SDS region) varies according to the targeted chromosomal sequence.

The SDS region of the gRNA which is complementary to the target chromosomal region comprises at least 1 nucleotide, preferably at least 1, 2, 3, 4, 5, 10, 15, 20, 25, 30, 35 or 40 nucleotides, typically between 1 and 40 nucleotides. Preferably, this region has a length of 20, 21, 22, 23, 24, 25, 26, 27, 28, 29 or 30 nucleotides.

The second region of the gRNA (handle region) has a stem-loop (or hairpin) structure. The handle regions of the different gRNAs do not depend on the selected chromosomal target.

According to a particular embodiment, the handle region comprises, or consists of, a sequence of at least 1 nucleotide, preferably at least 1, 50, 100, 200, 500 and 1000 nucleotides, typically between 1 and 1000 nucleotides. Preferably, this region has a length of 40 to 120 nucleotides.

The overall length of a gRNA is in general from 50 to 1000 nucleotides, preferably from 80 to 200 nucleotides, and more particularly preferably from 90 to 120 nucleotides. According to a particular embodiment, a gRNA as used in the present invention has a length ranging between 95 and 110 nucleotides, for example a length of about 100 or about 110 nucleotides.

Persons skilled in the art can easily define, by using well-known techniques, the sequence and the structure of the gRNAs according to the chromosomal region to be targeted (see for example the article by DiCarlo et al., 2013).

The targeted DNA region/portion/sequence within the bacterial chromosome can correspond to a portion of non-coding DNA or a portion of coding DNA. In a particular embodiment, the targeted portion of the bacterial DNA comprises one or more genes or gene portion(s) essential to bacterial survival or one or more genes or DNA sequences whose inactivation allows the selection of bacteria having integrated the nucleic acid(s) of interest.

Particular examples of a targeted DNA portion within a bacterium of the genus *Clostridium* are the sequences used in the experimental section. They are for example the sequences encoding the upp (SEQ ID NO: 3) and adhE1 (SEQ ID NO: 4) genes.

The targeted DNA region/portion/sequence is followed by a protospacer adjacent motif (PAM) sequence which plays a part in Cas9 binding.

The SDS region of given gRNA is 100% identical or at least 80% identical, preferably at least 85%, 90%, 95%, 96%, 97%, 98% or 99% identical to the targeted DNA region/portion/sequence within the bacterial chromosome and is capable of hybridizing with all or part of the complementary sequence of said region/portion/sequence, typically with a sequence comprising at least 1 nucleotide, preferably at least 1, 2, 3, 4, 5, 10, 15, 20, 25, 30, 35 or 40 nucleotides, typically between 1 and 40 nucleotides, preferably with a sequence comprising 20, 21, 22, 23, 24, 25, 26, 27, 28, 29 or 30 nucleotides.

In the process according to the invention, one or more gRNAs can be used simultaneously. These different gRNAs can target identical or different, preferably different, chromosomal regions.

The gRNAs can be introduced into the bacterial cell in the form of gRNA molecules (mature or precursors), in the form of precursors or in the form of one or more nucleic acids encoding said gRNAs. The gRNAs are preferably introduced into the bacterial cell in the form of one or more nucleic acids encoding said gRNAs.

When the one or more gRNAs are introduced into the cell directly in the form of RNA molecules, these gRNAs (mature or precursors) can contain modified nucleotides or chemical modifications allowing them, for example, to increase their resistance to nucleases and thus to increase their lifespan in the cell. They can in particular comprise at least one modified or unnatural nucleotide such as, for example, a nucleotide comprising a modified base, such as inosine, methyl-5-deoxycytidine, dimethylamino-5-deoxyuridine, deoxyuridine, diamino-2,6-purine, bromo-5-deoxyuridine or any other modified base allowing hybridization. The gRNAs used according to the invention can also be modified on the level of the internucleotide bond such as for example phosphorothioates, H-phosphonates or alkyl-phosphonates, or on the level of the backbone such as for example alpha-oligonucleotides, 2'-O-alkyl ribose or peptide nucleic acids (PNA) (Egholm et al., 1992).

The gRNAs can be natural RNAs, synthetic RNAs or RNAs produced by recombination techniques. Said gRNAs can be prepared by any methods known to persons skilled in the art such as, for example, chemical synthesis, transcription in vivo or amplification techniques.

When the gRNAs are introduced into the bacterial cell in the form of one or more nucleic acids, the one or more sequences encoding the one or more gRNAs are placed under the control of an expression promoter. Said promoter can be constitutive or inducible.

When several gRNAs are used, the expression of each gRNA can be controlled by a different promoter. Preferably, the promoter used is the same for all the gRNAs. The same promoter can in a particular embodiment be used to allow the expression of several, for example of only a few, of the gRNAs intended to be expressed.

In a preferred embodiment, the one or more promoters controlling the expression of the one or more gRNAs is/are constitutive promoters.

Examples of constitutive promoters useful within the context of the present invention can be selected from the promoter of the thl gene, of the ptb gene or of the bcs operon, or a derivative thereof, preferably miniPthl, or any other promoter, well-known to persons skilled in the art, allowing the synthesis of an RNA (coding or non-coding) within *Clostridium.*

Examples of inducible promoters useful within the context of the present invention can be selected from the promoter of the tetA gene, of the xylA gene, of the lacI gene, or of the bgaL gene, or a derivative thereof, preferably 2tetO1 or tetO2/1. A preferred inducible promoter is tetO2/1.

The promoters controlling the expression of Cas9 and of the one or more gRNAs can be identical or different and constitutive or inducible. In a particular and preferred embodiment of the invention, only one of the promoters controlling the expression of Cas9 or of the one or more gRNAs, respectively, is an inducible promoter.

The term "nucleic acid" is intended to mean, within the meaning of the invention, any natural, synthetic, semi-synthetic or recombinant DNA or RNA molecule, optionally chemically modified (i.e., comprising unnatural bases, modified nucleotides comprising for example a modified bond, modified bases and/or modified sugars), or optimized so that the codons of the transcripts synthesized from the coding sequences are the codons most frequently found in a bacterium of the genus *Clostridium* for use therein. As explained above, in the case of the genus *Clostridium*, the optimized codons are typically codons rich in adenine ("A") and thymine ("T") bases.

Each of the nucleic acids present within the genetic tool according to the invention, typically the "first" nucleic acid and the "second" nucleic acid, consists of a distinct entity and corresponds for example i) to an expression cassette (or "construction") such as a nucleic acid comprising at least one transcriptional promoter operably linked (with the meaning understood by persons skilled in the art) to one or more (coding) sequences of interest, typically to an operon comprising several coding sequences of interest whose expression products contribute to the creation of a function of interest within the bacterium, or such as a nucleic acid further comprising an activation sequence and/or transcription terminator; or ii) to a circular or linear, single- or double-stranded vector, for example a plasmid, a phage, a cosmid, an artificial or synthetic chromosome, comprising one or more expression cassettes as defined above. Preferably, the vector is a plasmid.

The expression cassettes and vectors can be constructed by conventional procedures well-known to persons skilled in the art and can comprise one or more promoters, bacterial origins of replication (ORI sequences), termination sequences, selection genes, for example antibiotic-resistance genes, and sequences ("flanking regions") allowing the targeted insertion of the cassette or the vector.

In addition, said expression cassettes and vectors can be integrated into the genome by techniques well-known to persons skilled in the art.

ORI sequences of interest can be chosen from pIP404, pAMβ1, repH (origin of replication in *C. acetobutylicum*), ColE1 or rep (origin of replication in *E. coli*), or any other origin of replication allowing the vector, typically the plasmid, to be maintained within a *Clostridium* cell.

Termination sequences of interest can be chose from those of the adc and thl genes, of the bcs operon, or of any other terminator, well-known to persons skilled in the art, for stopping transcription within *Clostridium.*

Selection genes of interest can be chosen from ermB, catP, bla, tetA, tetM, and any other gene for resistance to ampicillin, to erythromycin, to chloramphenicol, to thiamphenicol, to tetracycline or to any other antibiotic which can be used to select bacteria of the genus *Clostridium* well-known to persons skilled in the art.

A particular vector comprises one or more expression cassettes, each cassette encoding a gRNA.

In a particular embodiment, the invention relates to a genetic tool comprising as "first" nucleic acid as identified in the claims a plasmid vector whose sequence is selected from one of sequences SEQ ID NO: 5, SEQ ID NO: 6 and SEQ ID NO: 7.

In a particular embodiment, the invention relates to a genetic tool comprising as "second" or "nth" nucleic acid a plasmid vector whose sequence is selected from one of sequences SEQ ID NO: 8, SEQ ID NO: 9, SEQ ID NO: 10 and SEQ ID NO: 11.

The sequence of interest is introduced into the bacterial genome via a homologous recombination mechanism guided by a selected repair template (according to the CRISPR technology). The sequence of interest replaces the targeted portion within the bacterial genome. The recombination process thus allows the total or partial modification or deletion of the targeted portion within the genome of the bacterium or allows the insertion of nucleic acid fragments (in a particular embodiment large fragments) into the genome of the bacterium. The selected repair template can indeed comprise all or part of the targeted sequence of the bacterial genome or a more or less modified version thereof according to the nature of the desired transformation. Just like the targeted portion of DNA, the template can thus itself comprise one or more nucleic acid sequences or nucleic acid sequence portions corresponding to natural and/or synthetic, coding and/or non-coding sequences. The template can for example comprise one or more sequences or portion(s) of sequences corresponding to a gene essential to bacterial survival, in particular to the survival of bacteria of the genus *Clostridium*, or to one or more genes or DNA sequences whose inactivation allows the selection of bacteria of the genus *Clostridium* having integrated the one or more nucleic acids of interest. The template can also comprise one or more "foreign" sequences, i.e., sequences naturally absent from the genome of bacteria belonging to the genus *Clostridium* or from the genome of particular species of said genus. The template can also comprise a combination of sequences as described above.

Particular examples of sequences of interest are the sequences used in the experimental section. They are for example the sequences upp_del (SEQ ID NO: 12) and upp_stop (SEQ ID NO: 13).

The genetic tool according to the invention allows the repair template to guide the incorporation within the bacterial genome of bacteria of the genus *Clostridium* of a nucleic acid of interest, typically of a DNA sequence or sequence portion comprising at least 1 base pair (bp), preferably at least 1, 2, 3, 4, 5, 10, 15, 20, 50, 100, 1,000, 10,000, 100,000 or 1,000,000 bp, typically between 1 bp and 20 kb or between 1 bp and 10 kb, preferably between 10 bp and 20 kb or between 10 bp and 10 kb, for example between 1 bp and 2 kb.

In a particular embodiment, the DNA sequence of interest encodes at least one product of interest, preferably a product promoting the production of solvent, typically at least one protein of interest, for example an enzyme; a membrane protein such as a transporter; a transcription factor; or a combination thereof.

In a preferred embodiment, the DNA sequence of interest promotes the production of solvent and is typically selected from a sequence encoding i) an enzyme, preferably an enzyme involved in the conversion of aldehydes to alcohol, for example selected from a sequence encoding an alcohol dehydrogenase (for example a sequence selected from adh, adhE, adhE1, adhE2, bdhA, and bdhB), a sequence encoding a transferase (for example a sequence selected from ctfA, ctB, atoA and atoB), a sequence encoding a decarboxylase (for example adc), a sequence encoding a hydrogenase (for example a sequence selected from etfA, etB and hydA), and a combination thereof, ii) a membrane protein, for example a sequence encoding a phosphotransferase (for example a sequence selected from glcG, bglC, cbe4532, cbe4533, cbe4982, cbe4983, cbe0751), and iii) a transcription factor (for example a sequence selected from sigE, sigF, sigG, sigH, sigK).

The present invention further relates to a process for transforming and/or genetically modifying by homologous recombination a bacterium of the genus *Clostridium*, preferably a solventogenic bacterium of the genus *Clostridium*. Said process comprises a step of introduction into the bacterium of a genetic tool according to the invention as disclosed in the present application. The process can further comprise a step of obtaining the transformed bacterium, i.e., the bacterium having the one or more desired recombinations/optimizations.

A particular process according to the invention for transforming and/or genetically modifying by homologous recombination a solventogenic bacterium of the genus *Clostridium* comprises, in order, the following steps:

a) introduction into the bacterium of a genetic tool according to the invention as disclosed in the present application comprising at least one inducible promoter, and
b) induction of the expression of the inducible promoter for genetically modifying the bacterium.

Introduction into the bacterium of the components (nucleic acids or gRNAs) of the genetic tool according to the invention is carried out by any direct or indirect method known to persons skilled in the art, for example by transformation, conjugation, microinjection, transfection, electroporation, etc., preferably by transformation (Lütke-Eversloh, 2014).

The induction step, when necessary, can be implemented by any method known to persons skilled in the art after introduction into the target bacterium of the genetic tool according to the invention. It is for example carried out by contacting the bacterium with a suitable substance, present in a sufficient amount, or by exposure to UV light. Said substance releases the inhibition of expression linked to the selected inducible promoter. When the selected promoter is an anhydrotetracycline (aTc)-inducible promoter, chosen from Pcm-2tetO1 and Pcm-tetO2/1, the aTc is preferably used at a concentration ranging between about 1 ng/ml and about 5000 ng/ml, preferably between about 100 ng per ml and about 500 ng/ml or between about 200 ng per ml and about 300 ng/ml, for example about 250 ng/ml.

In a particular embodiment, the process comprises one or more additional steps, subsequent to step b) when it is present, of introduction of an nth, for example a third, fourth, fifth, etc., nucleic acid encoding i) a repair template different from that or those already introduced and ii) one or more guide RNAs allowing their integration into a targeted zone of the genome of the bacterium, each additional step being preferably advantageously preceded by a step of removal of the nucleic acid encoding the repair template previously introduced, the bacterial cell then being regarded as "cleared" of said nucleic acid, and preferably of a step of removal of the one or more guide RNAs or sequences encoding the one or more guide RNAs previously introduced.

In a particularly advantageous manner and in contrast with the tools available in the prior art, the genetic tool according to the invention allows the introduction of sequences of interest of small sizes as well as large sizes, in one step, i.e., using a single nucleic acid (typically the "second" nucleic acid as disclosed in the present text) or in several steps, i.e., using several nucleic acids (typically the "second" and the one or more "nth" nucleic acids as disclosed in the present text), preferably in one step.

In particular embodiment of the invention, this "nth" nucleic acid deletes the targeted portion of the bacterial DNA or replaces it by a sequence which is shorter (for example by a sequence deleted of at least one base pair) and/or non-functional. In a particular preferred embodiment of the invention, the "second" or "nth" nucleic acid advantageously introduces into the bacterial genome a nucleic acid of interest comprising at least one base pair, and up to 2, 3, 4, 5, 6, 7, 8, 9, 10, 11, 12 or 13 kb.

The nucleic acids of interest can be inserted into the bacterial chromosome at identical or different regions according to the gRNAs used, and if it proves useful into a portion of the bacterial genome comprising a gene essential to bacterial survival, for example one of the genes gyrA, pfkA, hydA, crt, thl, hbd, or any other gene known to persons skilled in the art as essential to the survival of a bacterium of the genus *Clostridium*, and/or into a gene or a DNA sequence whose inactivation allows the selection of bacteria having integrated the one or more nucleic acids of interest, for example the upp gene.

By virtue of the invention, typically by virtue of the genetic tool and of the process according to the invention, it is now possible to modify effectively (high frequency of homologous recombination), substantially (possible to incorporate within the genome of the bacterium a nucleic acid of interest of large size) and stably (no need to maintain the transformed bacteria in contact with antibiotics) bacteria of the genus *Clostridium* so as to obtain transformed bacteria of interest, for example enhanced variants having a genotypic or phenotypic difference relative to the bacterium from which it is derived, typically industrially-useful bacteria, for example bacteria useful in the production of solvents or biofuels.

Another object of the invention relates to a bacterium of the genus *Clostridium*, typically a solventogenic bacterium of the genus *Clostridium*, transformed using the process and/or the genetic tool according to the invention. Such a bacterium expresses the one or more nucleic acids of interest introduced into its genome by homologous recombination using the repair template. Such a bacterium can comprise all or part of the genetic tool according to the invention, typically Cas9 or a nucleic acid encoding Cas9.

A particular bacterium of the genus *Clostridium* according to the invention, for example a bacterium ATCC824, transformed using the process and the genetic tool according to the invention, no longer contains the pSOL megaplasmid.

In a particular embodiment, the bacterium of the genus *Clostridium* according to the invention, transformed using the process and the genetic tool according to the invention, is able to produce one or more solvents only by virtue of the expression of the one or more nucleic acids of interest introduced voluntarily into its genome.

The invention also relates to a kit for transforming and/or genetically modifying a bacterium of the genus *Clostridium*, comprising all or part of the components of the genetic tool as disclosed in the present text, typically i) a first nucleic acid encoding Cas9, wherein the Cas9 coding sequence is placed under the control of a promoter, and ii) at least a second nucleic acid encoding a repair template allowing, by a homologous recombination mechanism, the replacement of a portion of the Cas9-targeted bacterial DNA by a sequence of interest, and optionally one or more inducers adapted to the selected inducible promoter(s) optionally used within the tool.

A particular kit according to the invention allows the expression of a Cas9 protein comprising a tag.

The kits according to the invention can further comprise one or more consumables such as a culture medium, at least one competent bacterium of the genus *Clostridium* (i.e., packaged for use in the transformation), at least one gRNA, a Cas9 protein, one or more selection molecules, or a set of instructions.

The invention typically relates to a kit for the implementation of the transformation process disclosed in the present text or for the production of solvent(s) (at least one solvent) using a bacterium of the genus *Clostridium.*

The invention finally relates to the potential uses of the genetic tool, or of the process, or of the kit according to the invention, for transforming and/or genetically modifying a bacterium of the genus *Clostridium*, typically a solventogenic bacterium of the genus *Clostridium*, for example to generate enhanced variants of a bacterium of the genus *Clostridium.*

Finally, the invention relates to the potential uses of the genetic tool, of the process, of the kit or of a bacterium of the genus *Clostridium* transformed according to the invention, in particular for the production of solvents or biofuels, or of mixtures thereof, typically on an industrial scale. Solvents likely to be produced are typically acetone, butanol, ethanol, isopropanol or a mixture thereof, typically an ethanol/isopropanol, butanol/isopropanol, or ethanol/butanol mixture, preferably an isopropanol/butanol mixture.

In a particular embodiment, the ratio of the ethanol/isopropanol mixture is at least equal to ¼. Said ratio is preferably between ⅓ and 1, and more preferably is equal to 1.

In a particular embodiment, the ratio of the ethanol/butanol mixture is at least equal to ¼. Said ratio is preferably between ⅓ and 1, and more preferably is equal to 1.

In a particular embodiment, the ratio of the isopropanol/butanol mixture is at least equal to ¼. Said ratio is preferably between ⅓ and 1, and more preferably is equal to 1.

The use of transformed bacteria according to the invention typically allows the yearly production on an industrial scale of at least 100 tons of acetone, of at least 100 tons of ethanol, of at least 1000 tons of isopropanol, of at least 1800 tons of butanol, or of at least 40,000 tons of a mixture thereof.

The purpose of the examples and figures hereinafter are to more fully illustrate the invention without limiting the scope thereof.

FIGURES

FIG. 1: Metabolism of solventogenic strains of *Clostridium*. The ABE strains produce acetone, ethanol and butanol whereas the IBE strains possess the adh gene converting acetone to isopropanol. Modified from Lee et al., 2012.

FIG. 2: CRISPR mode of action. Mali et al.

Figure 3:
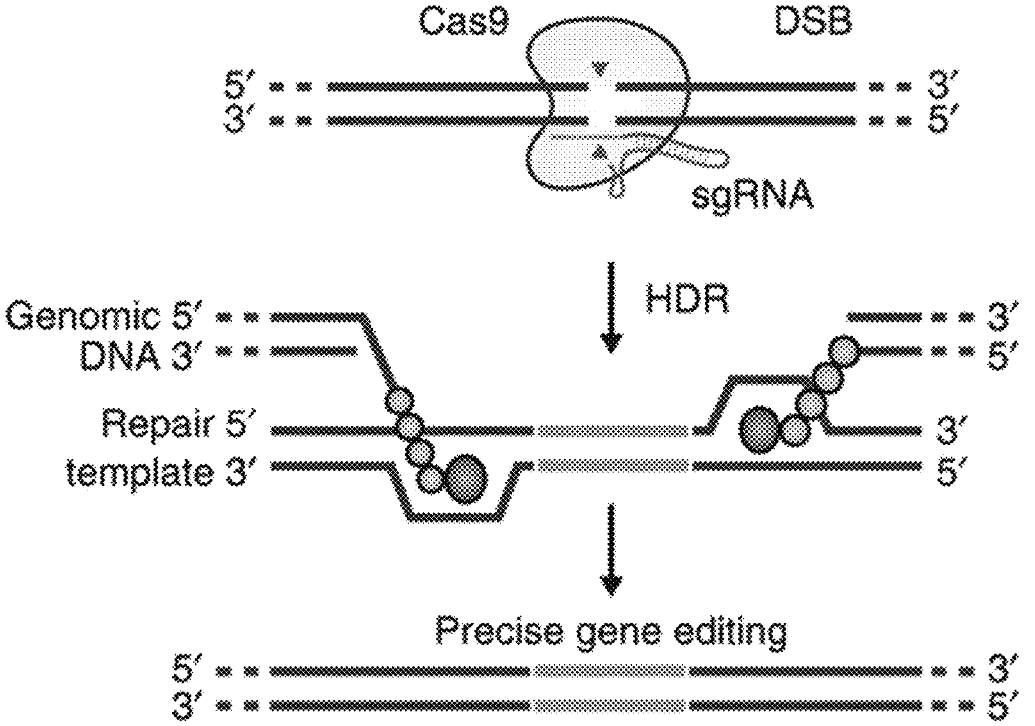

FIG. 3: Use of CRISPR-Cas9 for genome editing. The double-strand break is created by the Cas9 nuclease, directed by the gRNA. Repair of this break by homologous recombination allows the introduction into the genome of the modifications contained in the repair template. Figure modified from Ann Ran et al., 2013.

Figure 4:
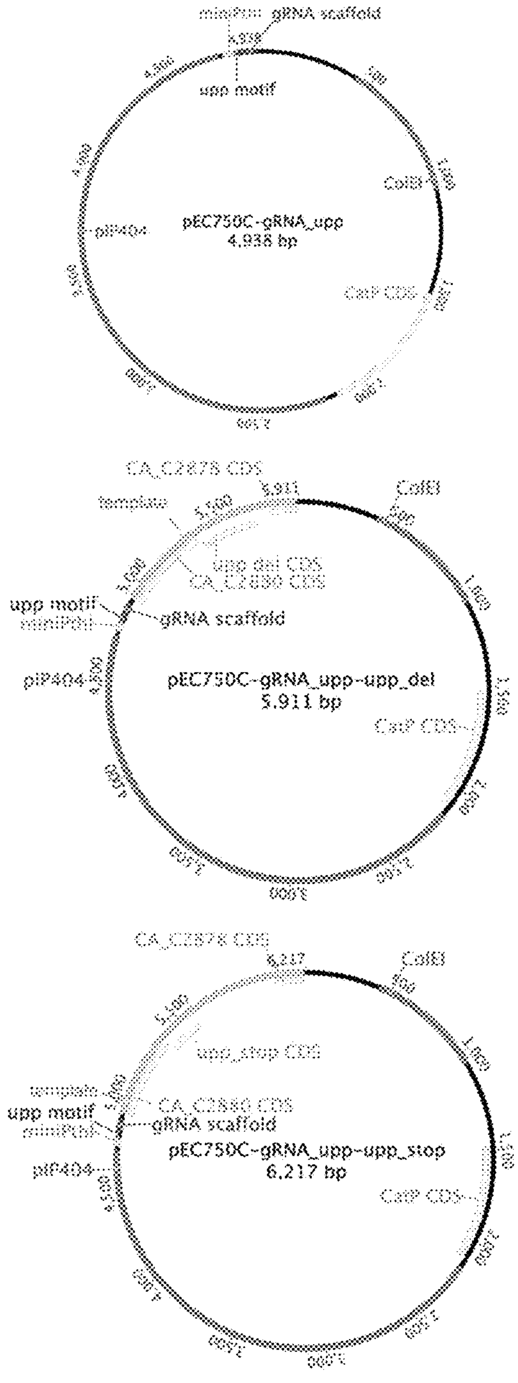

FIG. 4: upp targeting plasmids. pIP404, origin of replication in *C. acetobutylicum*. ColE1, origin of replication in *E. coli*. catP, chloramphenicol acetyltransferase gene (chloramphenicol/thiamphenicol resistance gene). CDS, coding sequence.

Figure 5:
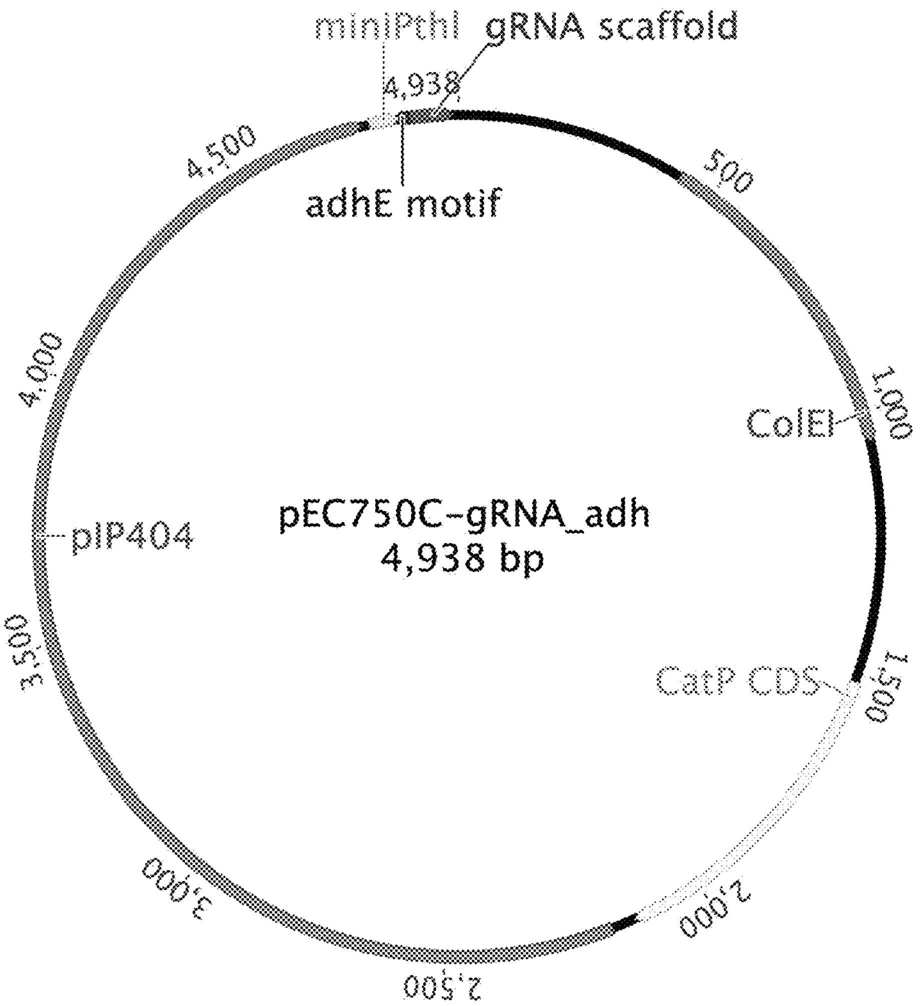

FIG. 5: pSOL targeting plasmid. pIP404, origin of replication in *C. acetobutylicum*. ColE1, origin of replication in *E. coli*. catP, chloramphenicol acetyltransferase gene (chloramphenicol/thiamphenicol resistance gene). CDS, coding sequence.

Figure 6:
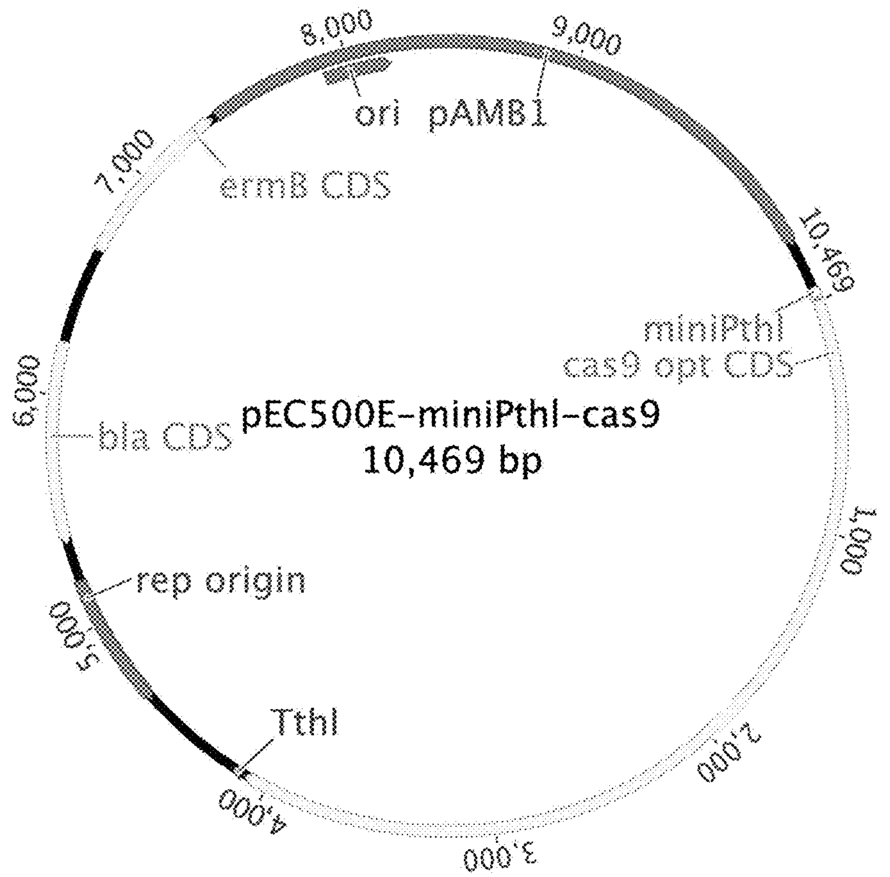

FIG. 6: pEC500E-miniPthl-Cas9 vector map. pAMβ1, origin of replication in *C. acetobutylicum*. rep, origin of replication in *E. coli*. bla, β-lactamase gene (ampicillin resistance). ermB, methylase (erythromycin resistance). CDS, coding sequence.

Figure 7:
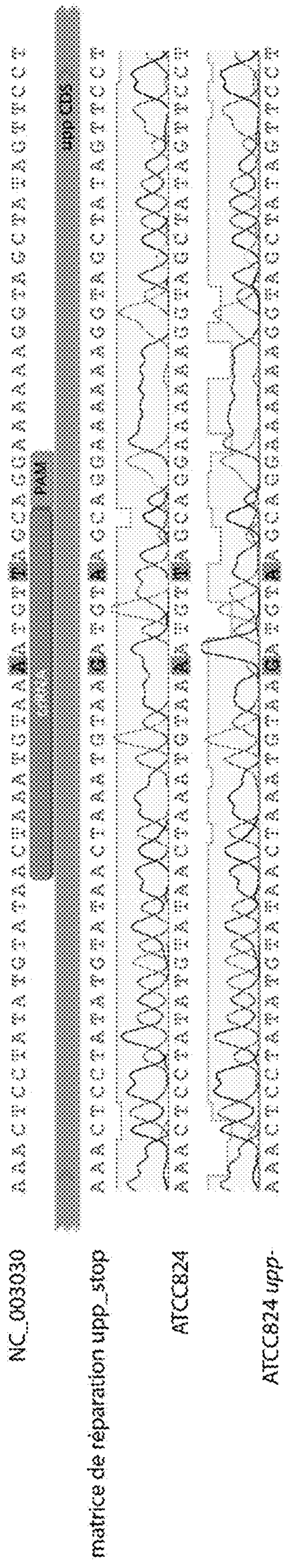

FIG. 7: sequencing of the zone targeted by cas9 in the wild-type strain and in the transformant obtained. NC_003030, sequence of *Clostridium acetobutylicum* ATCC824 (GenBank); crRNA, site recognized by the gRNA; PAM, protospacer adjacent motif, playing a role in Cas9 binding. CDS, coding sequence. SEQ ID NO: 22 corresponds to the NC_003030 fragment appearing in FIG. 7 and SEQ ID NO: 23 corresponds to the fragments appearing in FIG. 7 of the sequences identified as "upp_stop repair template", "ATCC824" and "ATCC824 upp-", respectively.

Figure 8:
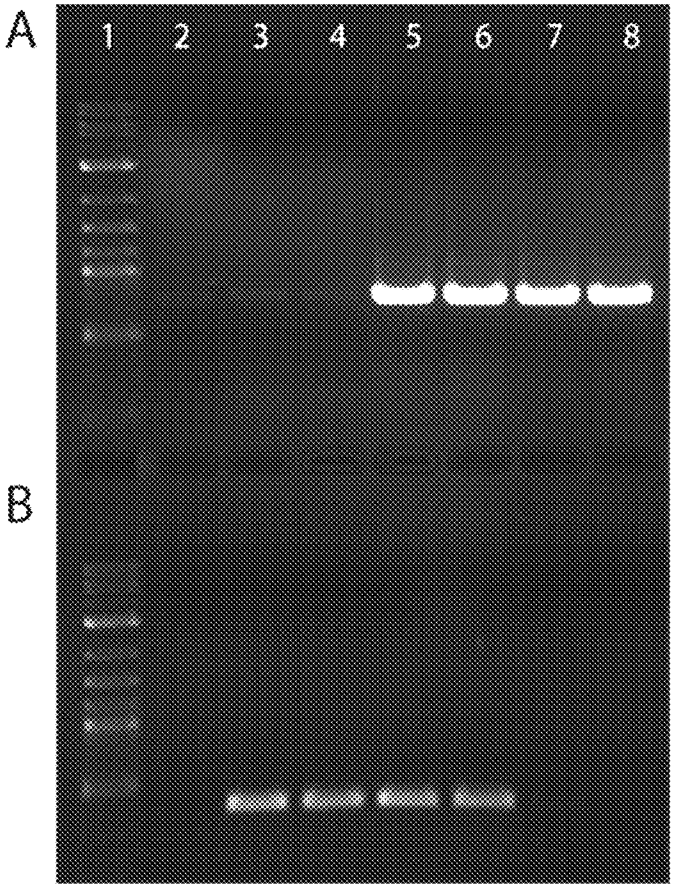

FIG. 8: Amplification results.

A: catP_fwd×catP_rev (expected size: 709 bp)

B: RH_ctfB_R×V-CTFA-CAC2707_R (expected size: 351 bp)

1: 2-Log marker (NEB). 2: $H_2O$, negative control. 3: Non-transformed ATCC824. 4: ATCC824 transformed with pEC500E-miniPthl-cas9. 5 & 6: ATCC824 transformed with pEC500E-miniPthl-cas9 and pEC750C (2 independent transformants). 7 & 8: ATCC824 transformed with pEC500E-miniPthl-cas9 and pEC750C-gRNA_adhE (2 independent transformants).

Figure 9:
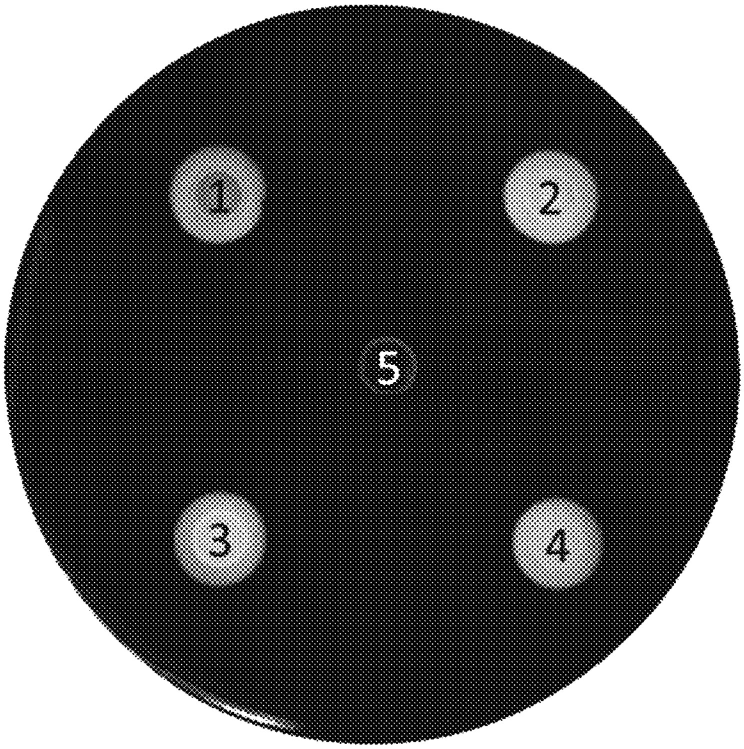

FIG. 9: Detection of a-amylase activity of strains derived from ATCC824. 1: ATCC824; 2: ATCC824 transformed with pEC500E and pEC750C; 3: ATCC824 transformed with pEC500E-miniPthl-cas9 and pEC750C; 4: ATCC824 transformed with pEC500E and pEC750C-gRNA_adhE; 5: ATCC824 transformed with pEC500E-miniPthl-cas9 and pEC750C-gRNA_adhE.

Figure 10:
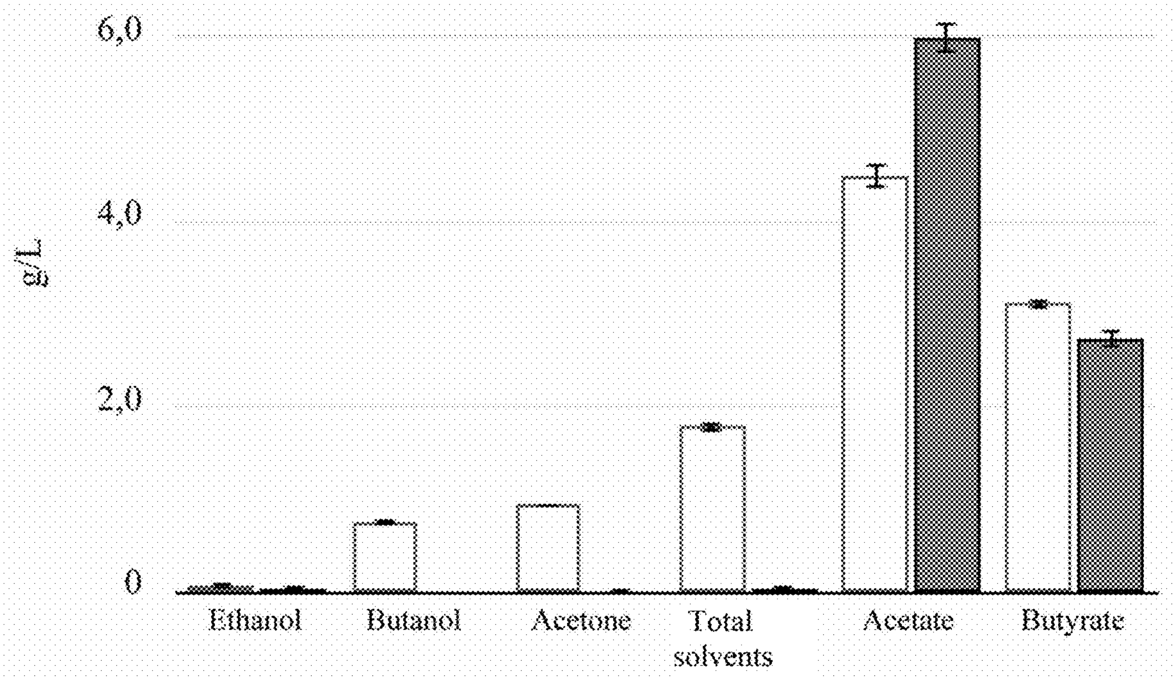

FIG. 10: Fermentation results of the wild-type strain and of a transformant (two technical replicates).

Figure 11:
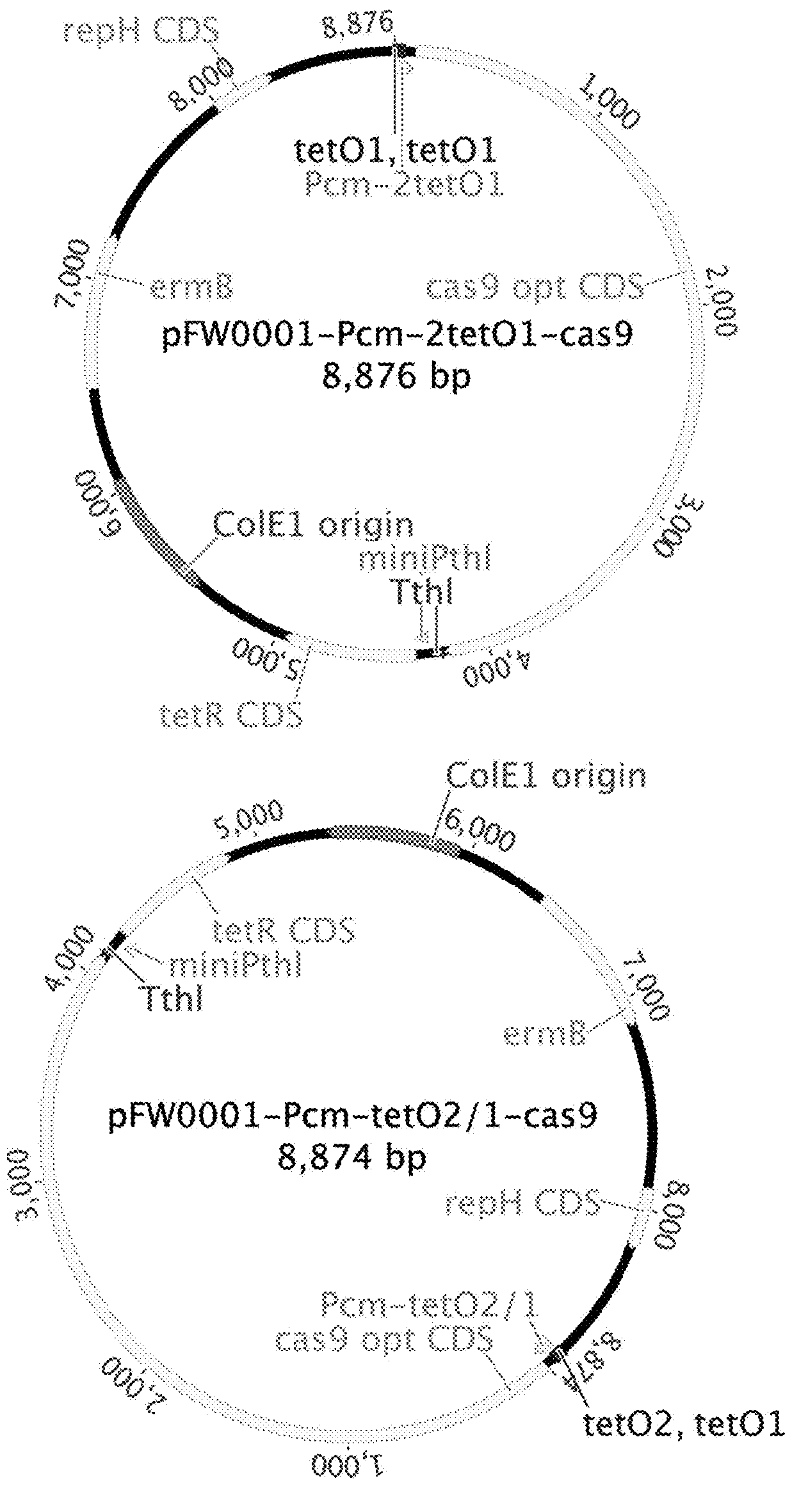

FIG. 11: A/B. Inducible expression plasmids for cas9. repH, origin of replication in *C. acetobutylicum*. ColE1, origin of replication in *E. coli*. ermB, methylase (erythromycin resistance). tetR, gene encoding the transcriptional repressor TetR. CDS, coding sequence.

Figure 12:
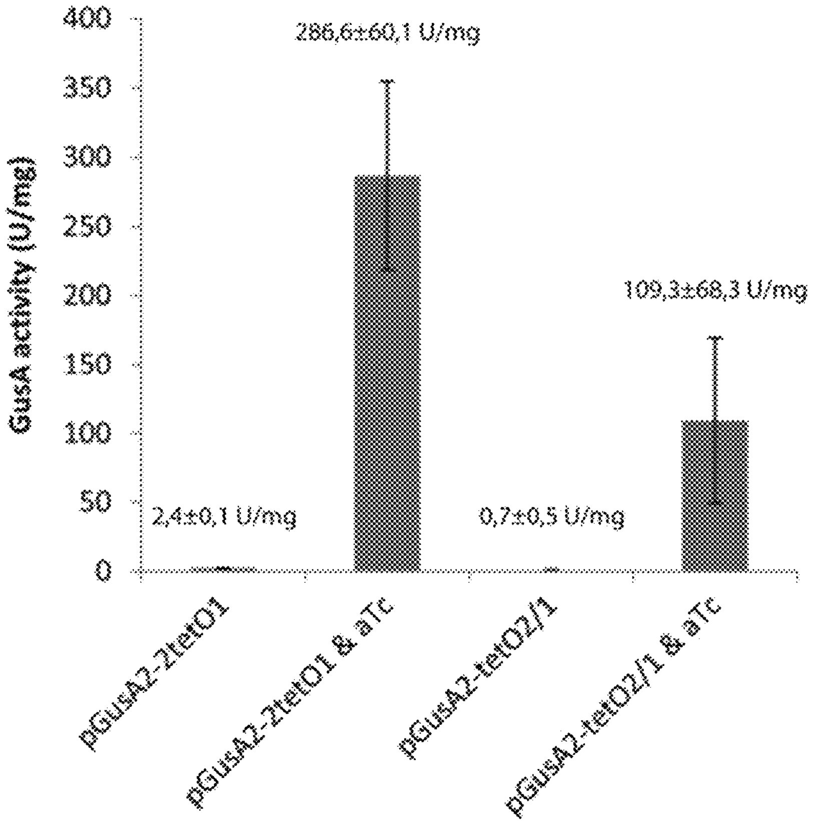

FIG. 12: Effect of induction on expression starting from promoters Pcm-2tetO1 and Pcm-tetO2/1. The promoters were placed downstream of the gusA gene, and GusA activity was measured in *C. acetobutylicum* ATCC824 cells, in the absence or in the presence of 100 ng/mL of aTc. Modified from Dong et al., 2012.

Figure 13:
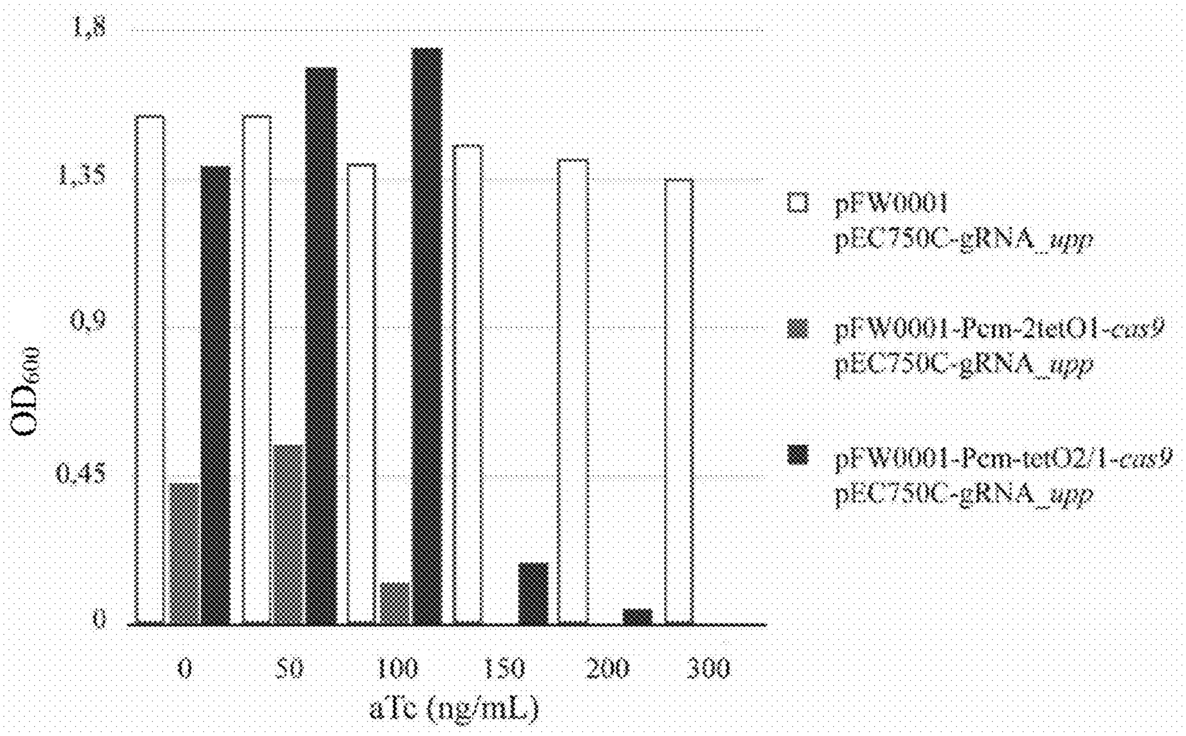

FIG. 13: Effect of aTc concentration on the viability of transformants containing pEC750C-gRNA_upp.

Figure 14:
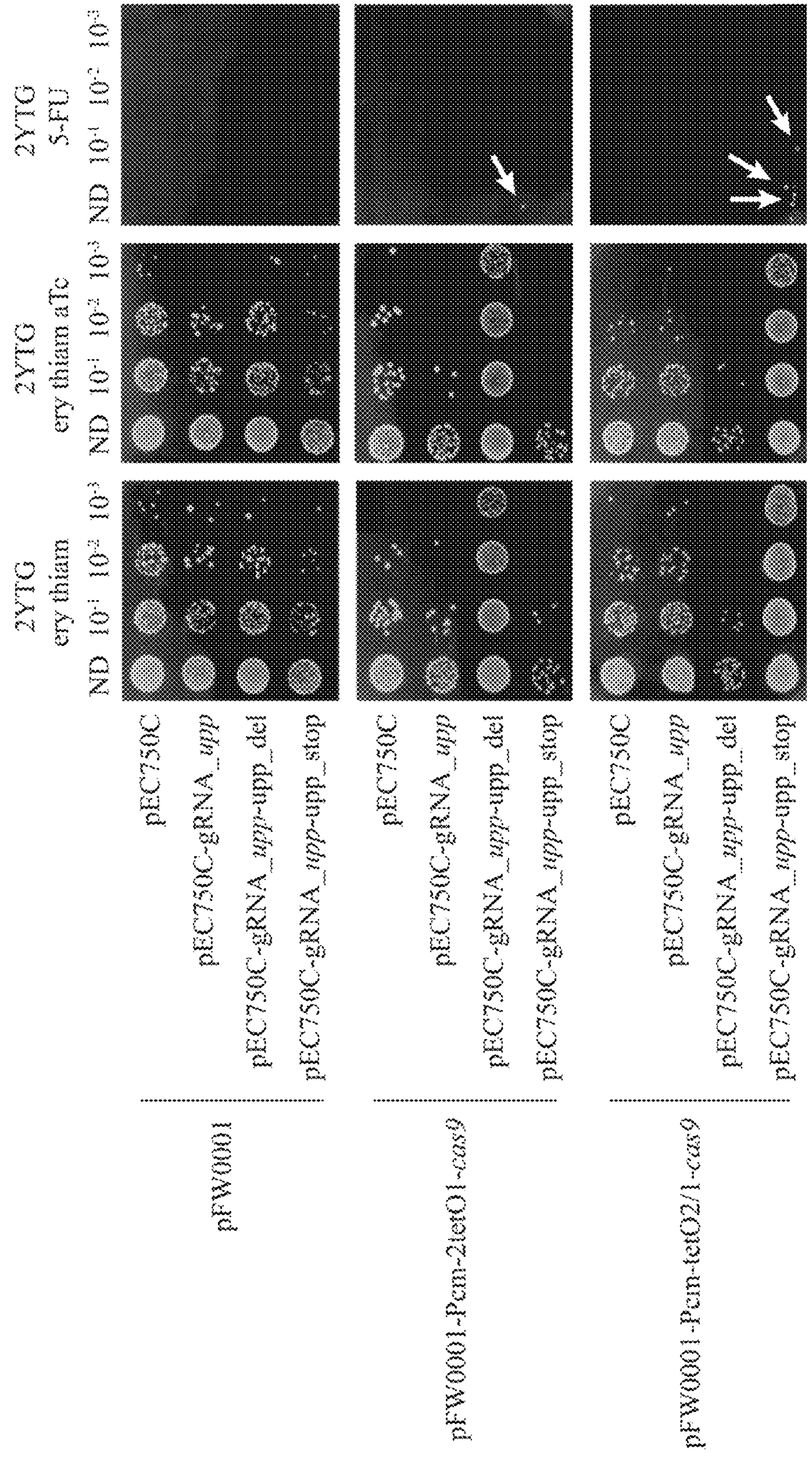

FIG. 14: Generation of 5-FU-resistant mutants. Serial dilutions of liquid cultures are deposited on various media. Only the transformants in which homologous recombination events allowed the insertion of the repair template are able to grow on 2YTG+5-FU. The white arrows indicate the colonies selected for the following experiments. ND, not diluted.

Figure 15:
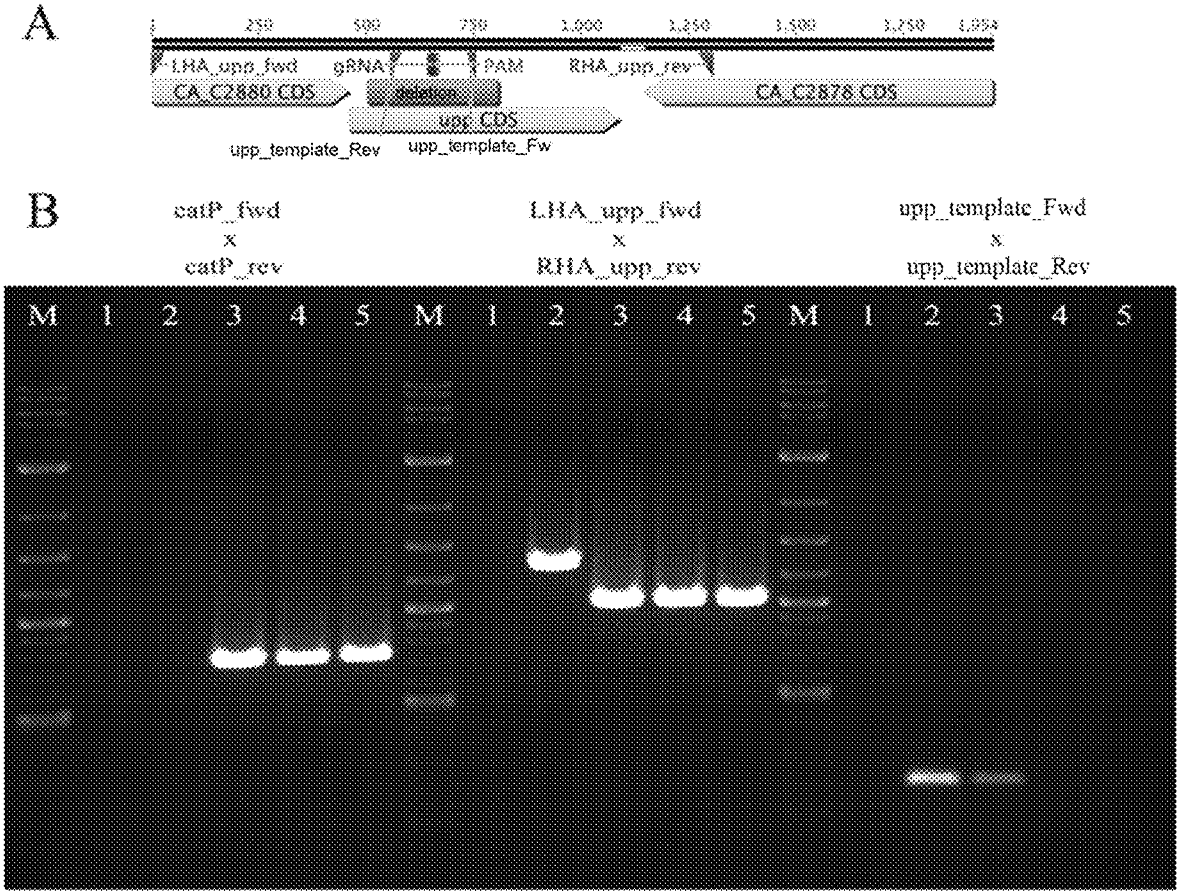

FIG. 15: PCR analysis of the upp_del transformants.

A. Genetic organization around the upp gene. The coding sequences are indicated by arrows. The grey rectangle indicates the region absent from the upp_del template. The primers used are represented by triangles. CDS, coding sequence. PAM, protospacer adjacent motif, playing a role in Cas9 binding.

B. Amplification results. M: 2-Log marker (NEB). 1: $H_20$, negative control. 2: Non-transformed ATCC824.

3: ATCC824 transformed with pFW0001-Pcm-2tetO1-cas9 and pEC750CgRNA_upp-upp_del before exposure to aTc. 4 & 5: ATCC824 transformed with pFW0001-Pcm-2tetO1-cas9 and pEC750CgRNA_upp-upp_del before exposure to aTc, isolated on 2YTG+5-FU (2 independent transformants).

Figure 16:
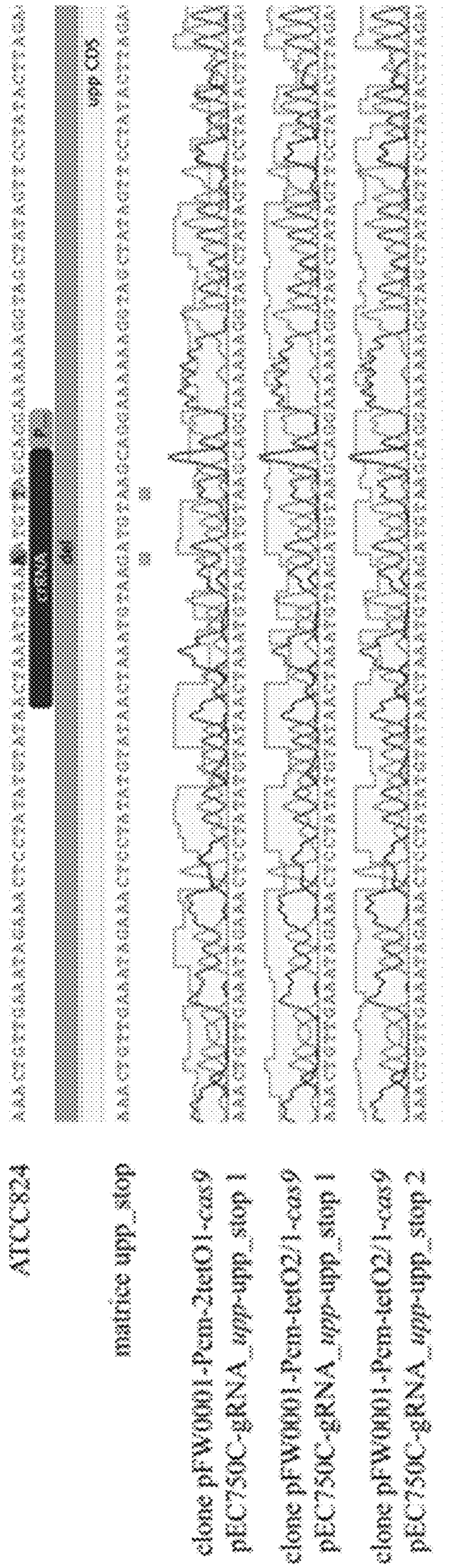

FIG. 16: sequencing of the cas9-targeted zone in colonies isolated on 2YTG+5-FU. NC_003030, sequence of *Clostridium acetobutylicum* ATCC824 (GenBank); crRNA, site recognized by the gRNA; PAM, protospacer adjacent motif, playing a role in Cas9 binding. CDS, coding sequence. SEQ ID NO: 24 corresponds to the fragment of the genomic sequence of strain ATCC824 appearing in FIG. 16 and SEQ ID NO: 25 corresponds to the fragments appearing in FIG. 16 of the sequences identified as "upp_stop template", "clone pFW0001-Pcm-2tetO1-cas9-pEC750C-gRNA_upp-upp_stop1" and "clone pFW0001-Pcm-tetO2/1-cas9-pEC750C-gRNA_upp-upp_stop 1" and "clone pFW000-Pcm-tetO2/1-cas9-pEC750C-gRNA_upp-upp_stop2", respectively.

Figure 17:
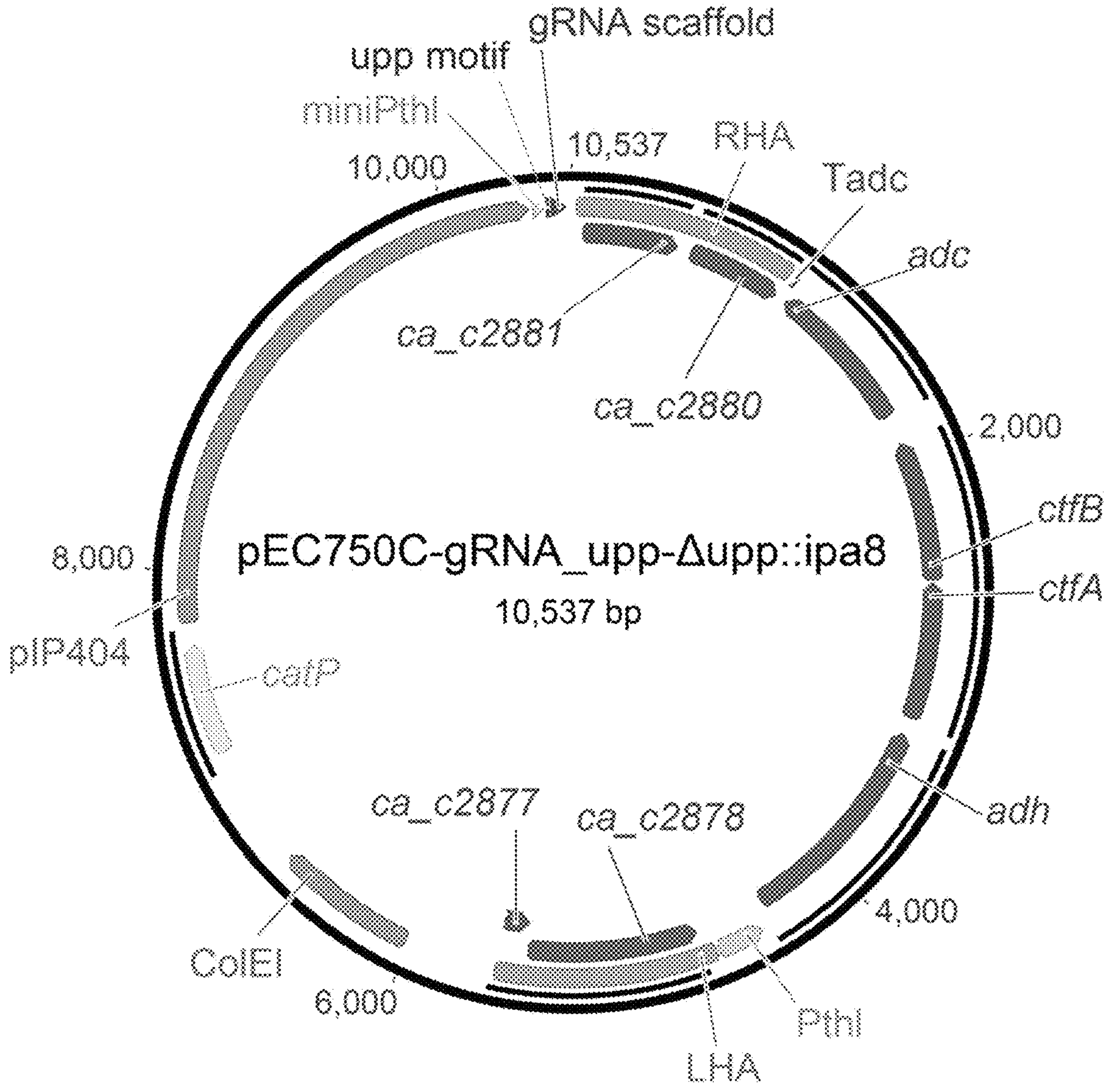

FIG. 17: The pEC750C-gRNA_upp-Δupp::ipa8 plasmid. pIP404, origin of replication in *C. acetobutylicum*. ColE1, origin of replication in *E. coli*. acetyltransferase (chloramphenicol/thiamphenicol resistance gene). CDS, coding sequence. RHA/LHA: flanking sequences of the upp gene (ca_c2879).

Figure 18:
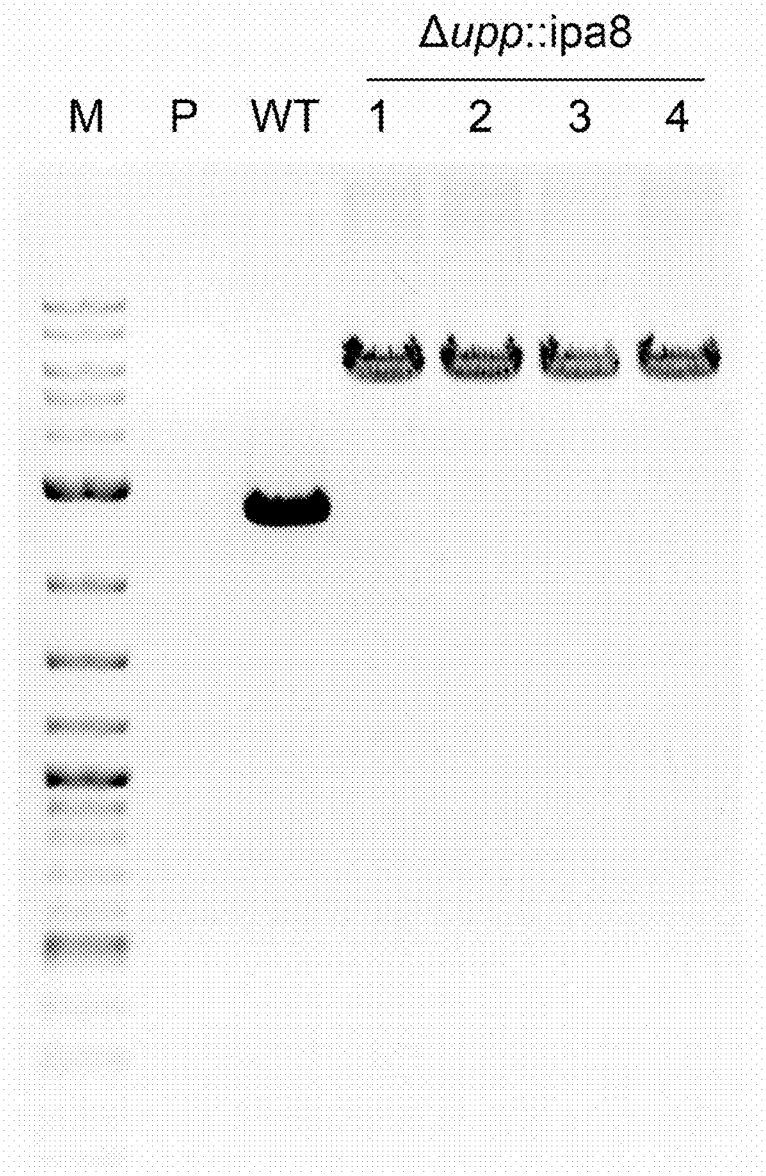

FIG. 18: Amplification results with primers CA_C2877 and CA_C2882. M, 2-log size marker (NEB). P, pEC750C-gRNA_upp-Δupp::ipa8; WT, ATCC 824.

Figure 19:
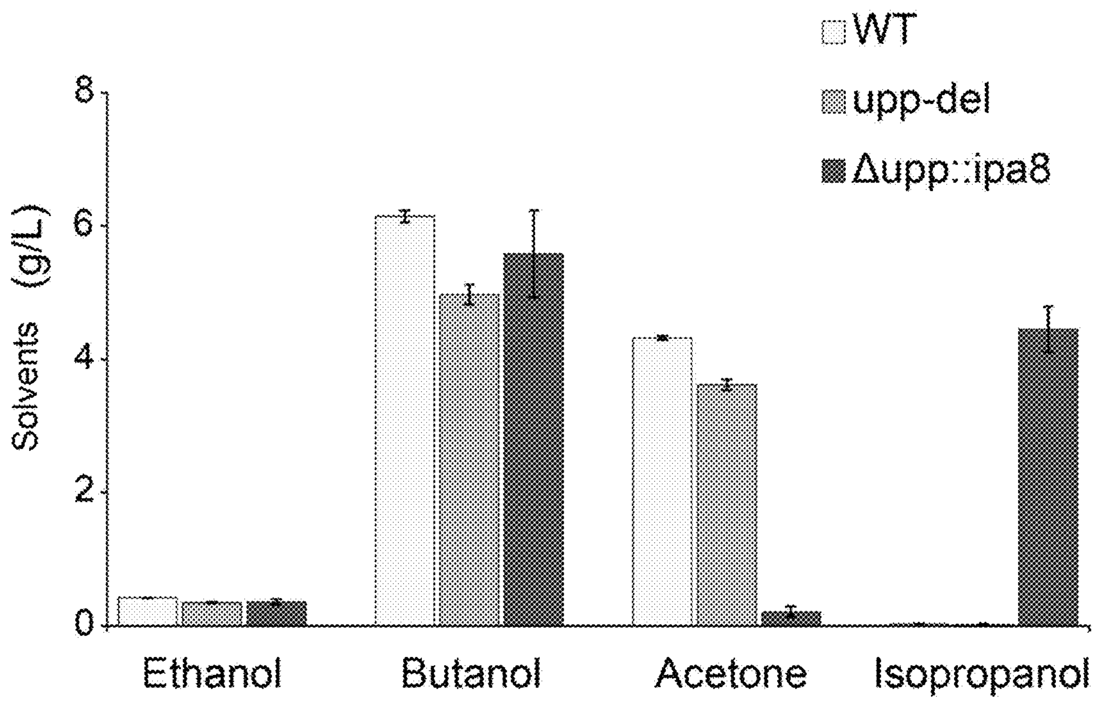

FIG. 19: Production of solvents by ATCC 824 and by mutants upp_del and Δupp::ipa8. The error bars represent the standard deviation of experiments carried out in duplicate. The data obtained for upp_del and Δupp::ipa8 are the averages obtained for two biologically independent mutants in each case.

Figure 20:
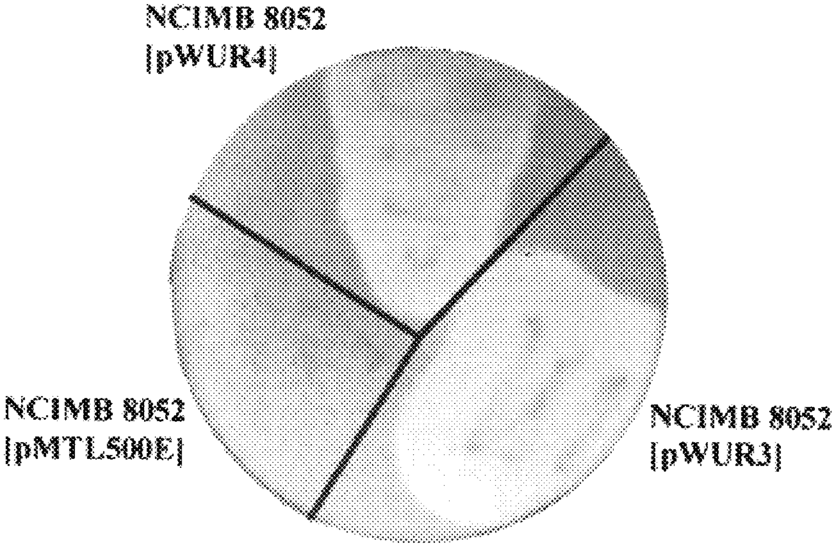

FIG. 20: Measurement of endoglucanase activity on agar of various strains expressing endoglucanases CelA (pWUR3) CelD (pWUR 4) and of the control strain expressing the empty plasmid. These various strains are incubated for 48 h on petri dishes containing 0.2% CMC. A hydrolysis halo visualized by Congo red staining characterizes the endoglucanase activity of each strain. No halo is detectable on the control strain whereas it is clearly visible in the strains expressing endoglucanase CelA or CelD.

Figure 21:
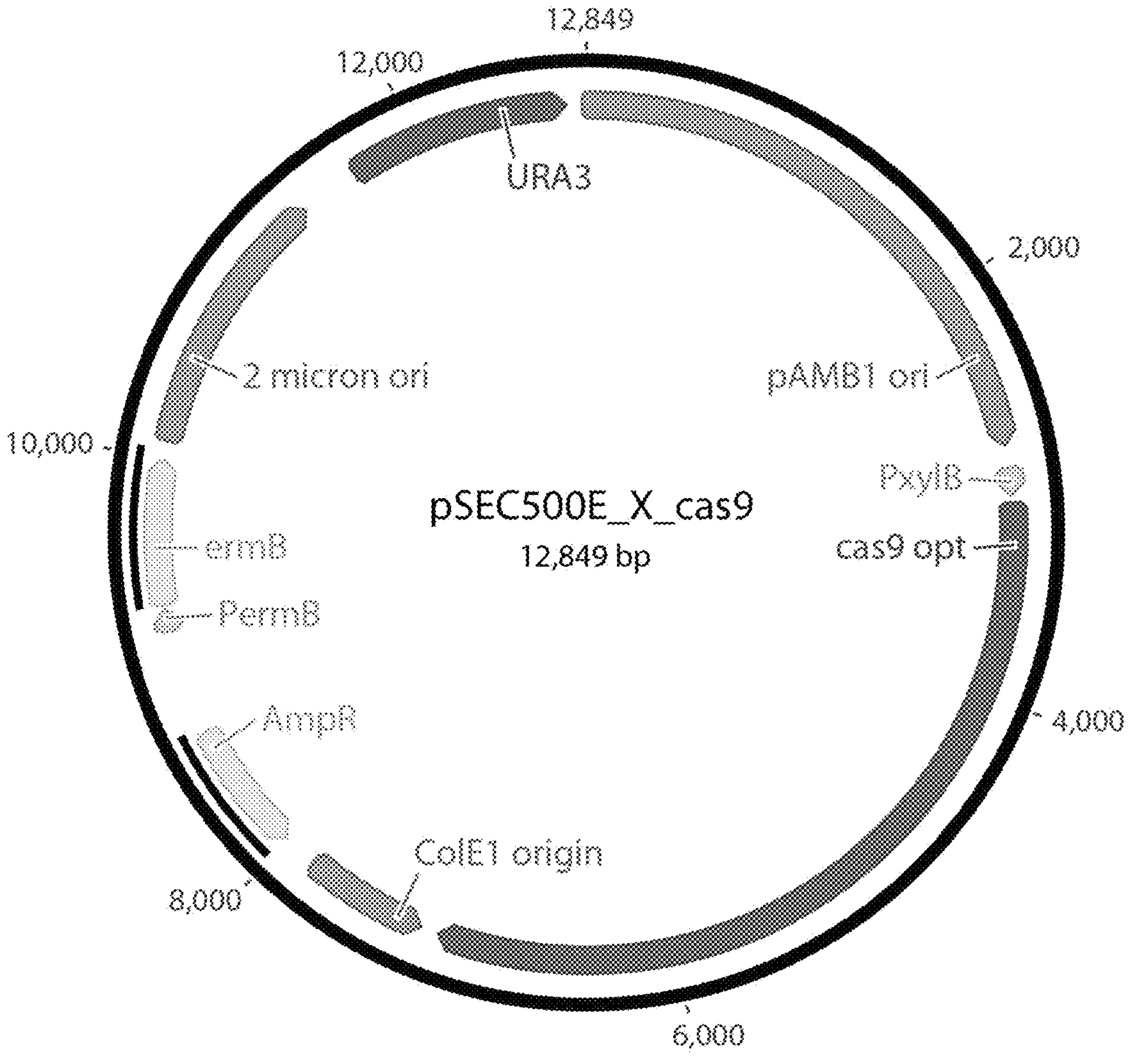

FIG. 21: The pSEC500E_X_Cas9 plasmid. pAMB1, origin of replication in *C. beijerinckii*; PxylB, xylB promoter; ColE1 origin, origin of replication in *E. coli*; AmpR, ampicillin resistance gene; PermB, ermB gene promoter; ermB, erythromycin resistance gene; 2 micron ori, origin of replication in yeast; URA3, auxotrophy marker.

Figure 22:
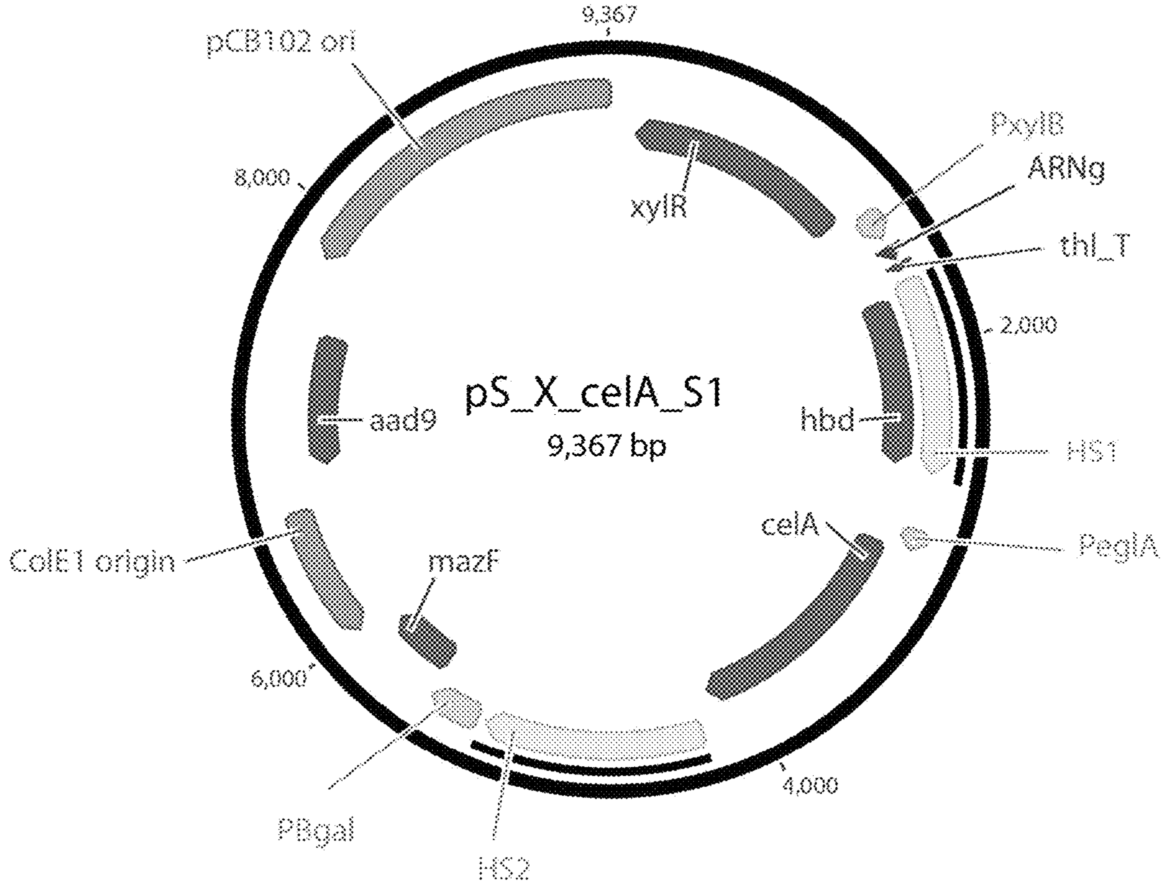

FIG. 22: The pS_celAS1 plasmid. HS1 and HS2, homology sequences; aad9, spectinomycin resistance gene; pCB102, origin of replication in *C. beijerinckii*; ColE1 origin, origin of replication in *E. coli*. PeglA, eglA gene promoter.

Figure 23:
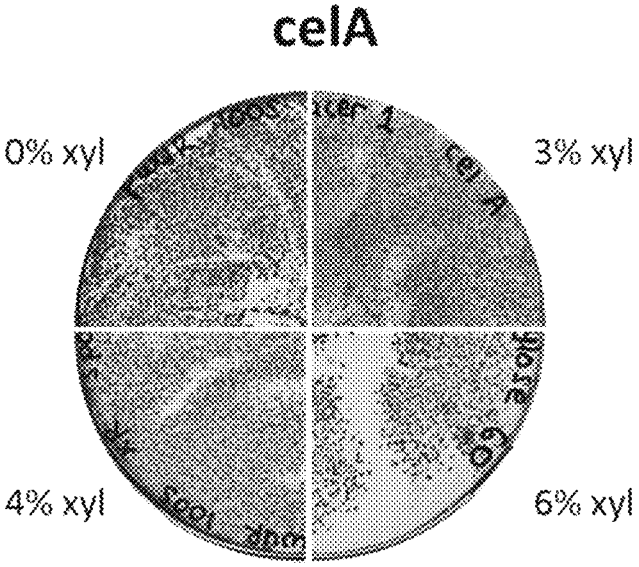

FIG. 23: Selection of recombinant strains *C. beijerinckii* NCIMB8052 (pEC500E_Xcas9, pS_celAS1) on CGM agar containing increasing concentrations of xylose.

Figure 24:
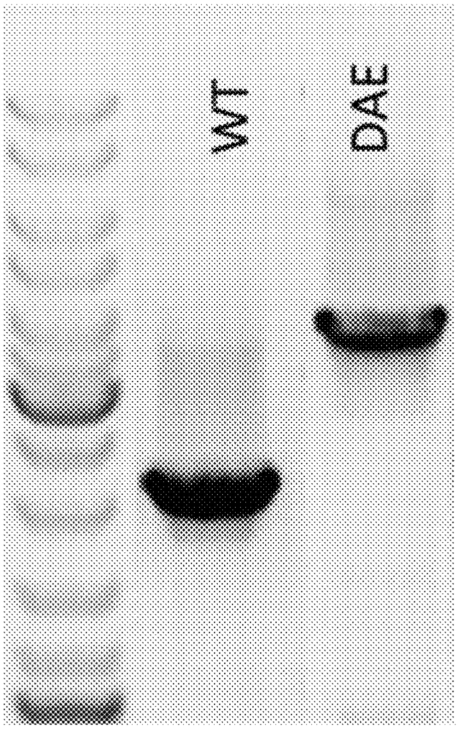

FIG. 24: Verification by PCR of strain NCIMB8052 and of strain NCIMB8052 having integrated the celA gene. M, GeneRuler 1 kb DNA Ladder (ThermoFisher).

EXAMPLES

The inventors tested the genetic tool disclosed and claimed in the present text on two targets: the upp and adhE genes.

Inactivation of the upp Gene

The first target chosen makes it possible to validate the genetic modification technique designed, by a simple screening. The upp gene encodes a uracil phosphoribosyltransferase. This enzyme forms uracil monophosphate (UMP) from uracil, but also forms 5-fluorouracil monophosphate (5-FUMP) from 5-fluorouracil (5-FU). 5-FUMP is a toxic compound for the cell which blocks RNA synthesis. Consequently, a bacterium containing the upp gene in its genome will not be able to grow on medium containing 5-FU, in contrast with a strain not expressing this gene.

Targeting this gene makes it possible to determine, simply and quickly, by simple phenotypic observation, if the modification strategy is effective. Three plasmids for targeting upp were constructed (see FIG. 4+SEQ ID NO: 9, 10 and 11). All three contain the same gRNA targeting the gene, and two of them also contain different repair templates for showing the abilities of the tool to create deletions or point mutations:

- The upp_del template (SEQ ID NO: 12) contains two 500-nucleotide (nt) fragments located 150-nt from each side of the break site determined by the gRNA. The use of this template to repair the break causes a 300-nt deletion within the coding sequence of the upp gene so that the latter will then encode an inactive protein.
- The upp_stop template (SEQ ID NO: 13) contains two 650-nt fragments located on each side of the break site, which are modified at the gRNA recognition site by the presence of nonsense mutations (inducing the replacement of a codon encoding an amino acid by a stop codon) in such a way that Cas9 can no longer target the gene which will encode an incomplete and inactive protein.

Loss of the pSOL Plasmid

The second target chosen is of interest in the fermentation process: the set of genes involved in solventogenesis, in particular adhE, is located on the pSOL megaplasmid, and it has been shown that its loss abolishes the production of acetone and butanol. After having removed these fermentation pathways using the pSOL targeting plasmid (see FIG. 5), it is possible to reintroduce the genes of interest directly into the genome. In order to obtain a strain no longer containing pSOL, a plasmid for targeting adhE was constructed. The inventors showed that pSOL does not contain essential functions for the cell so that the cell will be able to survive without its presence.

Constitutive Expression of cas9 in *C. acetobutylicum* ATCC824

The chosen strategy requires the concomitant use of two plasmids:

- the vector for constitutive expression of the nuclease, derived from the pEC500E plasmid: pEC500E-miniPthl-Cas9 (see FIG. 6+SEQ ID NO: 5);
- one of the targeting vectors, which determine the nuclease break site and optionally allow the repair of the break, derived from pEC750C:
- pEC750C-gRNA_upp (SEQ ID NO: 9), containing the gRNA targeting upp;
- pEC750C-gRNA_upp-upp_del (SEQ ID NO: 10), containing the gRNA targeting upp and the upp_del template;

pEC750C-gRNA_upp-upp_stop (SEQ ID NO: 11), containing the gRNA targeting upp and the upp_stop template;

pEC750C-gRNA_adhE (SEQ ID NO: 8), containing the gRNA targeting adhE.

The pEC500E-miniPthl-Cas9 expression vector was introduced into strain ATCC824, as well as a control plasmid corresponding an empty vector (pEC500E). The two strains obtained were then transformed with the targeting vectors, derived from vector pEC750C, used as control. The results of this second transformation step are indicated below in Table 1.

TABLE 1 transformation results.

| | pEC750C | pEC750C-gRNA_upp | pEC750C-gRNA_upp-upp_del | pEC750C-gRNA_upp-upp_stop | pEC750C-gRNA_adhE |
|---|---|---|---|---|---|
| pEC500E | ++ | ++ | ++ | ++ | ++ |
| pEC500E-miniPthl-cas9 | ++ | − | − | + | ++ |

++, numerous transformants obtained (between $10^2$ and $10^3$ colonies obtained/transformation);
−, no transformants obtained.

The transformation results obtained indicate that Cas9 is functional. Indeed, when the nuclease is expressed and the upp gene is targeted by the gRNA, no transformant is obtained, due to the break caused in the genomic DNA and to the inability of the bacterium to carry out the repair of the genome (transformation with pEC500E-miniPthl-cas9 and pEC750C-gRNA_upp) in the absence of repair template.

Targeting of upp

The results obtained when the targeting vectors are introduced into the strain containing pEC500E show that the genome of strain ATCC824 does not contain a cas9 homologue, since transformants are obtained with each targeting vector.

A transformant containing pEC500E-miniPthl-cas9 and pEC750C-gRNA_upp-upp_stop was then re-plated several times on a nonselective medium so that it loses the plasmids it contained. Once the colonies were cleared of their plasmids and sensitive to antibiotics, the upp gene (SEQ ID NO: 3) was sequenced (see FIG. 7).

The desired modifications are indeed present. The CRISPR-Cas9 genetic tool comprising the introduction of two plasmids and the expression of the cas9 gene by a strong and constitutive promoter is thus indeed functional.

Targeting of adhE

Transformants are obtained during transformations of the wild-type strain with the pEC500E-miniPthl-cas9 and pEC750C_gRNA_adhE plasmids. Since cas9 is active, this result indicates that a break in the pSOL megaplasmid does not affect the viability of ATCC824.

In order to confirm the possible loss of pSOL, various tests were performed:

PCR detection of a gene present on pSOL: ctfB

PCR using catP_fwd×catP_rev allows detection of the thiamphenicol resistance gene, present on the pEC750C plasmids. Its detection confirms that the targeting vectors are present.

PCR using RH_ctfB_R×V-CTFA-CAC2707_R allows detection of a portion of the ctfB gene, present on the pSOL megaplasmid, and makes it possible to know if the latter is present in the cell. Amplification seems to show that the pSOL megaplasmid is no longer present in the clones transformed with pEC500E-miniPthl-cas9 and pEC750C-gRNA_adhE (see FIG. 8).

Detection of an enzymatic activity encoded by a gene present on pSOL

Among the genes contained on the pSOL megaplasmid, amyP encodes an extracellular enzyme with α-amylase activity. This activity can be detected on solid medium containing starch and glucose (Sabathe et al., 2002). Dilutions of liquid cultures were deposited on an agar plate containing 0.2% glucose and 2% starch and incubated 72 h at 37° C. The α-amylase activity is then visualized by iodine staining. The clear halos around the colonies of bacteria indicate the presence of α-amylase activity. The absence of activity around ATCC824 containing pEC500E-miniPthl-cas9 and pEC750C-gRNA_adhE indicates that the amyP gene is not expressed in this strain, confirming that the megaplasmid is no longer present (see FIG. 9).

Fermentation results

The ATCC824 wild-type strain and a transformant were grown for 24 h in Gapes medium in order to establish the fermentation results of the two strains. The fermentation results obtained show a reduction in ethanol production and an abolition of butanol and acetate production due to the absence of the adhE, adhE1 and adc genes (present on the pSOL megaplasmid) in the transformant (see FIG. 10).

Cas9 is thus capable of acting on the chromosome or on the natural plasmid of strain ATCC824, which makes it possible to broaden its action to the chromosome and to any extra-chromosomal genetic material present in the strain (plasmid, bacteriophage, etc.).

Inducible Expression of Cas9 in *C. acetobutylicum* ATCC824

In order to enable the homologous recombination events between the genome and the repair templates, it is necessary to increase the number of cells in which the nuclease is active (up to $10^3$ when strain ATCC824 containing pEC500E-miniPthl-cas9 is transformed with a targeting vector). To that end, a system in which nuclease expression is controlled is necessary. Two vectors in which the cas9 gene is placed under the control of an anhydrotetracycline-inducible promoter were constructed, derived from the vector pFW0001:

pFW0001-Pcm-2tetO1-cas9 (see FIG. 11A+SEQ ID NO: 6);

pFW0001-Pcm-tetO2/1-cas9 (see FIG. 11B+SEQ ID NO: 7);

The promoters controlling cas9 expression contain operator sequences, tetO1 and tetO2, to which the transcriptional repressor TetR is bound. This repression is released by the presence of anhydrotetracycline (aTc). This system allows controlled expression, with little leakage. In the presence of aTc, synthesis is higher starting from promoter Pcm-2tetO1 (see FIG. 12).

Transformation of *C. acetobutylicum* ATCC824:

The expression vectors and the empty vector (pFW0001) were introduced into ATCC824. Subsequently, the following plasmids were introduced into each type of transformant (see Table 2):

- pEC750C-gRNA_upp, containing the gRNA targeting upp;
- pEC750C-gRNA_upp-upp_del, containing the gRNA targeting upp and the upp_del template;
- pEC750C-gRNA_upp-upp_stop, containing the gRNA targeting upp and the upp_stop template;

The transformed colonies were streaked on various solid media, at different dilutions:

- 2YTG+erythromycin to verify cell viability, dilution by a factor of $10^6$;
- 2YTG+erythromycin+thiamphenicol to select the transformants;
- 2YTG+erythromycin+thiamphenicol+aTc (200 ng/mL) to select the transformants in the presence of the inducer.

Liquid media containing erythromycin, thiamphenicol and increasing concentrations of aTc were inoculated from liquid precultures of these transformants (see FIG. 13). The ability of the cells to grow is evaluated by measurement of the optical densities after 72 h of culture.

The transformant not expressing the nuclease is affected little or not at all by the presence of aTc. On the other hand, even at low aTc concentrations, the transformant containing the plasmid expressing cas9 via promoter Pcm-2tetO1 (pFW0001-Pcm-2tetO1-cas9) and the plasmid containing only the gRNA (pEC750C-gRNA_upp) exhibit a significant growth delay. The transformant containing the plasmid expressing cas9 via promoter Pcm-tetO2/1 (pFW0001-Pcm-tetO2/1-cas9) and the plasmid containing only the gRNA (pEC750C-gRNA_upp) is not affected at low aTc concentrations.

However, starting from 150 ng/mL a strong growth delay is observed, and no growth is observed at 300 ng/mL.

TABLE 2 number of colonies obtained on each type of medium for each transformation.

| | pEC750C | | | pEC750C-gRNA_upp | | | pEC750C-gRNA_upp-upp_del | | | pEC750C-gRNA_upp-upp_stop | | |
|---|---|---|---|---|---|---|---|---|---|---|---|---|
| | ery ($10^{-6}$) | ery thiam (ND) | ery thiam aTc (ND) | ery ($10^{-6}$) | ery thiam (ND) | ery thiam aTc (ND) | ery ($10^{-6}$) | ery thiam (ND) | ery thiam aTc (ND) | ery ($10^{-6}$) | ery thiam (ND) | ery thiam aTc (ND) |
| pFW0001 | 78 | 26 | — | 126 | 83 | — | 87 | 12 | — | 61 | 13 | — |
| pFW0001-Pcm-2tetO1-cas9 | 229 | 129 | 3 | 157 | 27 | 0 | 232 | 5 | 0 | 169 | 7 | 0 |
| pFW0001-Pcm-tetO2/1-cas9 | 210 | 400 | 3 | 367 | 130 | 0 | 227 | 21 | 0 | 177 | 18 | 0 |

ery, erythromycin. thiam, thiamphenicol. aTc, anhydrotetracycline.
Between brackets, dilution factors.
ND, not diluted.
—, not tested.

A toxic effect of aTc is observed, since few transformants are obtained when it is present, even when the empty targeting vector (pEC750C, control) is used. As expected, no transformant is obtained when a pEC750C containing the gRNA_upp cassette is introduced into a cell expressing cas9, on medium containing aTc. On the other hand, numerous transformants are obtained for each plasmid combination on medium without aTc, indicating that cas9 is not expressed.

Cas9 Expression in the Presence of aTc:

The various transformants obtained on plates containing erythromycin and thiamphenicol were re-plated on the same type of medium, then used to inoculate liquid precultures containing both antibiotics. These precultures were then used to inoculate other liquid cultures containing varying concentrations of aTc in order to determine if the system is functional.

Induction of Cas9:

Three transformants were used to analyse the ability to induce cas9 expression in the presence of aTc:

ATCC824 containing pFW0001 and pEC750C-gRNA_upp;

ATCC824 containing pFW0001-Pcm-2tetO1-cas9 and pEC750C-gRNA_upp;

ATCC824 containing pFW0001-Pcm-tetO2/1-cas9 and pEC750C-gRNA_upp;

Promoter Pcm-tetO2/1 thus seems to allow a better repression of the expression than Pcm-2tetO1 in the absence of inducer.

Generation of Mutants

Liquid cultures of the transformant containing the targeting plasmids for repairing double-strand breaks were also prepared, in the absence or in the presence (100 ng/mL) of aTc. The transformants used contained one of the 12 plasmid combinations appearing in Table 3.

TABLE 3

Plasmid combinations present in the transformants.

| Expression plasmid | | Targeting plasmid |
|---|---|---|
| pFW0001 | | pEC750C |
| pFW0001-Pcm-2tetO1-cas9 | x | pEC750C-gRNA_upp |
| pFW0001-Pcm-tetO2/1-cas9 | | pEC750C-gRNA_upp-upp_del |
| | | pEC750C-gRNA_upp-upp_stop |

After 72 h of culture, aliquots were deposited on various solid media:

- 2YTG containing thiamphenicol and erythromycin;
- 2YTG containing thiamphenicol, erythromycin, and 100 ng/mL aTc;
- 2YTG containing 5-fluorouracil.

Only the transformants in which homologous recombination events allowed the insertion of the repair template are able to grow on 2YTG+5-FU (see FIG. 14).

Analysis of the upp_Del Transformants:

The clones isolated on 2YTG+5-FU were analysed by PCR (see FIG. 15).

PCR using catP_fwd×catP_rev allows detection of the thiamphenicol resistance gene, present on the pEC750C plasmids. Its detection confirms that the targeting vectors are present.

PCR using LHA_upp_fwd×RHA_upp_rev allows amplification of the upp gene as well as the flanking regions. The primers appearing below were used in the construction of the upp_del repair template (see FIG. 15+SEQ ID NO: 14-21):

TABLE 4

| Name | Sequence (5'-3') |
|---|---|
| catP_fwd | GTGGGCAAGTTGAAAAATTCAC |
| catP_rev | TTAACTATTTATCAATTCCTGCAATTCG |
| RH_ctfB_R | CTTGAGACTTTGCCGTGAGGG |
| V_ctfA_CAC2707_R | TAGTTGGAATGGGCGCTAGT |
| LHA_upp_fwd | ATGAAGATAGCAATAGGTAGTGATCATGC |
| RHA_upp_rev | ACGCTTATATTATCAATATTATTTAGCTTTATAG |
| upp_template_fwd | TGTCCAACCTTAGCAGCAGG |
| upp_template_rev | GTAGAAGAAGTAGCAATGCTAATGGC |

PCR using upp_template_fwd×upp_template_rev allows amplification of an internal fragment of the upp gene, absent from the upp_del repair template.

The results obtained confirm the deletion within the upp gene in the transformants analysed.

Analysis of the upp_Stop Mutants:

The upp gene was sequenced in three clones isolated on 2YTG+5-FU after exposure to aTc (see FIG. 16):

- One containing the plasmid expressing cas9 via promoter Pcm-2tetO1 (pFW0001-Pcm-2tetO1-cas9) and the plasmid containing the gRNA as well as the upp_stop repair template (pEC750CgRNA_upp-upp_stop);
- Two containing the plasmid expressing cas9 via promoter Pcm-tetO2/1 (pFW0001-Pcm-tetO2/1-cas9) and the plasmid containing the gRNA as well as the upp_stop repair template (pEC750CgRNA_upp-upp_stop).

The strategy aimed at developing a genetic modification system by the use of the cas9 gene under the control of an inducible promoter and of the gRNA present in a second plasmid is thus functional.

Compared with the use of the constitutive promoter miniPthl, the induction of the cas9 gene makes it possible to control the action of the enzyme and to facilitate the selection of transformants having undergone the desired modifications.

Replacement of the upp Gene by the Operon Ipa8

The modification made consists of the insertion within the *C. acetobutylicum* ATCC 824 genome of the operon ipa8 containing the adh gene from *C. beijerinckii* DSM6423 (allowing the conversion of acetone to isopropanol) and the adc, ctfA, ctfB genes of strain ATCC 824 (allowing the re-assimilation of the acids produced and the formation of acetone) under the control of the constitutive promoter of the thl gene. This 3614-bp operon is inserted in place of the upp gene.

A repair template made up of the operon flanked by 1-kb sequences located on each side of the upp gene was inserted into the pEC750-gRNA_upp plasmid to obtain the pEC750C-gRNA_upp-Δupp::ipa8 plasmid (see FIG. 17 and SEQ ID NO: 26).

This plasmid was introduced into competent ATCC 824 cells containing the pFW0001-Pcm-tetO2/1-cas9 plasmid. The induction of cas9 expression was carried out on 2YTG medium containing thiamphenicol, erythromycin, and the inducer aTc.

The colonies obtained were analysed by PCR with primer pair CA_C2877 and CA_C2882 which allows the amplification of a 2720-bp product in strain ATCC 824:

```
CA_C2877:
                                    (SEQ ID NO: 27)
5'-CTTTTTAAAAAAGTTAAATAAGGAAGG-3';

CA_C2882:
                                    (SEQ ID NO: 28)
5'-GTTTAACTTAAGTTACAGAAAAGCTAGG-3'.
```

The results of PCR assays carried out on the various controls and on 4 independent colonies obtained after induction confirm the replacement of the upp gene by the operon ipa8 (FIG. 18).

Fermentations were carried out in Gapes medium (Gapes et al., 1996) for 72 h at 34° C. and 150 rpm on the mutants obtained, as well as on the WT strain and Δupp mutants used as controls. The fermentation supernatants were analysed by HPLC using a 0.5 g/L propanol solution as internal standard. Carbohydrate concentrations were quantified on an Aminex®HXP-87P column (Biorad, 300 mm×7.8 mm) equipped with a refractive index detector (Varian 350 RI). The column temperature was 80° C. and the eluent consisted of sulphuric acid at a flow rate of 0.4 mL/min (Spectra System RI 150).

The results obtained show that the Δupp::ipa8 mutants are able to reduce acetone to isopropanol, in contrast with the WT strain or a Δupp mutant (FIG. 19).

Insertion of the celA Gene into the Genome of *Clostridium beijerinckii* NCIMB8052

The modification made consists of the insertion within the *C. beijerinckii* NCIMB8052 genome of the celA gene from *Neocallimastix patriciarum* under the control of the eglA promoter from *Clostridium saccharobutylicum* NCP262. This gene encodes an enzyme capable of degrading a cellulose substrate, called CMC (carboxymethyl cellulose). The gene and its promoter, 1667 bp in size, are inserted after the hbd gene, and allows the strain to degrade CMC (FIG. 20, Lopez-Contreras et al., 2001).

To carry out this insertion, two plasmids were used:

- the pEC500E_X_cas9 plasmid: expressing the cas9 gene under the control of the xylB inducible promoter from *Clostridium dificile* 630 (Nariya et al., 2011) (see FIG. 21 and SEQ ID NO: 29).
- the pS_XR_celAS1 plasmid expressing a guide RNA under the control of the xylB promoter and targeting the hbd gene from *C. beijerinckii* NCIMB8052. The plasmid also contains a repair template consisting of the celA gene under the control of the egl2 promoter, flanked by two regions of homology of 1001 and 1017 base pairs located on each side of the region targeted by the guide RNA. (See FIG. 22 and SEQ ID NO: 30).

These two plasmids were introduced sequentially into NCIMB8052. The induction of cas9 expression was carried out on CGM (6.25 g/L yeast extract; 0.5 g/L $MgSO_4.7H_2O$; 0.95 g/L $KH_2HPO_4$; 0.95 g/L $K_2HPO_4$; 0.013 g/L $MnSO_4.7H_2O$; 0.013 g/L $FeSO_4.7H_2O$; 1.25 g/L NaCl; 2.5 g/L $(NH_4)_2SO_4$; 2.5 g/L asparagine) containing spectinomycin and erythromycin as well as increasing concentrations of xylose inducer (FIG. 24).

The colonies obtained after induction on CGM containing 6% xylose were analysed by PCR with primer pair Cbei_325_F and Cbei_325_R which allows the amplification of a 2070-base pair product in strain NCIMB8052 and a 3718-base pair product in the case of integration of the celA gene:

```
Cbei_325_F (celA)
                                    (SEQ ID NO: 31)
5'-AGATAATTATGAAGTTAATCCTTAG-3';

Cbei_326_R (celA)
                                    (SEQ ID NO: 32)
5'-CATTTGCTTTCAGGTCTTCTTTTGCTG-3'.
```

The results of the PCR assays carried out on the control strain and on an independent colony obtained after induction confirm the insertion of the celA gene into NCIMB8052 (FIG. 25).

REFERENCES

Al-Hinai. M. A. et al. Novel system for efficient isolation of *Clostridium* double-crossover allelic exchange mutants enabling markerless chromosomal gene deletions and DNA integration. *Appl. Environ Microbiol.* 2012. 78(22): 8112-21.

Ran, F. A. et al. Genome engineering using the CRISPR-Cas9 system. *Nature protocols.* 2013. 8(11): 2281-308.

Barrangou, R. et al. CRISPR provides acquired resistance against viruses in prokaryotes. *Science.* 2007, 315(5819): 1709-12.

Banerjee, A. et al. Lactose-inducible system for metabolic engineering of *Clostridium ljungdahlii. Appl. Environ. Microbiol.* 2014.80(8): 2410-6.

Cartman, S. T. et al. Precise manipulation of the *Clostridium difficile* chromosome reveals a lack of association between the tcdC genotype and toxin production. *Appl. Environ. Microbiol.* 2012. 78(13): 4683-90.

Currie, D. H. et al. Functional heterologous expression of an engineered full length CipA from *Clostridium thermocellum* in *Thermoanaerobacterium saccharolyticum. Biotechnol. Biofuels.* 2013. 6(1): 32.

DiCarlo, J. E. et al. Genome engineering in *Saccharomyces cerevisiae* using CRISPR-Cas systems. *Nucleic Acids Res.*2013, 41(7): 4336-43.

Dong, H. et al. Development of an anhydrotetracycline-inducible gene expression system for solvent-producing *Clostridium acetobutylicum*: A useful tool for strain engineering. *Metab. Eng.* 2012. 14(1): 59-67.

D'Urzo, N. et al. High-level intracellular expression of heterologous proteins in *Brevibacillus choshinensis* SP3 under the control of a xylose inducible promoter. *Microb. Cell Fact.* 2013. 12: 12.

Egholm, M. et al. Peptide nucleic acids (PNA). Oligonucleotide analogs with an achiral peptide backbone. *J. Am. Chem. Soc.* 1992. 114(5): 1895-7.

Fonfara, I. et al. Phylogeny of Cas9 determines functional exchangeability of dual-RNA and Cas9 among orthologous type II CRISPR-Cas systems. *Nucleic acids res.* 2013, 42(4): 2577-90.

Gapes, J. R., Nimcevic, D., & Friedl, A. (1996). Long-Term Continuous Cultivation of *Clostridium beijerinckii* in a Two-Stage Chemostat with On-Line Solvent Removal. Applied and environmental microbiology, 62(9), 3210-3219.

Hartman, A.H. et al. Construction and characterization of a lactose-inducible promoter system for controlled gene expression in *Clostridium perfringens. Appl. Environ. Microbiol.* 77(2): 471-8.

Jinek, M. et al. A programmable dual-RNA-guided DNA endonuclease in adaptive bacterial immunity. *Science* 2012. 337(6096): 816-21.

Lee, J. et al. Metabolic engineering of *Clostridium acetobutylicum* ATCC 824 for isopropanol-butanol-ethanol fermentation. *Appl. Environ. Microbiol;* 2012. 78(5): 1416-23.

Lopez-Contreras A M, Smidt H, van der Oost J, Claassen P A M, Mooibroek H, de Vos W M. 2001. *Clostridium beijerinckii* Cells Expressing *Neocallismatix patriciarum* Glycoside Hydrolases Show Enhanced Lichenan Utilization and Solvent Production. Appl Environ Microbiol 67:5127-5133.

Lütke-Eversloh, T. Application of new metabolic engineering tools for *Clostridium acetobutylicum. Appl. Microbiol. Biotechnol.* 2014. 98(13): 5823-37.

Mali, P. et al. Cas9 as a versatile tool for engineering biology. *Nat. methods.* 2013, 10(10): 957-63.

Makarova, K. S., et al. Evolution and classification of the CRISPR-Cas systems. *Nat. Rev. Microbiol.* 2011, 9(6): 467-77.

Mearls, E. B. et al. Development of a regulatable plasmid-based gene expression system for *Clostridium thermocellum, Appl. Microbiol. Biotechnol.* 2015.99(18): 7589-99.

Nariya, H. et al., Development and characterization of a xylose-inducible gene expression system for *Clostridium perfringens, Appl. Environ. Microbiol.* 2011.77(23): 8439-41.

Nariya H, Miyata S, Kuwahara T, Okabe A. 2011. Development and characterization of a xylose-inducible gene expression system for *Clostridium perfringens. Appl Environ Microbiol* 77:8439-8441.

Newcomb, M. et al. Co-transcription of the celC gene cluster in *Clostridium thermocellum, Appl. Microbiol. Biotechnol.* 2011. 90(2): 625-34.

Wang, Y. et al. Markerless chromosomal gene deletion in *Clostridium beijerinckii* using CRISPR/Cas9 system. *J. Biotechnol.* 2015. 200: 1-5.

Xu, T. et al. Efficient genome editing in *Clostridium cellulolyticum* via CRISPR-Cas9 nickase. *Appl. Environ. Microbiol.* 2015 AEM-00873.

Zhang, N. et al. I-SceI-mediated scarless gene modification via allelic exchange in *Clostridium. J. Microbiol. Methods.* 2015, 108: 49-60.

Zhang, J. et al. A novel arabinose-inducible genetic operation system developed for *Clostridium cellulolyticum, Biotechnol. Biofuels.* 2015.8: 36.

The invention claimed is:

1. A genetic tool allowing the transformation by homologous recombination of a solventogenic bacterium of the genus *Clostridium*, wherein said genetic tool comprises:

a first vector comprising a first nucleic acid sequence encoding at least Cas9, wherein the Cas9 coding sequence is placed under the control of a promoter, and a second vector comprising a second nucleic acid sequence containing a repair template allowing, by a homologous recombination mechanism, the replacement of a portion of a Cas9- targeted bacterial DNA by a sequence of interest, in that i) at least one of said first or second nucleic acid sequences further encodes one or more guide RNAs (gRNAs), or ii) the genetic tool further comprises one or more guide RNAs, each guide RNA comprising a Cas9-enzyme-binding RNA structure and a sequence complementary to the portion of the Cas9-targeted bacterial DNA, said complementary sequence comprising at least 10 nucleotides, wherein Cas9 causes double-stranded cleavage of the bacterial DNA and the bacterial DNA is the DNA of a solvent-forming bacterium of the genus *Clostridium.*

2. The tool according to claim 1, wherein the sequence encoding said one or more guide RNAs is preceded by a promoter and said promoter or the promoter controlling Cas9 is an inducible promoter.

3. The tool according to claim 1, wherein the solventogenic bacterium of the genus *Clostridium* is selected from *C. acetobutylicum, C. cellulolyticum, C. phytofermentans, C. beijerinckii, C. saccharobutylicum, C. saccharoperbutylacetonicum, C. sporogenes, C. butyricum, C. aurantibutyricum* and *C. tyrobutyricum.*

4. The tool according to claim 3, wherein when the solventogenic bacterium is *C. acetobutylicum*, said *C. acetobutylicum* bacterium is strain ATCC824, and when the solventogenic bacterium is *C. beijerinckii*, said *C. beijerinckii* bacterium is strain DSM 6423.

5. The tool according to claim 1, wherein the Cas9 protein comprises SEQ ID NO: 1.

6. The tool according to claim 1, wherein the Cas9 promoter is an inducible promoter.

7. The tool according to claim 1, wherein the DNA sequence of interest encodes at least one product promoting the production of solvent, at least one enzyme involved in the conversion of aldehydes to alcohol, a membrane protein, a transcription factor, or a combination thereof.

8. The tool according to claim 1, wherein each vector is a plasmid.

9. A kit for transforming a bacterium of the genus *Clostridium* or for producing at least one solvent using a bacterium of the genus *Clostridium* comprising the components of a genetic tool comprising:

a first vector comprising a first nucleic acid sequence encoding at least Cas9, wherein the Cas9 coding sequence is placed under the control of a promoter, and a second vector comprising a second nucleic acid sequence containing a repair template allowing, by a homologous recombination mechanism, the replacement of a portion of a Cas9- targeted bacterial DNA by a sequence of interest, in that i) at least one of said first or second nucleic acid sequences further encodes one or more guide RNAs (gRNAs), or ii) the genetic tool further comprises one or more guide RNAs, each guide RNA comprising a Cas9- enzyme-binding RNA structure and a sequence complementary to the portion of the Cas9- targeted bacterial DNA, said complementary sequence comprising at least 10 nucleotides.

10. The kit according to claim 9, wherein the sequence encoding said one or more guide RNAs is preceded by a promoter and said promoter or the promoter controlling Cas9 is an inducible promoter.

11. The kit according to claim 10, said kit further comprising an inducer of said inducible promoter.

* * * * *